United States Patent

Tanaka et al.

Patent Number: 5,856,564
Date of Patent: Jan. 5, 1999

[54] CONDENSED BENZAZEPINE DERIVATIVE AND PHARMACEUTICAL COMPOSITION THEREOF

[75] Inventors: Akihiro Tanaka; Hiroyuki Koshio; Nobuaki Taniguchi; Akira Matsuhisa; Ken-ichiro Sakamoto; Atsuki Yamazaki; Takeyuki Yatsu, all of Ibaraki, Japan

[73] Assignee: Yamanouchi Pharmaceutical Co., Ltd., Tokyo, Japan

[21] Appl. No.: 972,271

[22] Filed: Nov. 18, 1997

Related U.S. Application Data

[62] Division of Ser. No. 586,686, Jan. 19, 1996, Pat. No. 5,723,606.

[30] Foreign Application Priority Data

Jul. 21, 1993 [JP] Japan .................................. 5-180435

[51] Int. Cl.[6] ................................................ C07C 229/00
[52] U.S. Cl. ............................................................ 562/457
[58] Field of Search ............................................. 562/457

[56] References Cited

U.S. PATENT DOCUMENTS

| | | | |
|---|---|---|---|
| 5,011,628 | 4/1991 | Cohen et al. | 252/589 |
| 5,225,402 | 7/1993 | Ogawa et al. | 514/23 |
| 5,244,898 | 9/1993 | Ogawa et al. | 514/213 |
| 5,258,510 | 11/1993 | Ogawa et al. | 540/476 |
| 5,512,563 | 4/1996 | Albigest et al. | 514/117 |

FOREIGN PATENT DOCUMENTS

| | | |
|---|---|---|
| 346 713 | 12/1989 | European Pat. Off. . |
| A10640592 | 3/1995 | European Pat. Off. . |
| 3255077 | 11/1991 | Japan . |

Primary Examiner—Mukund J. Shah
Assistant Examiner—Bruce Kifle
Attorney, Agent, or Firm—Sughrue, Mion, Zinn, Macpeak & Seas, PLLC

[57] ABSTRACT

This invention relates to nitrogen-containing aromatic 5-membered ring-condensed benzazepine derivatives represented by the general formula (I)

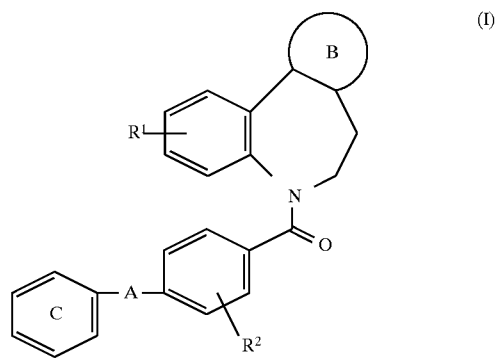

(symbols in the formula have the following meanings; ring B: a nitrogen-containing aromatic 5-membered ring having at least 1 nitrogen atom and optionally one oxygen or sulfur atom, which may optionally have substituent(s), $R^1$ and $R^2$: these may be the same or different from each other and each represents a hydrogen atom, a halogen atom, a lower alkyl group, an amino group which may optionally be substituted by lower alkyl group(s), or a lower alkoxy group, A: a single bond; a group represented by the formula —NHCO—$(CR^3R^4)_n$—, n: 0 or an integer of from 1 to 3, $R^3$ and $R^4$: these may be the same or different from each other and each represents a hydrogen atom, a lower alkyl group (provided that $R^3$ and $R^4$ may together form a lower alkylene group having 2 to 7 carbon atoms), and ring C: a benzene ring which may optionally have substituent(s)) and salts thereof; to pharmaceutical compositions which contain these compounds as an active ingredient and to intermediates which are useful in synthesizing these compounds. The compounds of this invention are useful as arginine vasopressin antagonists.

1 Claim, No Drawings

CONDENSED BENZAZEPINE DERIVATIVE AND PHARMACEUTICAL COMPOSITION THEREOF

This is a divisional of application Ser. No. 08/586,686 filed Jan. 19, 1996 U.S. Pat. No. 5,723,606.

TECHNICAL FIELD

This invention relates to novel aromatic and heterocyclic ring-condensed benzazepine derivatives which are useful as arginine vasopressin antagonists, to salts thereof, to pharmaceutical preparations which contain these compounds as an active ingredient and to intermediates which are useful for the synthesis of these compounds.

BACKGROUND ART

Arginine vasopressin (AVP) is a peptide which consists of 9 amino acid residues and is synthesized and secreted in the hypothalamo-neurohypophyseal system. As antagonists of the arginine vasopressin, peptide type compounds and non-peptide type compounds have been synthesized. For example, a compound disclosed in JP-A-2-32098 is known as the peptide type compound (the term "JP-A" as used herein means an "unexamined published Japanese patent application"). On the other hand, 2,3,4,5-tetrahydro-1H-benzazepine derivatives represented by the following general formula have been disclosed in EP-A-0514667 and JP-A-5-132466 as non-peptide type vasopressin antagonists.

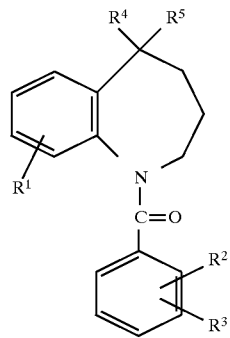

(As for symbols in the above formula, see aforementioned patent publications.)

Also, International Patent Publication No. 91/05549 disclosing the compound represented by the following general formula, and 2,3,4,5-tetrahydro-1H-benzodiazepine derivatives and 2,3,4,5-tetrahydro-1H-1-benzazepine derivatives disclosed in JP-A-4-154765 are known.

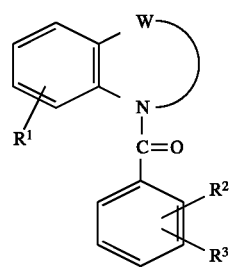

(As for symbols in the above formula, see aforementioned patent publications.)

Although various studies have been made as described above, creation of novel arginine vasopressin antagonists having more excellent profiles is still now an important clinical object.

On the other hand, almost no compound is known as a compound having a nitrogen-containing aromatic 5-membered ring-condensed benzazepine skeleton, which is the basic structure of the compound of the present invention, and only processes for the synthesis of a few compounds having such a ring structure have been reported in *J. Chem. Soc.*, Perkin Trans. 1 (1978) No. 8, 862–70 and *Org. Prep. Proced. Int.*, 25 (5), 602–6 (1993), but their structures are clearly different from the structure of the compound of the present invention. In addition, use of these compounds as pharmaceutical preparations have not been known.

DISCLOSURE OF THE INVENTION

The inventors of the present invention have conducted extensive studies on compounds having arginine vasopressin antagonism and accomplished the present invention based on the finding that a novel aromatic and heterocyclic ring-condensed benzazepine derivative represented by the following general formula (I) shows unexpectedly excellent arginine vasopressin antagonism.

Accordingly, the present invention relates to a nitrogen-containing aromatic 5-membered ring-condensed benzazepine derivative represented by the following formula (I) and a salt thereof.

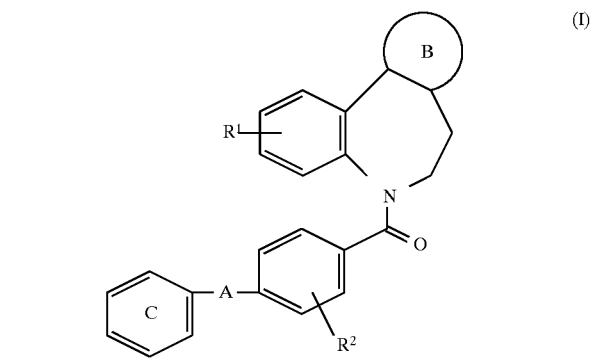

(Symbols in the formula have the following meanings; ring B: a nitrogen-containing aromatic 5-membered ring having at least 1 nitrogen atom and optionally one oxygen or sulfur atom, which may optionally have substituent(s), $R^1$, $R^2$: these may be the same or different from each other and each represents a hydrogen atom, a halogen atom, a lower alkyl group, an amino group which may optionally be substituted by lower alkyl group(s), a lower alkoxy group, A: a single bond; a group represented by the formula —NHCO—$(CR^3R^4)_n$—, n: 0 or an integer of from 1 to 3, $R^3$, $R^4$: these may be the same or different from each other and each represents a hydrogen atom, a lower alkyl group (provided that $R^3$ and $R^4$ may together form a lower alkylene group having 2 to 7 carbon atoms), and ring C: a benzene ring which may optionally have substituent(s).)

Further, the particularly preferable compound is the nitrogen-containing aromatic 5-membered ring-condensed benzazepine derivative (I) or a salt thereof wherein i) the ring B is a ring represented by the formula:

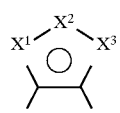

(symbols in the formula have the following meanings;
 $X^1$, $X^3$: one of them is a group represented by the formula =N—, and the other is a group represented by the formula —NR$^5$—, —O—, —S— or =N—,
 $X^2$: a group represented by the formula =CR$^6$—, —O—, —S— or =N—,
 $R^5$: a hydrogen atom, a lower alkyl group, and
 $R^6$:
  a) a hydrogen atom,
  b) a lower alkyl, lower alkenyl or loweralkynyl group, which is unsubstituted or substituted by the following groups,
   an amino group; a mono or di lower alkylamino group; a lower alkanoylamino group substituted by an amino group or a mono or di lower alkylamino group; a protected amino group; a 1-pyrrolidinyl group; a piperidino group; a morpholino group; a 1-piperazinyl, 1-imidazolidinyl, 1-homopiperazinyl or 1-pyrazolidinyl group, which may optionally be substituted by a lower alkyl group at the nitrogen atom of the ring; a guanidino group; an amidino group; a hydroxyl group; a lower alkoxyl group; a cyano group; a carbamoyl group; a carboxyl group; a lower alkoxycarbonyl group; a lower alkanoyloxy group; or a phenyl, imidazolyl, pyridyl, pyrazinyl, pyrimidinyl, pyridazinyl, pyrazolyl, pyrrolyl, tetrazolyl, triazolyl, thiazolyl or oxazolyl group, which may optionally be substituted by a lower alkyl group, a halogen atom, a lower alkoxyl group, an amino group, a mono or di lower alkylamino group, a hydroxyl group or a carboxyl group,
  c) a cycloalkyl group having 3 to 8 carbon atoms,
  d) an amino group; an amino group mono- or di-substituted by a lower alkyl group, a lower alkenyl group, a lower alkynyl group or a lower alkanoyl group (these groups may further be substituted by an amino group; a mono or di lower alkylamino group; a 1-pyrrolidinyl group; a piperidino group; a morpholino group; or a 1-piperazinyl, 1-imidazolidinyl or 1-homopiperazinyl group which may optionally be substituted by a lower alkyl group at the nitrogen atom of the ring); a 1-pyrrolidinyl group; a piperidino group; a morpholino group; or a 1-piperazinyl, 1-imidazolidinyl or 1-homopiperazinyl group which may optionally be substituted by a lower alkyl group,
  e) a guanidino group, an amidino group, or
  f) a hydroxyl group, a lower alkoxyl group, a mercapto group, a lower alkylthio group), and ii) the ring C is a benzene ring which may optionally have 1 to 5 substituents respectively selected from
   a) a lower alkyl, lower alkenyl or lower alkynyl group, which may optionally be substituted by a halogen atom or a hydroxyl group,
   b) a lower alkoxy group which may optionally be substituted by a halogen atom, a cyano group, a hydroxyl group, a carboxyl group, a lower alkoxycarbonyl group, a lower alkanoyl group, a lower alkanoyloxy group, a carbamoyl group, a lower alkylaminocarbonyl group or a phthalimido group; a hydroxyl group; a mercapto group; or a lower alkylthio group,
   c) a halogen atom; a cyano group,
   d) a carboxyl group; a lower alkoxycarbonyl group; a lower alkanoyl group; a lower alkanoyloxy group; a carbamoyl group; a lower alkylaminocarbonyl group,
   e) an amino group; a mono or di lower alkylamino group; a lower alkanoylamino group; a 1-pyrrolidinyl group; a piperidino group; a morpholino group; or a 1-piperazinyl, 1-imidazolidinyl or 1-homopiperazinyl group which may optionally be substituted by a lower alkyl group at the nitrogen atom of the ring,
   f) a cycloalkyl group,
   g) a phenyl group which may optionally be substituted by a lower alkyl group, a lower alkenyl group, a lower alkynyl group, a halogen atom, a lower alkoxy group, an amino group, a mono or di lower alkylamino group, a hydroxyl group or a carboxyl group, and
   h) an imidazolyl, triazolyl, tetrazolyl, pyrrolyl, pyridyl, pyrazinyl or pyrimidinyl group, which may optionally be substituted by a lower alkyl group, a cycloalkyl group or a phenyl group.

The present invention also relates to a pharmaceutical composition, especially an arginine vasopressin antagonist, which contains the above nitrogen-containing aromatic 5-membered ring-condensed benzazepine derivative or a salt thereof as an active ingredient.

Moreover, the present invention also relates to (biphenyl-2-ylcarboxamide)benzoic acid which is useful as an intermediate for the synthesis of the above nitrogen-containing aromatic 5-membered ring-condensed benzazepine derivative.

Chemical structure of the compound of the present invention is characterized in that its basic structure is a nitrogen-containing aromatic 5-membered ring-condensed benzazepine ring to which a substituted or unsubstituted biphenylcarbonyl group, a substituted or unsubstituted benzoylaminobenzoyl group or a substituted or unsubstituted phenylalkanoylaminobenzoyl group has been linked. The compound of the present invention having such a basic structure has excellent arginine vasopressin antagonism, is excellent in oral absorption and shows proper prolonged action because of its stability to metabolism in the living body.

The following describes the compound of the present invention in detail.

With regard to the nitrogen-containing aromatic 5-membered ring moiety of the "nitrogen-containing aromatic 5-membered ring having at least 1 nitrogen atom and optionally one oxygen or sulfur atom, which may optionally have substituent(s)" as the ring B of the compound of the present invention represented by the formula (I), a pyrrole ring, a pyrazole ring, an imidazole ring, a triazole ring, an isoxazole ring, an oxazole ring, an isothiazole ring, a thiazole ring, an oxadiazole ring, a thiadiazole ring and the like may be exemplified. Each of these rings may optionally have substituent(s) which will be described later and is condensed with a benzazepine ring through its adjacent two ring-forming atoms.

Particularly, as the nitrogen-containing aromatic 5-membered ring moiety of the ring B, a nitrogen-containing aromatic 5-membered ring represented by

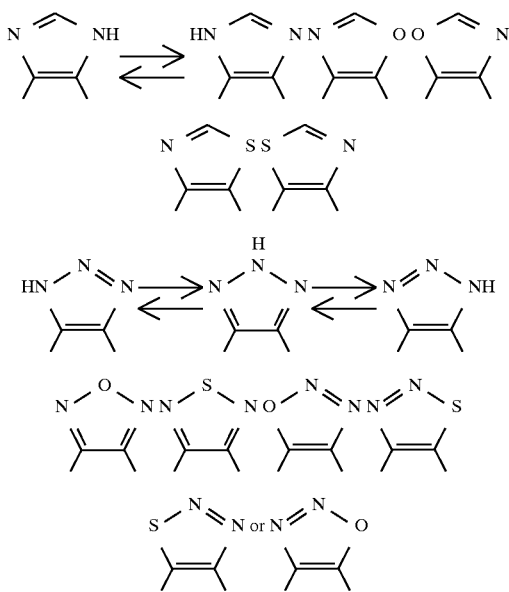

is preferable, a nitrogen-containing aromatic 5-membered ring represented by

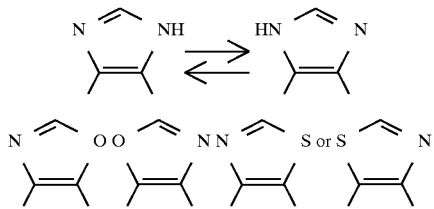

is more preferable, and a nitrogen-containing aromatic 5-membered ring represented by

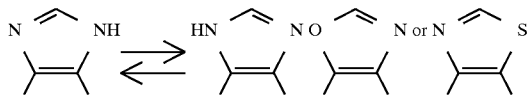

is most preferable.

In these rings, a hydrogen atom on the ring-forming carbon or nitrogen atom may optionally be a substituent described in the following.

The substituent to be located on the nitrogen-containing aromatic 5-membered ring of the ring B or on the benzene ring of the ring C may be selected from those which are conventionally used in the art as substituents on aromatic heterocyclic rings or a benzene ring. The nitrogen-containing aromatic 5-membered ring of the ring B may optionally have 1 to 2 substituents, and the benzene ring of the ring C may optionally have 1 to 5 (preferably 1 to 3) substituents. Preferably, the substituent on the benzene ring of the ring C may be located at the o (ortho) position. Examples of these substituents include a substituted or unsubstituted alkyl, alkenyl or alkynyl group, a substituted or unsubstituted cycloalkyl or cycloalkenyl group, a substituted or unsubstituted aryl group and a substituted or unsubstituted saturated or unsaturated heterocyclic group, as well as a halogen atom, a hydroxyl group, an alkoxyl group, a substituted alkoxyl group, an alkenyloxy group, an alkynyloxy group, a cycloalkyloxy group, a cycloalkenyloxy group, an aryloxy group, an aralkyloxy group, an aralkenyloxy or aralkynyloxy group, a mercapto group, an alkylthio group, an alkenylthio group, an alkynylthio group, a cycloalkylthio group, a cycloalkenylthio group, an arylthio group, an aralkylthio group, an aralkenylthio or aralkynylthio group, an alkoxycarbonyl group, an alkenyloxycarbonyl group, an alkynyloxycarbonyl group, a cycloalkyloxycarbonyl group, a cycloalkenyloxycarbonyl group, an aryloxycarbonyl group, an aralkyloxycarbonyl group, an aralkenyloxycarbonyl or aralkynyloxycarbonyl group, an alkylaminocarbonyl group, an aliphatic or aromatic acyl or acyloxy group, a carbamoyl group, a carboxyl group, a sulfone group, an oxo group, a thioxo group, a cyano group, a nitro group, an amino group, a mono- or di-substituted amino group, a guanidino group, an amidino group and a substituted or unsubstituted imino group. In addition to these groups, a divalent group which is substituted or not substituted, may contain hetero atoms (for example, 1 to 3 nitrogen, oxygen and/or sulfur atoms), and forms a condensed ring with the benzene ring through its binding to the adjacent carbon atoms of the benzene ring, such as a lower alkylene group, a lower alkenylene group, a lower alkynylene group or a lower alkylenedioxy group, may be used as the substituent for the benzene ring.

Examples of the substituents of "substituted alkyl group", "substituted alkenyl group" and "substituted alkynyl group" as the aforementioned substituents of the nitrogen-containing aromatic 5-membered ring or the benzene ring include a cycloalkyl group, a cycloalkenyl group, a substituted or unsubstituted aryl group, a substituted or unsubstituted saturated or unsaturated heterocyclic group, a halogen atom, a hydroxyl group, an alkoxyl group, an alkenyloxy group, an alkynyloxy group, a cycloalkyloxy group, a cycloalkenyloxy group, an aryloxy group, an aralkyloxy group, an aralkenyloxy or aralkynyloxy group, a mercapto group, an alkylthio group, an alkenylthio group, an alkynylthio group, a cycloalkylthio group, a cycloalkenylthio group, an arylthio group, an aralkylthio group, an aralkenylthio or aralkynylthio group, an alkoxycarbonyl group, an alkenyloxycarbonyl group, an alkynyloxycarbonyl group, a cycloalkyloxycarbonyl group, a cycloalkenyloxycarbonyl group, an aryloxycarbonyl group, an aralkyloxycarbonyl group, an aralkenyloxycarbonyl or aralkynyloxycarbonyl group, an alkylaminocarbonyl group, an aliphatic or aromatic acyl or acyloxy group, a carboxyl group, a sulfone group, an oxo group, a thioxo group, a carbamoyl group, a cyano group, a nitro group, an amino group, a mono- or di-substituted amino group, a protected amino group, a guanidino group, an amidino group and a substituted or unsubstituted imino group.

Examples of the substituents of the aforementioned "substituted alkoxy group" include a halogen atom, a cyano group, a hydroxyl group, a carboxyl group, a lower alkoxycarbonyl group, a lower alkanoyl group, a lower alkanoyloxy group, a carbamoyl group, a lower alkylaminocarbonyl group, a phthalimido group and the like.

Examples of the substituents of the "substituted cycloalkyl or cycloalkenyl group" include a lower alkyl group, a lower alkenyl group, a lower alkynyl group, a lower alkoxy group, a lower alkanoyl group, a lower alkanoyloxy group, a lower alkoxycarbonyl group, an amino group, a mono or di lower alkylamino group, a hydroxyl group, a carboxyl group, a carbamoyl group and the like.

Examples of the substituents of the "substituted aryl group" include a lower alkyl group, a lower alkenyl group, a lower alkynyl group, a halogen atom, a lower alkoxyl group, an amino group, a mono or di lower alkylamino group, a hydroxyl group, a carboxyl group and the like.

The "substituted saturated or unsaturated heterocyclic group" may preferably be a nitrogen-containing heterocyclic ring, more preferably a nitrogen-containing aromatic 5- or 6-membered ring (most preferably an imidazolyl group, a pyridyl group, a pyrazinyl group, a pyrimidinyl group, a pyridazinyl group, a pyrazolyl group, a pyrrolyl group, a tetrazolyl group, a triazolyl group, a thiazolyl group or an oxazolyl group) and a nitrogen-containing saturated 4- to 7-membered ring (most preferably a pyrrolidinyl group, a piperidyl group, a morpholinyl group, a piperazinyl group, an imidazolidinyl group, a homopiperazinyl group or a pyrazolidinyl group). Examples of their substituents include a lower alkyl group, a cycloalkyl group, a phenyl group, a halogen atom, a lower alkoxyl group, an amino group, a mono or di lower alkylamino group, a hydroxyl group, a carboxyl group and the like.

Examples of the substituents of the "mono- or di-substituted amino group" include a lower alkyl group, a lower alkenyl group, a lower alkynyl group, a lower alkanoyl group and the like, and these groups may optionally be further substituted by the following groups:

an amino group; a mono or di lower alkylamino group; a 1-pyrrolidinyl group; a piperidino group; a morpholino group; and a 1-piperazinyl, 1-imidazolidinyl or 1-homopiperazinyl group which may optionally be substituted by a lower alkyl group at the nitrogen atom of the ring.

Examples of the substituents of the "substituted imino group" include an alkyl group, an aryl group, an aralkyl group and the like.

Of the aforementioned substituents on the nitrogen-containing aromatic 5-membered ring of the ring B or the benzene ring of the ring C, substituents to be located on carbon atoms of the ring B may preferably be a) a lower alkyl, lower alkenyl or lower alkynyl group, which is unsubstituted or substituted by the following groups, an amino group; a mono or di lower alkylamino group; a lower alkanoylamino group substituted by an amino group or a mono or di lower alkylamino group; a protected amino group; a 1-pyrrolidinyl group; a piperidino group; a morpholino group; a 1-piperazinyl, 1-imidazolidinyl, 1-homopiperazinyl or 1-pyrazolidinyl group, which may optionally be substituted by a lower alkyl group at the nitrogen atom of the ring; a guanidino group; an amidino group; a hydroxyl group; a lower alkoxyl group; a cyano group; a carbamoyl group; a carboxyl group; a lower alkoxycarbonyl group; a lower alkanoyloxy group; and a phenyl, imidazolyl, pyridyl, pyrazinyl, pyrimidinyl, pyridazinyl, pyrazolyl, pyrrolyl, tetrazolyl, triazolyl, thiazolyl or oxazolyl group, which may optionally be substituted by a lower alkyl group, a halogen atom, a lower alkoxyl group, an amino group, a mono or di lower alkylamino group, a hydroxyl group or a carboxyl group, b) a cycloalkyl group having 3 to 8 carbon atoms, c) an amino group; an amino group mono- or di-substituted by a lower alkyl group, a lower alkenyl group, a lower alkynyl group or a lower alkanoyl group (these groups may further be substituted by an amino group; a mono or di lower alkylamino group; a 1-pyrrolidinyl group; a piperidino group; a morpholino group; or a 1-piperazinyl, 1-imidazolidinyl or 1-homopiperazinyl group which may optionally be substituted by a lower alkyl group at the nitrogen atom of the ring); a 1-pyrrolidinyl group; a piperidino group; a morpholino group; or a 1-piperazinyl, 1-imidazolidinyl or 1-homopiperazinyl group which may optionally be substituted by a lower alkyl group at the nitrogen atom of the ring, d) a guanidino group, an amidino group, or e) a hydroxyl group, a lower alkoxyl group, a mercapto group, a lower alkylthio group, more preferably a) a lower alkyl group which is unsubstituted or substituted by the following groups, an amino group; a mono or di lower alkylamino group; a lower alkanoylamino group substituted by an amino group or a mono or di lower alkylamino group; a 1-pyrrolidinyl group; a piperidino group; a morpholino group; a 1-piperazinyl group which may optionally be substituted by a lower alkyl group at the nitrogen atom of the ring; a guanidino group; an amidino group; or a phenyl, imidazolyl, pyridyl, pyrazinyl, pyrimidinyl, pyridazinyl, pyrazolyl, pyrrolyl, tetrazolyl or triazolyl group, which may optionally be substituted by a lower alkyl group, b) a cycloalkyl group having 3 to 8 carbon atoms, c) an amino group; an amino group mono- or di-substituted by a lower alkyl group or a lower alkanoyl group (these groups may further be substituted by an amino group or a mono or di lower alkylamino group), or d) a guanidino group, an amidino group, most preferably a) a lower alkyl group which is unsubstituted or substituted by the following groups, an amino group; a mono or di lower alkylamino group; a morpholino group; an imidazolyl group which may optionally be substituted by a phenyl group or a lower alkyl group; or a pyridyl group, b) a cyclopropyl group, c) an amino group; a dimethylamino-substituted lower alkylamino group; or an amino lower alkanoylamino group, or d) a guanidino group.

A lower alkyl group is particularly preferred as the substituent on the nitrogen atom of the ring B.

Substituents to be located on the benzene ring of the ring C may preferably be a) a lower alkyl, lower alkenyl or lower alkynyl group, which may optionally be substituted by a halogen atom or a hydroxyl group, b) a lower alkoxy group which may optionally be substituted by a halogen atom, a cyano group, a hydroxyl group, a carboxyl group, a lower alkoxycarbonyl group, a lower alkanoyl group, a lower alkanoyloxy group, a carbamoyl group, a lower alkylaminocarbonyl group or a phthalimido group; a hydroxyl group; a mercapto group; or a lower alkylthio group, c) a halogen atom; a cyano group, d) a carboxyl group; a lower alkoxycarbonyl group; a lower alkanoyl group; a lower alkanoyloxy group; a carbamoyl group; a lower alkylaminocarbonyl group;

e) an amino group; a mono or di lower alkylamino group; a lower alkanoylamino group; a 1-pyrrolidinyl group; a piperidino group; a morpholino group; or a 1-piperazinyl, 1-imidazolidinyl or 1-homopiperazinyl group which may optionally be substituted by a lower alkyl group at the nitrogen atom of the ring, f) a cycloalkyl group, g) a phenyl group which may optionally be substituted by a lower alkyl group, a lower alkenyl group, a lower alkynyl group, a halogen atom, a lower alkoxy group, an amino group, a mono or di lower alkylamino group, a hydroxyl group or a carboxyl group, or h) an imidazolyl, triazolyl, tetrazolyl, pyrrolyl, pyridyl, pyrazinyl or pyrimidinyl group, which may optionally be substituted by a lower alkyl group, a cycloalkyl group or a phenyl group, more preferably a lower alkyl group; a lower alkoxy group; a hydroxyl group; a halogen atom; a cycloalkyl group; a phenyl group which may optionally be substituted by a lower alkyl group, a lower alkenyl group, a lower alkynyl group, a halogen atom, a lower alkoxy group, an amino group, a mono or di lower alkylamino group, a hydroxyl group or a carboxyl group; or an imidazolyl, triazolyl, tetrazolyl or pyrrolyl group, which may optionally be substituted by a lower alkyl group, most preferably an unsubstituted phenyl group or a phenyl group substituted by a lower alkyl group.

Unless otherwise noted, the term "lower" as used in the definition of the general formula of the present invention means a straight or branched carbon chain having 1 to 6 carbon atoms.

Examples of the "alkyl group" include straight- or branched-chain alkyl groups, preferably a lower alkyl group. Illustrative examples of the "lower alkyl group" include alkyl groups each having 1 to 6 carbon atoms, such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like, of which methyl and ethyl groups are preferred.

Examples of the "alkenyl group" include straight- or branched-chain alkenyl groups, preferably a lower alkenyl group. Illustrative examples of the "lower alkenyl group" include alkenyl groups each having 2 to 6 carbon atoms, such as vinyl, allyl, 1-propenyl, isopropenyl, 1-butenyl, 2-butenyl, 3-butenyl, 2-methyl-1-propenyl, 2-methylallyl, 1-methyl-1-propenyl, 1-methylallyl, 1,1-dimethylvinyl, 1-pentenyl, 2-pentenyl, 3-pentenyl, 4-pentenyl, 3-methyl-1-butenyl, 3-methyl-2-butenyl, 3-methyl-3-butenyl, 2-methyl-1-butenyl, 2-methyl-2-butenyl, 2-methyl-3-butenyl, 1-methyl-1-butenyl, 1-methyl-2-butenyl, 1-methyl-3-butenyl, 1,1-dimethylallyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1,1-dimethyl-1-butenyl, 1,1-dimethyl-2-butenyl, 1,1-dimethyl-3-butenyl, 3,3-dimethyl-1-butenyl, 1-methyl-1-pentenyl, 1-methyl-2-pentenyl, 1-methyl-3-pentenyl, 1-methyl-4-pentenyl, 4-methyl-1-pentenyl, 4-methyl-2-pentenyl, 4-methyl-3-pentenyl and the like.

Examples of the "alkynyl group" include straight- or branched-chain alkynyl groups, preferably a lower alkynyl group. Illustrative examples of the "lower alkynyl group" include straight- or branched-chain alkynyl groups each having 2 to 6 carbon atoms, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 2-methyl-3-butynyl, 1-methyl-2-butynyl, 1-methyl-3-butynyl, 1,1-dimethyl-2-propynyl, 1-hexynyl, 2-hexynyl, 3-hexynyl, 4-hexynyl, 5-hexynyl and the like.

The "cycloalkyl group" or "cycloalkenyl group" are preferably cycloalkyl or cycloalkenyl groups having 3 to 8 carbon atoms, such as cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl and the like, of which cyclohexyl and cyclohexenyl groups are respectively preferred.

The "aryl group" is preferably an aryl group having 6 to 14 carbon atoms, such as phenyl, biphenyl, naphthyl, anthryl, phenanthryl and the like, of which phenyl and naphthyl groups are preferred and phenyl group is particularly preferred.

Examples of the "alkoxy group" include straight- or branched-chain alkoxy groups, preferably a lower alkoxy group. The "lower alkoxyl group" is preferably a lower alkoxyl group having the aforementioned lower alkyl group as its alkyl moiety, and examples of the "lower alkoxyl group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy, hexyloxy and the like, of which methoxy and isopropoxy groups, especially a methoxy group, are preferred.

Examples of the "alkanoyl group" include straight- or branched-chain alkanoyl groups, preferably a lower alkanoyl group. Illustrative examples of the "lower alkanoyl group" include lower acyl groups each having 1 to 6 carbon atoms derived from saturated aliphatic carboxylic acids, such as formyl, acetyl, propionyl, bytylyl, isobutylyl, valeryl, isovaleryl, pivaloyl, hexanoyl and the like.

The "alkanoyloxy group" is preferably a group containing the aforementioned lower alkanoyl group as its alkanoyl moiety, such as acetoxy, propionyloxy and the like.

The "alkanoylamino group" is preferably a group containing the aforementioned lower alkanoyl group as its alkanoyl moiety, such as acetamide, propionylamino and the like.

Examples of the "halogen atom" include fluorine, chlorine, bromine and iodine.

The term "mono or di lower alkylamino group" means an amino group mono- or di-substituted by the aforementioned lower alkyl group, its illustrative examples including mono lower alkylamino groups such as methylamino, ethylamino, propylamino, isopropylamino, butylamino, isobutylamino, sec-butylamino, tert-butylamino, pentyl(amyl)amino, isopentylamino, neopentylamino, tert-pentylamino, hexylamino and the like and symmetric or asymmetric di lower alkylamino groups such as dimethylamino, diethylamino, dipropylamino, diisopropylamino, dibutylamino, diisobutylamino, ethylmethylamino, methylpropylamino and the like.

The "aralkyl group", "aralkenyl group" or "aralkynyl group" is preferably an aralkyl, aralkenyl or aralkynyl group which is composed of the aforementioned aryl moiety (especially a phenyl or naphthyl group) and a lower alkyl, lower alkenyl or lower alkynyl moiety.

The "alkenyloxy group", "alkynyloxy group", "cycloalkyloxy group", "cycloalkenyloxy group", "aryloxy group", "aralkyloxy group", "aralkenyloxy group" or "aralkynyloxy group" and "alkylthio group", "alkenylthio group", "alkynylthio group", "cycloalkylthio group", "cycloalkenylthio group", "arylthio group", "aralkylthio group", "aralkenylthio group" or "aralkynylthio group" are preferably those groups having a lower hydrocarbon chain as the respective hydrocarbon group moiety and, if the "alkenyloxy group" is taken as an example, the "alkenyloxy group" is preferably a lower alkenyloxy group having the aforementioned lower alkenyl group as its alkenyl moiety.

The "alkoxycarbonyl group" is preferably a lower alkoxycarbonyl group having the aforementioned lower alkyl group as its alkyl moiety, which is formed by the esterification of a straight- or branched-chain alcohol having 1 to 6 carbon atoms with carbonyl group, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl or the like.

In the same manner, "alkenyloxycarbonyl group", "alkynyloxycarbonyl group", "cycloalkyloxycarbonyl group", "cycloalkenyloxycarbonyl group", "aryloxycarbonyl group", "aralkyloxycarbonyl group", "aralkenyloxycarbonyl group", "aralkynyloxycarbonyl group" or "alkylaminocarbonyl group" is preferably such a group that, if the "alkenyloxycarbonyl group" is taken as an example, a lower alkenyloxycarbonyl group having the aforementioned lower alkenyl group as its alkenyl moiety.

The "aliphatic acyl group" is preferably a lower acyl group derived from a saturated or unsaturated lower fatty acid, and the aforementioned lower alkanoyl group may be preferable. Illustrative examples of "aromatic acyl group" include benzoyl, toluoyl, salicyl, naphthoyl, phthaloyl and the like group. The "acyloxy group" is a group which contains the aforementioned lower alkanoyl or aromatic acyl group as its acyl moiety, with its preferred examples including acetoxy, benzoyloxy and the like.

Illustrative examples of the "protected amino group" include amino groups each of which being protected with an aliphatic or aromatic acyl group, a carbamoyl group, a carbamide group, a phthaloyl group, or the like.

The "lower alkylene group" is a straight or branched divalent carbon chain having 1 to 7 carbon atoms, with its illustrative examples including methylene, ethylene, propylene, tetramethylene, 2-methyltrimethylene, 1-ethylethylene, pentamethylene, 1,2-diethylethylene, hexamethylene and the like.

The "lower alkenylene group" is a straight or branched divalent carbon chain having 2 to 7 carbon atoms, with its illustrative examples including vinylene, propenylene, 2-propenylene, 1-methylvinylene, 2-methylvinylene, butenylene, 2-butenylene, 3-butenylene, 1-methylpropenylene, 1-methyl-2-propenylene, 2-pentenylene, 1-methyl-1-butenylene, 2-hexenylene and the like.

The "lower alkynylene group" is a straight or branched divalent carbon chain having 2 to 7 carbon atoms, with its illustrative examples including ethynylene, 2-propynylene, 2-butynylene, 3-butynylene, 1-methyl-2-propynylene, 2-pentynylene, 2-hexynylene and the like.

The "dimethylamino-substituted lower alkylamino group" is an amino group which is mono-substituted by the aforementioned lower alkyl group that is further substituted by dimethylamino group(s).

The "amino lower alkanoylamino group" is an amino group which is mono-substituted by the aforementioned lower alkanoyl group that is further substituted by amino group(s).

The salt of the compound of the present invention is an acid addition salt with an inorganic or organic acid or a salt with an inorganic or organic base, and a pharmaceutically acceptable salt is preferable. Illustrative examples of such salts include: an acid addition salt with a mineral acid such as hydrochloric acid, hydrobromic acid, hydroiodic acid, sulfuric acid, nitric acid, phosphoric acid or the like, an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid or the like or an acidic amino acid such as aspartic acid, glutamic acid or the like; and a salt with an inorganic base such as sodium, potassium, magnesium, calcium, aluminium or the like, an organic base such as methylamine, ethylamine, ethanolamine or the like or a basic amino acid such as lysine, ornithine or the like. Also useful are quaternary ammonium salts. Illustrative examples of quaternary ammonium salts include a lower alkyl halide, a lower alkyl trifurate, a lower alkyl tosylate, a benzyl halide and the like, preferably methyl iodide, benzyl chloride and the like.

The compound of the general formula (I) may form optical isomers due to an asymmetric carbon atom or geometrical isomers due to a double bond or a cyclohexane ring. Mixtures and separated forms of various isomers including such geometrical isomers and optical isomers are also included in the scope of the present invention. Also included in the present invention are hydrates, solvates, tautomers an d the like of the compound of general formula (I). Some of the compounds of the present invention show polymorphism and all types of polymorphism of the inventive compound are also included in the present invention.

(Production Process)

The compound of the present invention and salts thereof can be produced by various synthetic techniques making use of the characteristics of its basic skeleton or the type of substituents. In that case, it may be effective from the viewpoint of production techniques to substitute an amino group, a carbonyl group, a hydroxyl group and a mercapto group of an intermediate or the compound of the present invention with appropriate protective groups, namely functional groups which can easily be converted into an amino group, a carbonyl group, a hydroxyl group and a mercapto group. Protective groups disclosed, for instance, by Greene and Wuts in "Protective Groups in Organic Synthesis, 2nd ed." may optionally be used in accordance with the reaction conditions. In addition to these groups, hydroxymethylene group (CH—OH) is also a functional group which can easily be converted into a carbonyl group, and such a functional group can also be used as the protective group for a carbonyl group.

The following describes typical examples of the process for the production of the compound of the present invention.

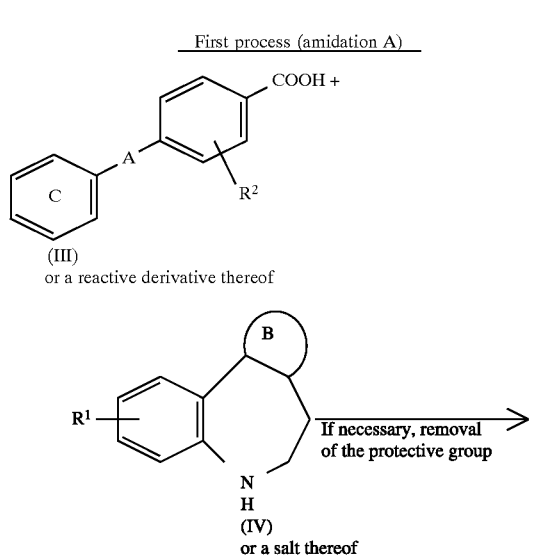

-continued
First process (amidation A)

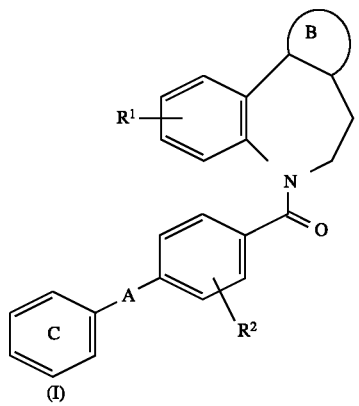

(In the above formulae, $R^1$, $R^2$, A, ring B and ring C have the same respective meanings as described in the foregoing.)

The compound (I) of the present invention can be produced by subjecting the substituted benzoic acid represented by the formula (III) which may optionally be protected, or a reactive derivative thereof, and the 5-membered nitrogen-containing aromatic and heterocyclic ring-condensed benzazepine derivative represented by the formula (IV) which may optionally be protected, or a salt thereof, to amidation in the usual way and by, if necessary, removing the protective group.

Examples of the reactive derivative of the compound (III) include: its usual esters such as methyl ester, ethyl ester, isobutyl ester, tert-butyl ester and the like; its acid halides such as acid chloride, acid bromide and the like; its acid azides; its active esters obtained by allowing it to react with a phenolic compound such as p-nitrophenol or an N-hydroxylamine compound such as 1-hydroxysuccinimide, 1-hydroxybenzotriazole or the like; its symmetric acid anhydrides; and its mixed acid anhydrides including organic acid-type mixed acid anhydrides obtained by allowing it to react with halocarboxylic acid alkyl esters such as alkylcarbonic acid halides or pivaloyl halides and phosphoric acid-type mixed acid anhydrides obtained by allowing it to react with diphenylphosphoryl chloride or N-methylmorpholine.

Also, when the compound (III) is allowed to react as a free acid, as an active ester without isolation, or the like, it is desirable to use a condensing agent such as dicyclohexylcarbodiimide, carbonyldiimidazole, diphenylphosphorylamide, diethylphosphoryl cyanide, 1-ethyl-3-(3-dimethylaminopropyl)carbodiimide hydrochloride or the like.

The reaction may be carried out generally in an inert organic solvent selected, for example, from halogenated hydrocarbons such as dichloromethane, dichloroethane, chloroform and the like, aromatic hydrocarbons such as benzene, toluene, xylene and the like, ethers such as ether, tetrahydrofuran and the like, esters such as ethyl acetate and the like, N,N-dimethylformamide and dimethylsulfoxide depending on the used reactive derivative, condensing agent and the like, and at a cooling temperature or at a temperature of from cooling temperature to room temperature or from room temperature to heating temperature depending on the reactive derivative used.

In order to effect smooth progress of the reaction, it may sometimes be advantageous to use the compound (III) in an excess amount or carry out the reaction in the presence of a base such as N-methylmorpholine, trimethylamine, triethylamine, N,N-dimethylaniline, pyridine, 4-(N,N-dimethylamino)pyridine, picoline, lutidine or the like. Pyridine can be used also as a solvent.

The reaction may be effected preferably in the absence of a mercapto group and reactive amino, carboxy, hydroxy and the like groups, but the product of interest can be obtained by carrying out the reaction after introducing protective groups and removing the protective groups after completion of the reaction.

Method for the removal of protective groups varies depending on the type of the protective group used.

For example, when the protective group for an amino group is a substituted or unsubstituted benzyloxycarbonyl group or the like, catalytic reduction may be effective and, in some cases, acid treatment with hydrobromic acid/acetic acid, hydrobromic acid/trifluoroacetic acid, hydrofluoric acid and the like. In the case of other urethane type protective groups such as tert-butoxycarbonyl group and the like, it is advantageous to employ acid treatment with hydrobromic acid/acetic acid, trifluoroacetic acid, hydrochloric acid, hydrochloric acid/acetic acid, hydrochloric acid/dioxane and the like.

When the protective group for an amino group is the group which forms a phthalimido group together with the nitrogen atom of the amino group, a primary amino group can be formed through the removal of the phthaloyl group by its treatment with hydrazines such as hydrazine, methylhydrazine, ethylhydrazine and the like, ammonia or primary amines such as methylamine, ethylamine, propylamine and the like.

The protective groups for a carboxyl group can easily be removed by saponification when the protective group is methyl and ethyl groups; by catalytic reduction or saponification when the protective group is a benzyl group and various substituted benzyl groups; by the aforementioned acid treatment when the protective group is tert-butyl group; and by contact with water when the protective group is a trimethylsilyl group.

In the case of protective groups for a mercapto group and a hydroxyl group, they can be removed in most cases by the sodium/liquid ammonia treatment or the hydrofluoric acid treatment, certain types of the protective groups (for example, O-benzyl, O-benzyloxycarbonyl and S-p-nitrobenzyl) can be removed by catalytic reduction, and acyl-type protective groups can be removed by their hydrolysis in the presence of an acid or an alkali.

These treatments can be carried out in the usual way.

In this connection, the starting compounds (III) and (IV) can easily be obtained by the aforementioned amidation reaction or a cyclization reaction which will be described later.

Second process (amidation B)

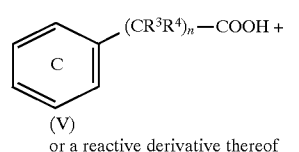

or a reactive derivative thereof

-continued
Second process (amidation B)

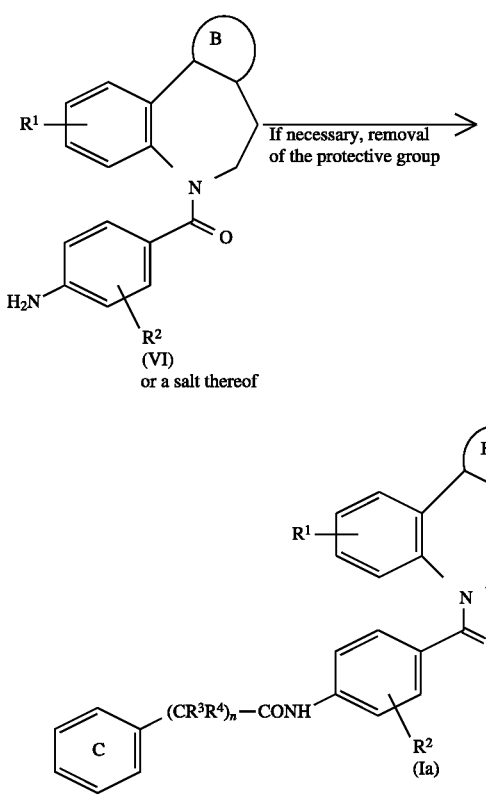

(In the above formulae, $R^1$, $R^2$, $R^3$, $R^4$, n, ring B and ring C have the same respective meanings as described in the foregoing.)

The compound (Ia) as one of the compounds of the present invention, in which A is —$(CR^3R^4)_n$—CONH—, can be produced by subjecting the corresponding carboxylic acid (V) which may optionally have a protective group, or a reactive derivative thereof, and the corresponding amine (VI) which may optionally have a protective group, or a salt thereof, to amidation reaction in the usual way and by, if necessary, removing the protective group.

Types of the reactive derivatives, reaction conditions, removal of protective groups and the like are the same with the first process and the reaction can be effected by the similar way.

In this connection, the starting compound (VI) can easily be obtained by the aforementioned amidation reaction or a cyclization reaction which will be described later.

Third process (amidation C)

$R^8$—COOH   +
(VII)
or a reactive derivative thereof

-continued
Third process (amidation C)

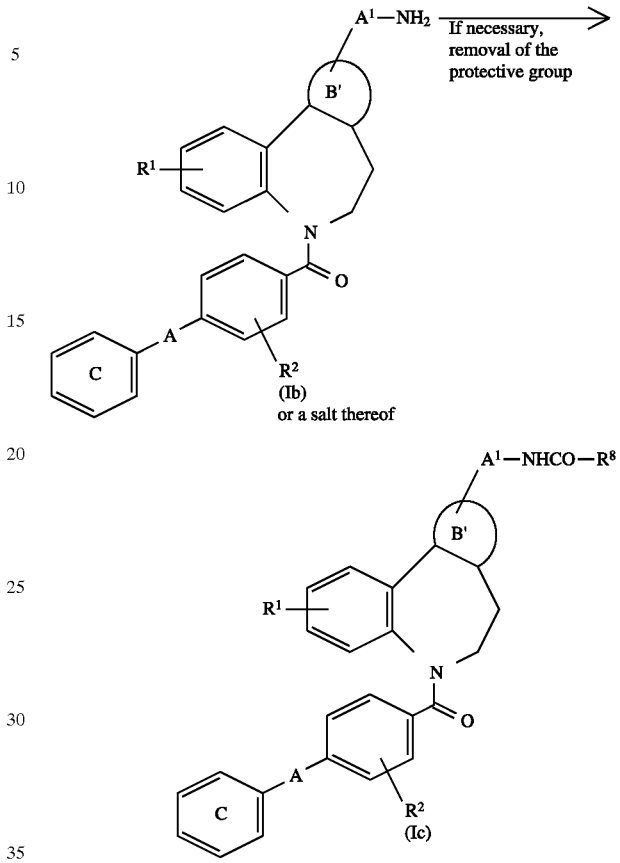

(In the above formulae, $R^1$, $R^2$, ring C and A have the same respective meanings as described in the foregoing, and ring B' is the same as ring B except that one hydrogen atom or substituent is removed, $R^8$ is a lower alkyl group which may optionally be substituted by an amino or mono or di lower alkylamino group that may optionally have a protective group, and $A^1$ is a single bond or a lower alkylene group.)

The compound (Ic) as one of the compounds of the present invention, in which a substituted or unsubstituted lower alkanoylamino group is located on the 5-membered ring, can be produced by subjecting the corresponding carboxylic acid (VII) which may optionally have a protective group, or a reactive derivative thereof, and the corresponding amine (Ib) which may optionally have a protective group, or a salt thereof, to amidation reaction in the usual way and by, if necessary, removing the protective group.

Types of the reactive derivatives, reaction conditions, removal of protective groups and the like are the same with the first process and the reaction can be effected by the similar way.

In addition, a compound in which a substituted or unsubstituted aminocarbonyl group is located on the 5-membered ring or another compound in which —NHCO— or —CONH— is located on the ring C can also be produced in the same manner as in the first process.

Fourth process (cyclization)

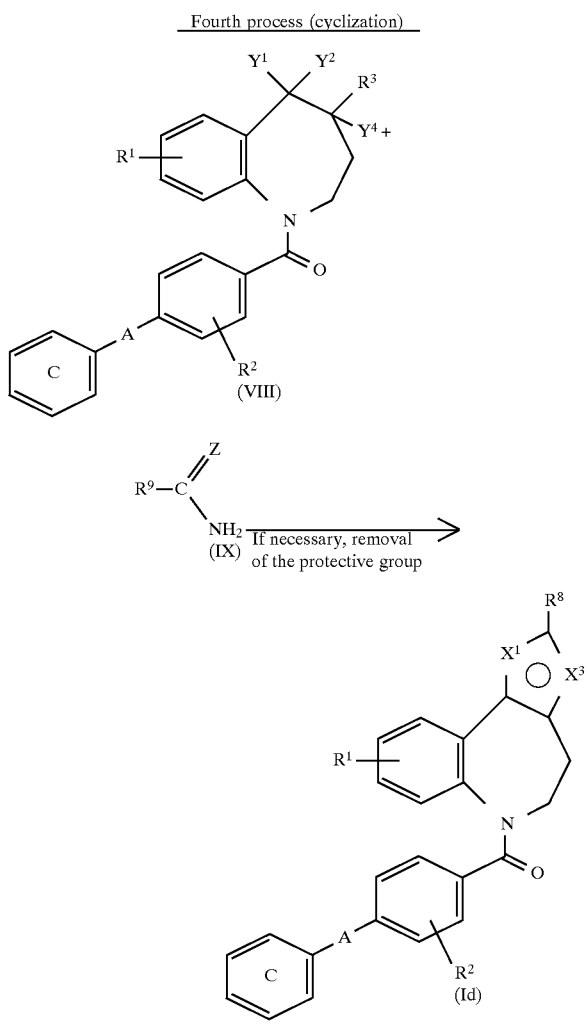

(In the above formulae, $R^1$, $R^2$, ring C, A, $X^1$ and $X^3$ have the same respective meanings as described in the foregoing, and one of $Y^1$ and $Y^2$, and $Y^3$ and $Y^4$ form an oxo group (=O) in combination and the other are a halogen atom and a hydrogen atom

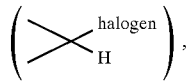

$R^9$ is a hydrogen atom or a subsubstituent, and Z is a group represented by =NH, =O or =S.)

A compound as one of the compounds of the present invention, in which an imidazole ring, an oxazole ring or a thiazole ring is condensed, can be produced by allowing the corresponding haloketone (VIII) which may optionally have a protective group to react with corresponding amidines, guanidines, amides, ureas, thioamides or thioureas represented by formula (IX) and by, if necessary, removing the protective group.

In this reaction, corresponding thioamide and thiourea, amidine and guanidine or carboxilic acid amide and urea derivative may sometimes form a salt with acid. In order to accelerate the reaction, the reaction may be carried out in the presence of an inorganic base such as sodium hydroxide, potassium hydroxide, sodium carbonate, potassium carbonate, sodium bicarbonate, potassium bicarbonate or the like or a salt of a weak acid with a strong base or an organic base such as pyridine, diisopropylethylamine, 1,5-diazabicyclo[4.3.0]non-5-ene or the like. The reaction may preferably be carried out in an inert solvent which includes alcohol solvents such as methyl alcohol, ethyl alcohol, isopropyl alcohol and the like, ether solvents such as ether, tetrahydrofuran, dioxane and the like, acetonitrile, dimethylformamide and dimethylsulfoxide, and at a temperature of from room temperature to reflux temperature of the solvent used. If necessary, the reaction may be carried out under a pressure.

In this instance, oxazoles may sometimes be formed when amidines or guanidins are used in the reaction. In that case, imidazoles can be obtained as the main product by carrying out the reaction in an atmosphere of ammonia gas in the presence of ammonium carbonate, ammonium acetate, formamide or the like.

The starting compound (VIII) to be used in this reaction can be produced, as shown in the following reaction formula, by subjecting p-substituted benzoic acid (X) which may optionally have a protective group, or a reactive derivative thereof, and a benzazepine derivative (XI) which may optionally have a protective group, or a salt thereof, to amidation reaction in the same manner as in the first process and by allowing the resulting product to react with a halogenation agent and, if necessary, removing the protective group at any step. In this connection, a compound in which A of the p-substituted benzoic acid (X) is —(CR$^3$R$^4$)—CONH— can be produced by subjecting the corresponding carboxylic acid (XIII) or a reactive derivative thereof and the corresponding p-aminobenzoic acid (XIV) to amidation reaction in the same manner as in the first process.

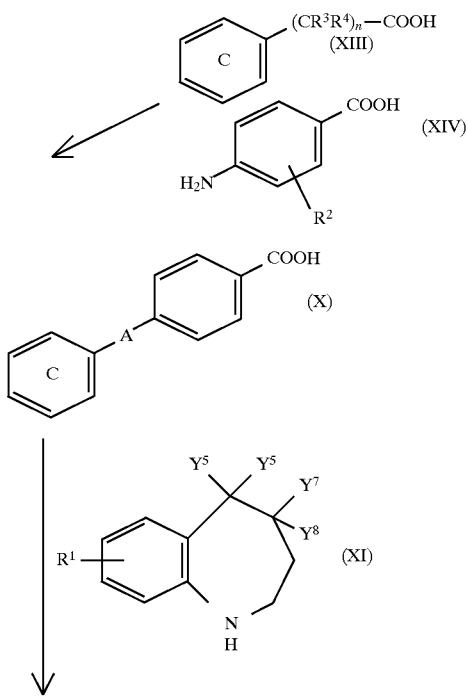

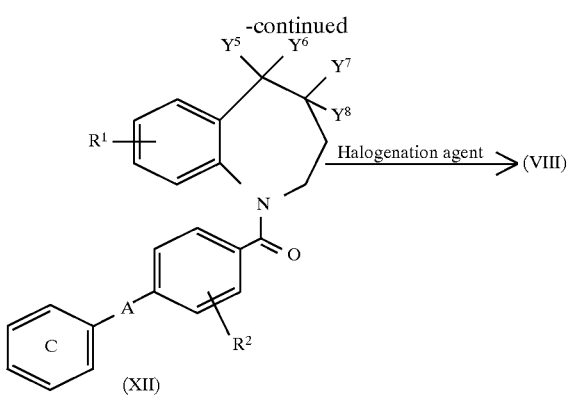

(In the above formulae, $R^1$, $R^2$, $R^3$, $R^4$, ring C and A have the same respective meanings as described in the foregoing, and one of $Y^5$ and $Y^6$, and $Y^7$ and $Y^8$ form an oxo group in combination and the other are both hydrogen atoms

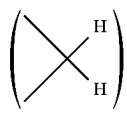

Types of the reactive derivatives, reaction conditions, removal of protective groups and the like in the first step amidation reaction are the same with the first process.

With regard to the halogenation reagent to be used in the halogenation step, any agent conventionally used for the halogenation of saturated cyclic ketones may be used, but preferably a metal reagent such as copper(II) halide (e.g., copper(II) bromide, copper(II) chloride or the like), or a perbromide of pyridine, α-pyrrolidone, quaternary ammonium, dioxane or the like, such as dioxane dibromide, phenyltrimethylammonium tribromide, pyridinium hydrobromide perbromide, pyrrolidone hydrotribromide or the like, as well as a halogen itself such as chlorine, bromine or the like or a hydrohalogenic acid such as hydrochloric acid, hydrobromic acid or the like.

Using a metal reagent or a perbromide, the reaction of the compound (XII) with this halogenation reagent is advantageously carried out generally in an inert solvent selected, for example, from halogenated hydrocarbons such as dichloromethane, chloroform, carbon tetrachloride and the like, ether solvents such as ether, tetrahydrofuran, dioxane and the like, alcohol solvents such as methyl alcohol, ethyl alcohol and the like, aromatic hydrocarbon solvents such as benzene, toluene, xylene and the like, acetic acid, ethyl acetate, water or a mixed solvent thereof, and at room temperature or with heating, if necessary in the presence of a small amount of catalyst such as a hydrogen halide or the like.

The compound of interest can also be obtained by allowing the compound (XII) to react with a halogen itself as the halogenation agent in an inert solvent such as a halogenated hydrocarbon (e.g., dichloromethane, chloroform, carbon tetrachloride and the like) and ethylene glycol, acetic acid and the like, or by allowing the compound (XII) to react with a hydrohalogenic acid as the halogenation agent in its acidic solution or in a basic solution such as a sodium hydroxide aqueous solution. In that case, the reaction may be carried out at a temperature in the range of preferably from −30° C. to reflux temperature of the solvent used.

Although a process for the synthesis of a compound in which an imidazole ring, an oxazole ring or a thiazole ring is condensed has been described in the above, a compound in which an oxadiazole ring, a thiadiazole ring or a triazole ring is condensed can be produced by a conventional process shown by the following reaction formula.

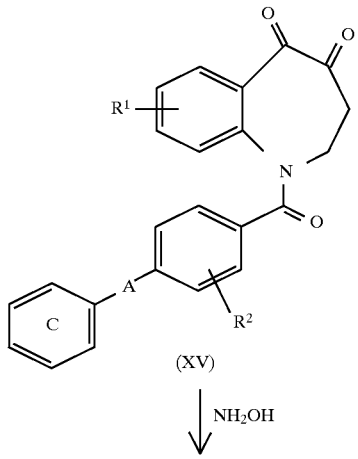

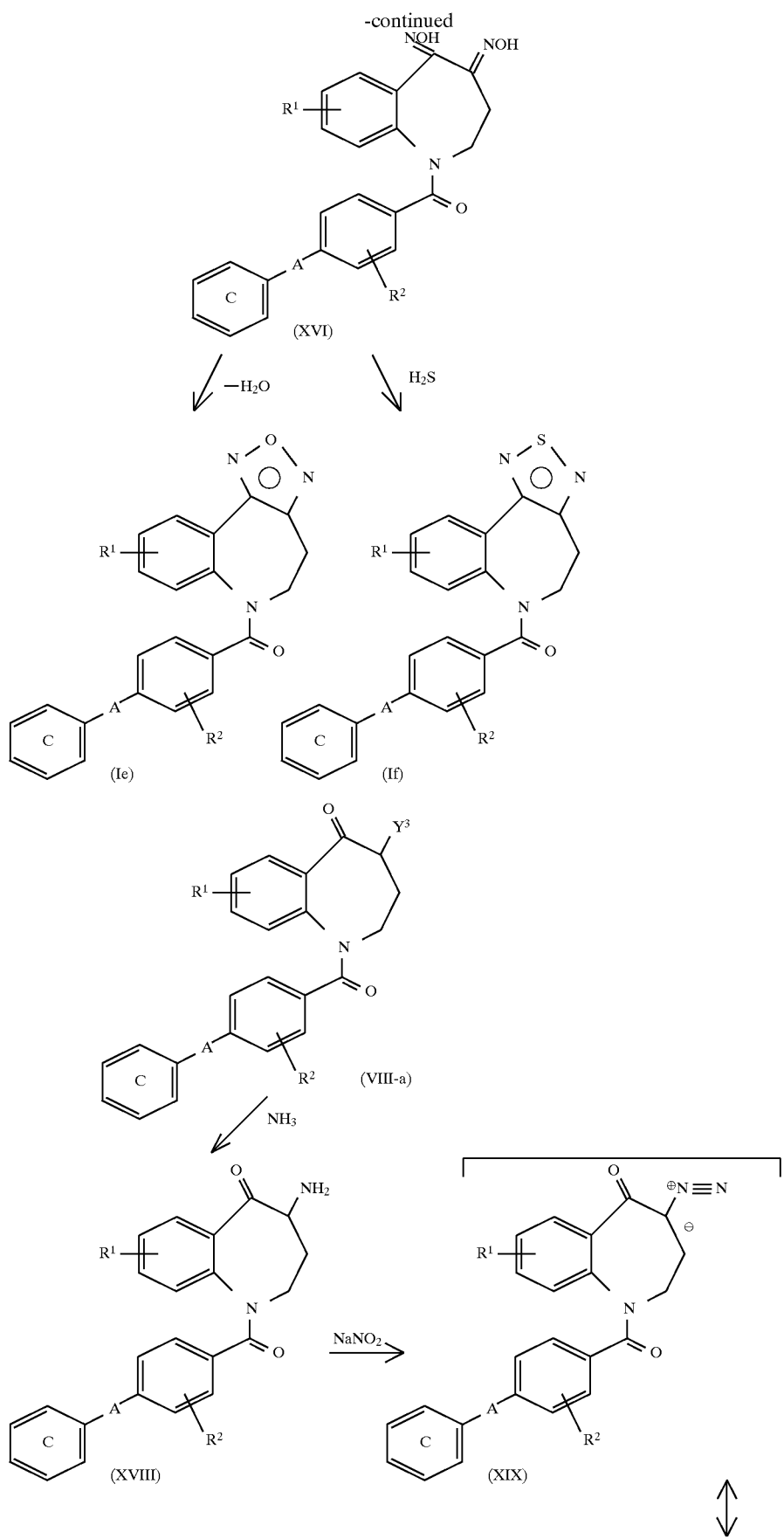

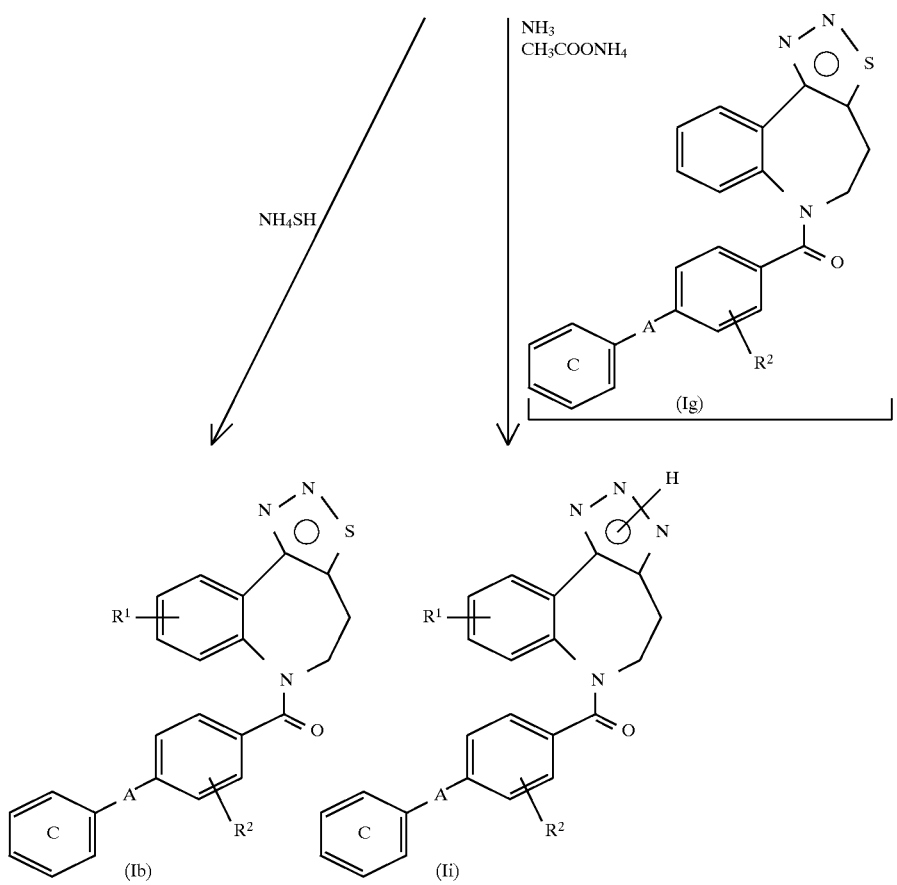

(In the above formulae, $R^1$, $R^2$, ring C and A have the same respective meanings as described in the foregoing, and $Y^9$ is a halogen atom.)

That is, the compound (Ie) in which 1,2,5-oxadiazole ring is condensed and the compound (If) in which 1,2,5-thiadiazole ring is condensed can be produced by allowing a benzazepinedione derivative to react with hydroxylamine hydrochloride in the presence of a base such as sodium acetate or the like to obtain the dioxime compound (XVI) and dehydrating the resulting compound with heating in the presence of a dehydrating agent or treating the compound with hydrogen sulfide. Each reaction step can be effected by conventional means.

On the other hand, the compound (Ig) in which 1,2,3-oxadiazole ring is condensed can be produced by treating the compound (VIIIa) with ammonia and treating the resulting compound (XVIII) with a diazotation agent such as sodium nitrite. That is, the compound (Ig) is in the equilibrium state with the diazo compound (XIX). Also, the compound (Ih) in which 1,2,3-oxadiazole ring is condensed and the compound (Ii) in which 1,2,3-triazole ring is condensed can be produced by allowing the diazo compound (XIX), or the compound (Ig), to react with ammonium hydrosulfide or with ammonia and ammonium acetate. Each of these reaction steps can be effected by conventional means.

The starting compound (XV) can easily be obtained in the same manner as the aforementioned amidation method for the production of compound (XII) from compound (XI), and the other starting compound (VIII-a) can easily be obtained by the method described in the foregoing.

When a haloketone compound having different positions for an oxo group and a halogen atom is used as the starting compound instead of the compound (VIII-a), compounds in which 1,2,3-oxadiazole ring and 1,2,3-thiadiazole ring are condensed at different positions can be produced.

Fifth process (mutual conversion of substituents on the aromatic carbon ring)

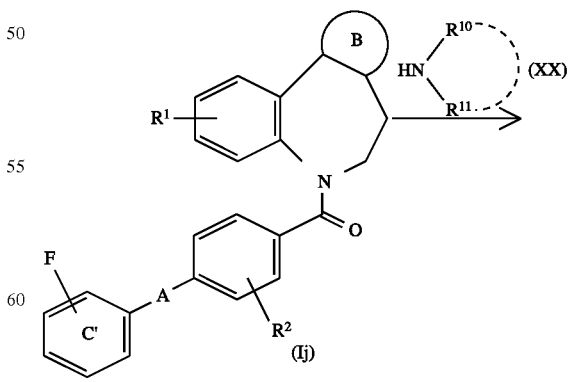

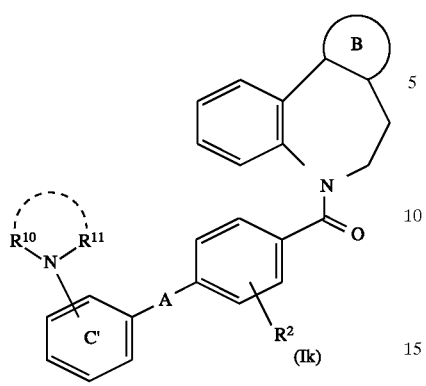

(In the above formulae, $R^1$, $R^2$, ring B and A have the same respective meanings as described in the foregoing, and ring C' is the same with the ring C except that one hydrogen atom or substituent is removed, $R^{10}$ and $R^{11}$ may be the same or different from each other and each represents a hydrogen atom, a lower alkyl group, a protective group or an amidino group, provided that $R^{10}$ and $R^{11}$ may be combined with the adjacent nitrogen atom to form a hetero ring which may optionally be substituted.)

A compound of the present invention in which its aromatic carbon ring has a substituent can be produced by selecting the corresponding starting compound and repeating the aforementioned process but, when the substituent on the aromatic carbon ring contains a characteristic functional group, it can be produced by mutual conversion such as substituent introduction or substitution on the aromatic carbon ring.

For example, the compound (Ik) which contains at least one amine-type substituent as a substituent on the ring C can also be produced by allowing the fluorine compound (Ij) which has —CO— or —C≡N on the adjacent position when A is a single bond or —CONH— to react with ammonia, a corresponding amine, a corresponding cyclic imine or guanidine.

Conventional N-alkylation method can be applied to this process. That is, although the reaction progresses in the absence of solvent, the reaction may be carried out generally in an inert organic solvent selected, for example, from dimethylformamide, dimethylsulfoxide, aromatic hydrocarbons such as benzene, toluene, xylene and the like, halogenated hydrocarbons such as dichloromethane, dichloroethane, chloroform and the like and alcohols such as methyl alcohol, ethyl alcohol, isopropyl alcohol and the like. In order to effect smooth progress of the reaction, it may sometimes be advantageous to carry out the reaction in the presence of an inorganic base such as sodium hydride, potassium carbonate, sodium carbonate or the like. This reaction is generally carried out at room temperature, with heating or at reflux temperature.

This conversion method to form an amine-type substituent on the aromatic carbon ring can also be applied to the case in which conversion into an amine-type substituent as $R^2$ is carried out.

Sixth process (mutual conversion of substituents on the hetero ring)

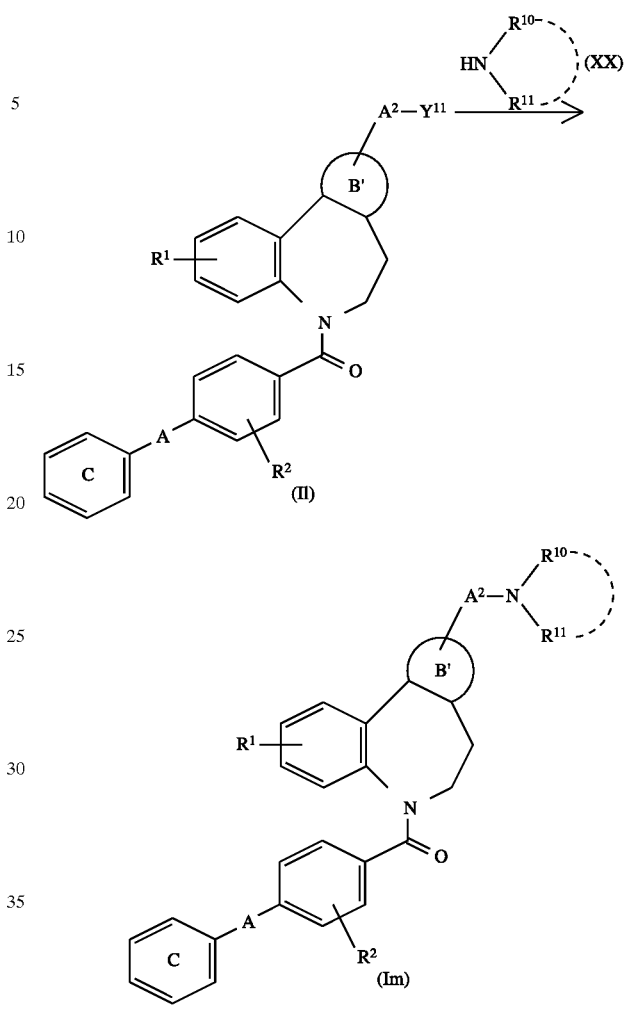

(In the above formulae, $R^1$, $R^2$, ring B', A, ring C, $R^{10}$ and $R^{11}$ have the same respective meanings as described in the foregoing, and $A^2$ is a single bond or a lower alkylene group and $Y^{11}$ is a halogen atom, an organic sulfonic acid residue or, when A is a single bond, an alkoxy or alkylthio group.

Mutual conversion of substituents on the 5-membered hetero ring can be made more easily than the case of the aromatic ring. For example, the compound (Im) which contains at least one amine-type substituent on its hetero ring can be produced by allowing the corresponding halide or sulfonate or, when A is a single bond, ether or the thioether compound (Il) to react with an amine compound (XX).

Examples of the organic sulfonic acid residue include alkanesulfonic acid residues such as methanesulfonyloxy group, ethanesulfonyloxy group and the like and aromatic sulfonic acid residues such as benzenesulfonyloxy group, toluenesulfonyloxy group (especially p) and the like.

The reaction can be effected by almost the same manner as in the case of the fifth process.

In this instance, the mutual conversion into amine substituent on the hetero ring can be used as a process in which an N-substituted compound is produced by allowing an imino nitrogen-containing hetero ring-consended compound to react with the corresponding halide or sulfonate such as a lower alkyl halide or a lower alkyl sulfonate.

Other processes

Although only amidation, cyclization and amine-type substituent introduction have been described in the foregoing, the compound of the present invention can be synthesized by various conventional means because the inventive compound contains various characteristic functional groups.

For example, a compound having a carboxyl group can be produced by hydrolyzing its corresponding ester; an ester compound can be produced by esterificating its corresponding carboxylic acid; alcohol, phenol, mercaptan and thiophenol compounds can be produced by hydrolyzing ether and thioether compounds; and ether and thioether compounds can be produced by allowing corresponding alcohol, phenol, mercaptan and thiophenol-compounds to react with the corresponding halides such as alkyl halides.

The reaction products obtained by the above processes are isolated and purified in the form of free compounds, salts thereof, hydrates thereof or various solvates thereof. Salts can be produced by usual salt forming reactions.

Isolation and purification are carried out by applying usual chemical operations such as extraction, concentration, distillation, crystallization, filtration, recrystallization and various types of chromatography.

As described in the foregoing, isomers such as racemates, optically active substances, diastereoisomers and the like are present alone or as a mixture with respect to the compound of the present invention. Racemic compound can be made into stereochemically pure isomer by the use of a proper starting compound or by means of conventional racemic resolution (for example, a method in which a racemic compound is made into a diastereoisomer salt with a usual optically active acid (tartaric acid or the like) and then subjected to optical resolution). Also, a mixture of diastereoisomers can be separated by conventional means such as fractional crystallization, chromatography and the like.

INDUSTRIAL APPLICABILITY

Compounds of the present invention and salts thereof show excellent antagonism on arginine vasopressin $V_1$ and/or $V_2$ receptor. That is, the compounds of the present invention include a compound which shows strong antagonism on both $V_1$ and $V_2$ receptors, a compound which selectively shows excellent antagonism on $V_1$ receptor and a compound which selectively shows excellent antagonism on $V_2$ receptor.

Particularly preferred is the compound which shows strong antagonism on both $V_1$ and $V_2$ receptors.

The compounds of the present invention are excellent in oral absorption and show proper prolonged action because of its stability to metabolism in the living body.

In consequence, on the basis of these functions, the compounds of the present invention show water diuresis action, urea excretion enhancing action, factor VIII secretion inhibiting action, vasodilation action, cardiac function accelerating action, mesangial cell contraction inhibiting action, mesangial cell proliferation inhibiting action, liver gluconeogenesis inhibiting action, platelet aggregation inhibiting action, aldosterone secretion inhibiting action, endotheline production inhibiting action, central blood pressure controlling action, renin secretion controlling action, memory controlling action, thermoregulation action, prostaglandin production controlling action and the like, and are useful as characteristic water diuretics, urea excretion enhancers, vasodilators, hypotensive agents, agents used to treat heart failure and renal failure and blood coagulation inhibitors, and are effective for the prevention and treatment of heart failure, hyponatremia, syndrome of inappropriate vasopressin secretion (SIADH), hypertension, renal diseases (nephrosis, nephritis, diabetic nephropathy, chronic or acute renal failure), edema, brain edema, ascites, hepatic cirrhosis, hypokalemia, water metabolism disorder, diabetes, various ischemic diseases, cerebrovascular disease, cyclothymic failure, gastric ulcer, nausea, vomiting, syncope, renal function disorder and the like and for the alleviation of sequelae of cerebral infarction, intracerebral bleeding and the like.

Usefulness of the compounds of the present invention was confirmed by the following tests.

(1) $V_1$ receptor binding assay

A rat liver membrane sample was prepared in accordance with the method of Nakamura et al. (*J. Biol. Chem.*, 258, 9283 (1983)), and [$^3$H]-Arg-vasopressin (2 nM, specific activity=75.8 Ci/mmol), 70 μg of the membrane sample and each drug to be tested ($10^{-8}$ to $10^{-4}$M) were incubated at 30° C. for 30 minutes in 250 μl of 100 mM Tris-HCl buffer (pH 8.0) containing 5 mM magnesium chloride, 1 mM ethylenediaminetetraacetic acid (EDTA) and 0.1% bovine serum albumin (BSA). Thereafter, the incubation solution was sucked off using a cell harvester and free ligand and excess buffer were removed by passing the reaction mixture through a glass filter (GF/B), thereby trapping receptor-bound labeled ligand on the glass filter. The glass filter was taken out, thoroughly dried and then mixed with a liquid scintillation cocktail, and the amount of the membrane-bound [$^3$H]-vasopressin was measured using a liquid scintillation counter to calculate the inhibition ratio by the following formula.

$$\text{Inhibition ratio (\%)} = 100 - \frac{C_1 - B_1}{C_0 - B_1} \times 100$$

$C_1$: amount of [$^3$H]-vasopressin bound to the membrane in the coexistence of known amount of each drug to be tested and [$^3$H]-vasopressin $C_0$: amount of [$^3$H]-vasopressin bound to the membrane when the drug to be tested was not added $B_1$: amount of [$^3$H]-vasopressin bound to the membrane in the presence of excess vasopressin ($10^{-6}$M)

Concentration of the drug to be tested which gives 50% inhibition ratio by the above calculation was defined as $IC_{50}$ and used in the following formula to calculate the binding affinity of nonradioactive ligand, namely the dissociation constant (Ki).

$$Ki = \frac{IC_{50}}{1 + [L]/KD}$$

[L]: concentration of radioactive ligand

KD: dissociation constant calculated from Scatchard plot

Negative logarithm of the thus calculated value was used as pKi value. The results are shown in Table 1.

(2) $V_2$ receptor binding assay

A rabbit renal medulla membrane sample was prepared in accordance with the method of Campbell et al. (*J. Biol. Chem.*, 247, 6167 (1972)), and [$^3$H]-Arg-vasopressin (2 nM, specific activity=75.8 Ci/mmol), 100 μg of the membrane sample and each drug to be tested ($10^{-8}$ to $10^{-4}$M) were subjected to the assay in the same manner as the case of the aforementioned $V_1$ receptor binding assay and the pKi values were calculated in the same manner. The results are shown in Table 1.

Compounds of the present invention show excellent arginine vasopressin antagonism. For example, the compounds of Examples 17, 18(2), 20, 21, 23 and 37 showed excellent antagonisms on both $V_1$ and $V_2$ receptors, which were markedly strong even in comparison with a $V_2$ receptor antagonist compound OPC-31260 and a $V_1$ receptor antagonist compound OPC-21268 which are under development as arginine vasopressin antagonists (cf. Table 1).

TABLE 1

Antagonism on arginine vasopressin $V_1$ and $V_2$ receptors

| Example No. | Binding activity on arginine vasopressin $V_1$ receptor (pki) | Binding activity on arginine vasopressin $V_2$ receptor (pki) |
|---|---|---|
| 1 | 8.33 | 7.21 |
| 2 | 8.82 | 8.25 |
| 4 | 8.36 | 8.69 |
| 6 | 7.95 | 8.62 |
| 8 | 7.74 | 8.25 |
| 10 | 8.61 | 8.59 |
| 12 | 8.52 | 8.01 |
| 15 | 8.91 | 8.93 |
| 17 | 9.04 | 9.11 |
| 18(1) | 8.37 | 8.59 |
| 18(2) | 9.05 | 8.83 |
| 20 | 9.18 | 9.04 |
| 21 | 8.74 | 8.42 |
| 22 | 8.11 | 8.07 |
| 23 | 8.91 | 8.98 |
| 24 | 7.77 | 8.64 |
| 27 | 8.21 | 7.23 |
| 37 | 9.49 | 9.30 |
| 38 | 8.24 | 7.31 |
| Comparative compound (1)* | 6.71 | 8.01 |
| Comparative compound (2)** | 7.85 | 4.29 |

*OPC-31260 (WO 9105549, compound of Example 408, hydrochloride)

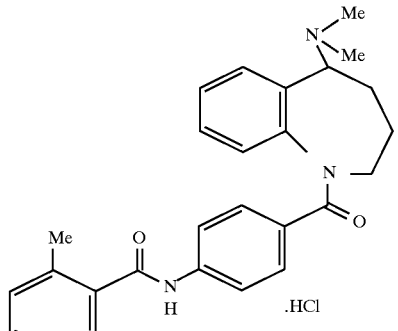

**OPC-21268 (EP 0382185, compound of Example 141)

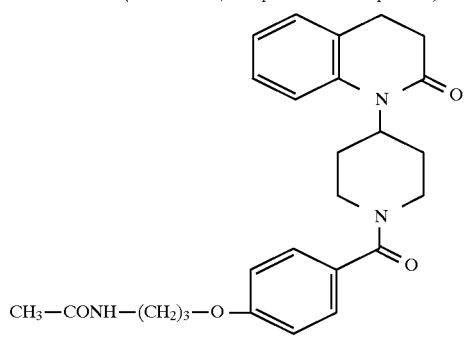

(3) $V_1$ antagonism in conscious rats (oral administration)

$V_1$ antagonism was examined using male Wister rats (body weight, 300 to 320 g) each of which has been subjected, 2 to 3 days before the test, to cannulation into the left carotid for the measurement of blood pressure and into the left jugular for the administration of arginine vasopressin (AVP). Blood pressure was measured under no anesthesia from the carotid cannula via a pressure transducer. Each compound to be tested was suspended in 0.5% methylcellulose aqueous solution and orally administered in a dose of 1 or 10 mg/kg.

Increase in the diastolic blood pressure caused by the intravenous administration of 30 mU/kg of AVP before the administration of a compound to be tested was defined as 100%, and increase in the blood pressure caused by the intravenous administration of 30 mU/kg of AVP was measured periodically during a period of from 30 minutes after the test compound administration to 8 hours after the test compound administration to calculate the inhibition ratio of pressure increase by the test compound, namely $V_1$ antagonism of the test compound.

Pressure increase by AVP was repressed to 50% or below during a period of from 30 minutes after the test sample administration to 6 hours after the test compound administration by the administration of 1 mg/kg of each of the compounds of Examples 18(2), 21 and 23, thus showing prolonged action of the inventive compounds. On the other hand, oral administration of OPC-21268 in a dose of 10 mg/kg which was ten times larger than the dose of these inventive compounds was effective in repressing the pressure increase by AVP to 50% or lower level but during a period of only from 30 minutes to 1 hour after the administration, and the pressure increase by AVP returned to the 100% level 4 hours after the administration, thus showing disappearance of the $V_1$ antagonism.

On the basis of the above results, it was confirmed that the $V_1$ antagonism of the compounds of the present invention by their oral administration into conscious rats is strong and long-acting in comparison with OPC-21268.

(4) $V_2$ antagonism (water diuresis) in conscious rats (oral administration)

Each compound to be tested was suspended in 0.5% methylcellulose aqueous solution and orally administered in a dose of 3 mg/kg to male Wister rats (body weight, 270 to 300 g) which had been subjected to fasting with no water for 16 to 20 hours. Using a metabolic cage, urine samples were collected just after the administration of each test sample and until 4 hours after the administration to measure the amount of urine.

In the test group in which each of the compounds of Examples 18(2), 20, 21 and 23 was administered, the amount of urine collected during a period of from just after the administration to 2 hours after the administration was 47 to 95 times larger than that in the solvent-administered group, and the amount of urine collected during a period of from 2 hours to 4 hours after the administration was 8 to 10 times larger than that in the solvent-administered group, thus showing prolonged water diuresis enhancing effect. On the other hand, in the OPC-31260-administered group, the amount of urine collected during a period of from just after the administration to 2 hours after the administration was 11 times larger than that in the solvent-administered group, but the amount of urine collected during a period of from 2 hours to 4 hours after the administration was almost the same as that in the solvent-administered group, thus showing disappearance of the water diuresis enhancing effect.

On the basis of the above results, it was confirmed that the water diuresis enhancing effect of the compounds of the present invention by their oral administration into conscious rats is strong and long-acting in comparison with OPC-31260.

A pharmaceutical composition which contains as its active ingredient one or more of the compounds of the general formula (I) and pharmaceutically acceptable salts thereof is made into various dosage forms such as tablets, powders, fine granules, granules, capsules, pills, solutions, injections, suppositories, ointments, plasters and the like, making use of conventionally used pharmaceutical carriers, excipients and other additives, and administered orally or parenterally.

Clinical dose of the compound of the present invention to human may optionally be decided taking symptoms, weight, age, sex and the like of each patient into consideration, but it may generally be 0.1 to 500 mg per adult per day in the case of oral administration, and the daily dose may be used in one portion or divided portions. Since the dose varies under various conditions, sufficient effects may be obtained in some cases with smaller dose than the above range.

As solid compositions for oral administration according to the present invention, tablets, powders, granules and the like may be used. In such solid compositions, one or more of active ingredient(s) may be mixed with at least one inert diluent such as lactose, mannitol, glucose, hydroxypropylcellulose, fine crystalline cellulose, starch, polyvinyl pyrrolidone or magnesium aluminate metasilicate. In accordance with the conventional way, the composition may contain other additives than the inert diluent, which include a lubricant such as magnesium stearate, a disintegrating agent such as fibrin calcium glycolate, a stabilizing agent such as lactose and a solubilizing agent or a solution adjuvant such as glutamic acid or aspartic acid. If necessary, tablets or pills may be coated with a film of gastric or enteric substance such as sucrose, gelatin, hydroxypropylcellulose, hydroxypropylmethylcellulose phthalate or the like.

Liquid compositions for use in oral administration include pharmaceutically acceptable emulsions, solutions, suspensions, syrups, elixirs and the like which contain conventionally used inert diluents such as purified water and ethanol. In addition to the inert diluents, such compositions may also contain adjuvants such as a solubilizing agent or a solution adjuvant, a moistening agent, a suspending agent and the like, as well as a sweetening agent, a flavoring agent, an aromatic agent and an antiseptic agent.

Injections for use in parenteral administration include aseptic aqueous or non-aqueous solutions, suspensions and emulsions. Examples of diluent for use in aqueous solutions and suspensions include distilled water for injection use and physiological saline. Examples of non-aqueous diluent for use in solutions and suspensions include plant oils such as propylene glycol, polyethylene glycol, olive oil and the like, alcohols such as ethanol and the like and Polysorbate 80 (trade name). Such compositions may also contain additives such as a tonicity agent, an antiseptic agent, a moistening agent, an emulsifying agent, a dispersing agent, a stabilizing agent (lactose for example), a solubilizing agent or a solution adjuvant and the like. These compositions are sterilized by bacterial filtration through a bacteria-retaining filter, bactericide blending or irradiation. Alternatively, an aseptically produced solid composition may be used by dissolving it in sterile water or a sterile injection solvent prior to its use.

BEST MODE FOR CARRYING OUT THE INVENTION

Thus, the compounds of the present invention and their production processes have been described which will be further illustrated in detail with reference to the following examples. The present invention, however, is not limited by these examples. Since some of the starting compounds of the present invention are novel compounds, examples of their production processes are shown as Reference Examples.

REFERENCE EXAMPLE 1

A 3.32 g portion of 2,3,4,5-tetrahydro-1H-1-benzazepin-5-one and 4.31 ml of triethylamine were dissolved in 33 ml of dichloromethane and, with stirring on an ice bath, 4.59 g of p-nitrobenzoyl chloride was added to the resulting solution. The reaction solution was stirred at room temperature for additional 60 minutes. The reaction solution was then mixed with a saturated sodium bicarbonate aqueous solution and subjected to phase separation. The dichloromethane layer was separated and washed with a 1N hydrochloric acid aqueous solution and a saturated sodium chloride aqueous solution once for each. The thus washed layer was dried over anhydrous magnesium sulfate and then concentrated under a reduced pressure.

The thus obtained residue was recrystallized from methyl alcohol to obtain 5.68 g of 1-(4-nitrobenzoyl)-2,3,4,5-tetrahydro-1H-1-benzazepin-5-one.
Physicochemical properties
$^1$H-NMR ($\delta$ ppm in CDCl$_3$, TMS internal standard): 2.17 (2H, m), 2.90 (total 3H), 4.1 (1H), 6.7 (1H, m), 7.2–7.55 (total 4H), 7.78–8.15 (total 3H).
MS (FAB): 311 (M$^+$+1).

REFERENCE EXAMPLE 2

A 19.2 g portion of 1-(4-nitrobenzoyl)-2,3,4,5-tetrahydro-1H-1-benzazepin-5-one was dissolved in a mixed solvent consisting of 200 ml of dimethylformamide and 100 ml of methyl alcohol, and 3 ml of Raney nickel was added to the resulting solution to carry out hydrogenation at normal pressure. After completion of the hydrogen absorption, the reaction solution was filtered and concentrated. The thus obtained residue was dissolved in dichloromethane and then washed with a saturated sodium bicarbonate aqueous solution. The resulting dichloromethane layer was dried over anhydrous magnesium sulfate and then concentrated under a reduced pressure. The thus obtained residue was recrystallized from methyl alcohol to obtain 15.5 g of 1-(4-aminobenzoyl)-2,3,4,5-tetrahydro-1H-1-benzazepin-5-one.
Physicochemical properties
$^1$H-NMR ($\delta$ ppm in CDCl$_3$, TMS internal standard): 2.15 (2H, m), 2.90 (2H, m), 4.05 (2H), 6.45 (2H, d), 6.77 (1H, m), 7.0–7.35 (total 4H), 7.88 (1H, m).
MS (FAB): 281 (M$^+$+1).

REFERENCE EXAMPLE 3

With stirring at −15° C., 2.25 ml of oxalyl chloride and a catalytically effective amount of N,N-dimethylformamide were added to a solution which had been prepared by dissolving 3.4 g of o-phenylbenzoic acid in 34 ml of dichloromethane, and the resulting mixture was warmed up to room temperature spending 2 hours and stirred for additional 2 hours. The reaction solution was concentrated under a reduced pressure and subjected to azeotropic treatment three times with dichloromethane. The thus obtained residue was dissolved in 34 ml of dichloromethane and, with stirring on an ice bath, the resulting solution was dropwise added to 40 ml of a dichloromethane solution containing 4.0 g of 1-(4-aminobenzoyl)-2,3,4,5-tetrahydro-1H-1-benzazepin-5-one and 3.0 ml of triethylamine. The reaction solution was warmed up to room temperature and the stirring was continued for 120 minutes. The resulting reaction solution was mixed with a saturated sodium bicarbonate aqueous solution and subjected to phase separation. The dichloromethane layer was separated, dried over magnesium sulfate and then concentrated. The thus obtained residue was recrystallized from toluene to obtain 5.82 g of 2-phenyl-4'-[(5-oxo-2,3,4,5-tetrahydro-1H-1-benzazepin-1-yl)carbonyl]benzanilide.
Physicochemical properties
$^1$H-NMR ($\delta$ ppm in CDCl$_3$, TMS internal standard): 2.23 (2H, m), 2.87 (2H, m), 4.1 (2H), 6.75 (1H, m), 6.8–7.7 (total 15H), 7.85 (1H, m).
MS (FAB): 461 (M$^+$+1).

REFERENCE EXAMPLE 4

Using o-(4-methylphenyl)benzoic acid and 1-(4-aminobenzoyl)-2,3,4,5-tetrahydro-1H-1-benzazepin-5-one as starting materials, the procedure of Reference Example 3 was repeated to obtain 2-(4-methylphenyl)-4'-[(5-oxo-2,3,4,5-tetrahydro-1H-1-benzazepin-1-yl)carbonyl]benzanilide.

Physicochemical properties $^1$H-NMR (δ ppm in CDCl$_3$, TMS internal standard): 2.18 (2H, m), 2.35 (3H, s), 2.88 (2H, m), 4.1 (2H), 6.72 (1H, m), 6.85–7.7 (total 13H), 7.85 (2H).

MS (FAB): 475 (M$^+$+1).

EXAMPLE 1

After dissolving 500 mg of 2-phenyl-4'-[(5-oxo-2,3,4,5-tetrahydro-1H-1-benzazepin-1 -yl)carbonyl]benzanilide in a mixed solvent consisting of 15 ml of chloroform and 1.5 ml of ethyl acetate, the resulting solution was mixed with 560 mg of copper(II) bromide and subjected to 3 hours of heating under reflux with vigorous stirring. After cooling down the reaction solution to room temperature, insoluble materials were removed by filtration and the resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 12 ml of ethyl alcohol, and the resulting solution was mixed with 100 mg of thiourea and subjected to 3 hours of heating under reflux. During the reflux, colorless crystals were precipitated. After cooling the reaction solution on an ice bath, crystals were collected by filtration and washed with a small volume of ethyl alcohol to obtain 540 mg of 4'-[(2-amino-5,6-dihydro-4H-thiazolo[5,4-d][1]benzazepin-6-yl)carbonyl]-2-phenylbenzanilide hydrobromate.

Physicochemical properties

Melting point: >250° C.

Elemental analysis data (C$_{31}$H$_{24}$N$_4$O$_2$S · HBr)

|  | C(%) | H(%) | N(%) | S(%) | Br(%) |
|---|---|---|---|---|---|
| Calc.: | 62.31 | 4.22 | 9.38 | 5.37 | 13.37 |
| Found: | 62.39 | 4.42 | 9.18 | 5.21 | 13.51 |

$^1$H-NMR (δ ppm in DMSO-d$_6$, TMS internal standard): 2.8–3.4 (total 3H), 5.0 (1H), 6.6–7.8 (total 16H), 8.16 (1H, m), 10.27 (1H, s).

MS (FAB): 517 (M$^+$+1).

EXAMPLE 2

After dissolving 500 mg of 2-phenyl-4'-[(5-oxo-2,3,4,5-tetrahydro-1H-1-benzazepin-1-yl)carbonyl]benzanilide in a mixed solvent consisting of 15 ml of chloroform and 1.5 ml of ethyl acetate, the resulting solution was mixed with 560 mg of copper(II) bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in a mixed solvent consisting of 10 ml of 2-propyl alcohol and 2 ml of methyl alcohol, and the resulting solution was mixed with 155 mg of guanylthiourea and subjected to 6 hours of heating under reflux. During the reflux, colorless crystals were precipitated. After cooling the reaction solution on an ice bath, crystals were collected by filtration and washed with a small volume of cold 2-propyl alcohol. The thus washed crystals were recrystallized from methyl alcohol to obtain 452 mg of 4'-[(2-guanidino-5,6-dihydro-4H-thiazolo[5,4-d][1]benzazepin-6-yl)carbonyl]-2-phenylbenzanilide hydrobromate.

Physicochemical properties

Melting point: >250° C.

$^1$H-NMR (δ ppm in DMSO-d$_6$, TMS internal standard): 2.9–3.5 (total 3H), 4.95 (1H), 6.7–7.8 (total 16H), 8.18 (total 5H), 10.32 (1H, s).

MS (FAB): 559 (M$^+$+1).

EXAMPLE 3

The reaction of Example 1 was repeated except that 470 mg of 2-(4-methylphenyl)-4'-[(5-oxo-2,3,4,5-tetrahydro-1H-1-benzazepin-1-yl)carbonyl]benzanilide was used as the starting material, the resulting reaction solution was concentrated and the thus obtained residue was subjected to phase separation using ethyl acetate and a sodium bicarbonate aqueous solution. The ethyl acetate layer was separated, dried over magnesium sulfate and then concentrated. The thus obtained residue was recrystallized from ethyl acetate to obtain 358 mg of 4'-[(2-amino-5,6-dihydro-4H-thiazolo[5,4-d][1]benzazepin-6-yl)carbonyl]-2-(4-methylphenyl)benzanilide.

Physicochemical properties

Melting point: 161°–163° C.

Elemental analysis data (C$_{32}$H$_{26}$N$_4$O$_2$S)

|  | C(%) | H(%) | N(%) | S(%) |
|---|---|---|---|---|
| Calc.: | 72.43 | 4.94 | 10.56 | 6.04 |
| Found: | 72.32 | 4.85 | 10.52 | 5.78 |

$^1$H-NMR (δ ppm in DMSO-d$_6$, TMS internal standard): 2.27 (3H, s), 3.07 (2H), 5.0 (1H), 6.72 (1H, m), 6.8–7.7 (total 14H), 8.18 (1H, m), 10.29 (1H, s).

MS (FAB): 531 (M$^+$+1).

EXAMPLE 4

Using 400 mg of 2-(4-methylphenyl)-4'-[(5-oxo-2,3,4,5-tetrahydro-1H-1-benzazepin-1-yl)carbonyl]benzanilide as a starting material, the procedure of Example 2 was repeated to obtain 392 mg of 4'-[(2-guanidino-5,6-dihydro-4H-thiazolo[5,4-d][1]benzazepin-6-yl)carbonyl]-2-(4-methylphenyl)benzanilide hydrobromate.

Physicochemical properties

Melting point: >230° C.

Elemental analysis data (C$_{33}$H$_{28}$N$_6$O$_2$S · HBr)

|  | C(%) | H(%) | N(%) | S(%) | Br(%) |
|---|---|---|---|---|---|
| Calc.: | 60.64 | 4.47 | 12.86 | 4.91 | 12.23 |
| Found: | 60.35 | 4.49 | 12.72 | 4.73 | 12.08 |

$^1$H-NMR (δ ppm in DMSO-d$_6$, TMS internal standard): 2.27 (3H, s), 3.30 (total 3H), 6.7–7.8 (total 15H), 7.92 (total 4H), 8.22 (1H, m), 10.29 (1H, s).

MS (FAB): 573 (M$^+$+1).

EXAMPLE 5

After dissolving 400 mg of 2-phenyl-4'-[(5-oxo-2,3,4,5-tetrahydro-1H-1-benzazepin-1-yl)carbonyl]benzanilide in a mixed solvent consisting of 15 ml of chloroform and 2 ml of ethyl acetate, the resulting solution was mixed with 390 mg of copper(II) bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 20 ml of 2-propyl alcohol, and the resulting solution was mixed with 372 mg of 4-imidazolylthioacetamide hydrochloride and subjected to 24 hours of heating under reflux. After cooling down the reaction solution to room temperature, the solvent was distilled off and the resulting residue was mixed with chloroform and a saturated sodium bicarbonate aqueous solution to separate the resulting organic layer which was subsequently washed with water and a saturated sodium chloride aqueous solution, dried over anhydrous magnesium sulfate and then subjected to removal of the solvent by distillation under reduced pressure. The thus obtained residue was subjected to silica gel column chromatography and elution was carried out with chloroform-methyl alcohol (25:1). The resulting eluate in chloroform was mixed with 5 ml of 4N hydrochloric acid-ethyl acetate and the solvent was removed by distillation, and the thus obtained residue was recrystallized from ethyl alcohol-diethyl ether to obtain 262 mg of 4'-[(2-(4-imidazolylmethyl)-5,6-dihydro-4H-thiazolo[5,4-d][1]benzazepin-6-yl)carbonyl]-2-phenylbenzanilide.2HCl.
Physicochemical properties
Melting point: 192°–195° C.

Elemental analysis data ($C_{35}H_{27}N_5O_2S \cdot 2HCl \cdot 1.5H_2O$)

|  | C(%) | H(%) | N(%) | S(%) | Cl(%) |
|---|---|---|---|---|---|
| Calc.: | 61.67 | 4.73 | 10.27 | 4.70 | 10.40 |
| Found: | 61.82 | 4.37 | 10.27 | 4.79 | 10.30 |

$^1$H-NMR (δ ppm in DMSO-$d_6$, TMS internal standard): 3.04 (1H, m), 3.37 (2H, m), 4.56 (2H, s), 5.00 (1H, m), 6.78 (1H, d), 6.90 (2H, d), 7.08 (1H, t), 7.25–7.69 (total 14H), 8.29 (1H, d), 10.35 (1H, s), 14.59 (1H, s).
MS (FAB): 582 ($M^+$+1).

EXAMPLE 6

Using 400 mg of 2-phenyl-4'-[(5-oxo-2,3,4,5-tetrahydro-1H-1-benzazepin-1-yl)carbonyl]benzanilide and 262 mg of 4-(2-methylimidazolyl)thioacetamide hydrochloride, the procedure of Example 5 was repeated to obtain 263 mg of 4'-[[2-[4-(2-methylimidazolyl)methyl]-5,6-dihydro-4H-thiazolo[5,4-d][1]benzazepin-6-yl)carbonyl]-2-phenylbenzanilide.2HCl.
Physicochemical properties
Melting point: 197°–200° C.

Elemental analysis data ($C_{36}H_{29}N_5O_2S \cdot 2HCl \cdot 1.5H_2O$)

|  | C(%) | H(%) | N(%) | S(%) | Cl(%) |
|---|---|---|---|---|---|
| Calc.: | 62.97 | 4.82 | 10.20 | 4.67 | 10.33 |
| Found: | 62.75 | 4.62 | 10.24 | 4.73 | 9.99 |

$^1$H-NMR (δ ppm in DMSO-$d_6$, TMS internal standard): 2.56 (3H, s), 3.05 (1H, m), 3.36 (2H, m), 4.48 (2H, s), 5.00 (1H, m), 6.79 (1H, d), 6.90 (2H, d), 7.09 (1H, t), 7.25–7.58 (total 13H), 8.33 (1H, d), 10.34 (1H, s), 14.20 (1H, s).
MS (FAB): 596 ($M^+$+1).

EXAMPLE 7

Using 400 mg of 2-phenyl-4'-[(5-oxo-2,3,4,5-tetrahydro-1H-1-benzazepin-1-yl)carbonyl]benzanilide and 370 mg of 2-pyridylthioacetamide hydrochloride, the procedure of Example 5 was repeated, and the resulting free base was recrystallized from chloroform-diethyl ether to obtain 300 mg of 4'-[[2-(2-pyridylmethyl)-5,6-dihydro-4H-thiazolo[5,4-d][1]benzazepin-6-yl)carbonyl]-2-phenylbenzanilide.
Physicochemical properties
Melting point: 215°–218° C.

Elemental analysis data ($C_{37}H_{28}N_4O_2S$)

|  | C(%) | H(%) | N(%) | S(%) |
|---|---|---|---|---|
| Calc.: | 74.98 | 4.76 | 9.45 | 5.41 |
| Found: | 74.69 | 4.68 | 9.32 | 5.39 |

$^1$H-NMR (δ ppm in CDCl$_3$, TMS internal standard): 3.10 (2H, m), 3.49 (1H, m), 4.56 (2H, s), 5.17 (1H, dd), 6.66 (1H, d), 6.85 (1H, d), 6.96–7.10 (5H, m), 7.22–7.49 (total 8H), 7.46 (1H, t), 7.53 (1H, t), 7.61 (1H, t), 7.86 (1H, d), 8.42 (1H, d), 8.63 (1H, d).
MS (FAB): 593 ($M^+$+1).

EXAMPLE 8

Using 400 mg of 2-phenyl-4'-[(5-oxo-2,3,4,5-tetrahydro-1H-1-benzazepin-1-yl)carbonyl]benzanilide and 400 mg of 3-pyridylthioacetamide hydrochloride, the procedure of Example 5 was repeated to obtain 100 mg of 4'-[[2-(3-pyridylmethyl)-5,6-dihydro-4H-thiazolo[5,4-d][1]benzazepin-6-yl)carbonyl]-2-phenylbenzanilide hydrochloride as an amorphous solid.
Physicochemical properties
$^1$H-NMR (δ ppm in DMSO-$d_6$, TMS internal standard): 3.03 (1H, m), 3.29 (2H, m), 4.66 (2H, s), 4.99 (1H, d), 6.78 (1H, d), 6.89 (2H, d), 7.08 (1H, t), 7.25–7.58 (total 12H), 8.03 (1H, t), 8.25 (1H, d), 8.60 (1H, d), 8.85 (1H, d), 9.04 (1H, s), 10.32 (1H, s).
MS (FAB): 593 ($M^+$+1).

EXAMPLE 9

Using 400 mg of 2-phenyl-4'-[(5-oxo-2,3,4,5-tetrahydro-1H-1-benzazepin-1-yl)carbonyl]benzanilide and 337 mg of 3-morpholynobutylthioamide hydrochloride, the procedure of Example 5 was repeated and the resulting residue was recrystallized from methyl alcohol-diethyl ether to obtain 360 mg of 4'-[[2-(3-morpholynopropyl)-5,6-dihydro-4H-thiazolo[5,4-d][1]benzazepin-6-yl)carbonyl]-2-phenylbenzanilide hydrochloride.
Physicochemical properties
Melting point: 215°–218° C.

Elemental analysis data ($C_{38}H_{36}N_4O_3S \cdot 2HCl \cdot 1.6H_2O$)

|  | C(%) | H(%) | N(%) | S(%) | Cl(%) |
|---|---|---|---|---|---|
| Calc.: | 62.48 | 5.68 | 7.67 | 4.39 | 9.71 |
| Found: | 62.13 | 5.59 | 7.45 | 4.38 | 9.16 |

$^1$H-NMR (δ ppm in DMSO-$d_6$, TMS internal standard): 2.27 (2H, m), 3.06–3.39 (total 9H), 3.45 (2H, m), 3.85 (1H, m), 3.85 (2H, t), 3.95 (2H, m), 5.00 (1H, m), 6.79 (1H, d), 6.90 (2H, d), 7.08 (1H, t), 7.25–7.57 (total 12H), 8.35 (1H, d), 10.34 (1H, s).
MS (FAB): 629 ($M^+$+1).

EXAMPLE 10

Using 400 mg of 2-phenyl-4'-[(5-oxo-2,3,4,5-tetrahydro-1H-1-benzazepin-1-yl)carbonyl]benzanilide and 300 mg of dimethylaminoethylthioamide hydrochloride and using ethyl alcohol as the reaction solvent, the procedure of Example 5 was repeated and the resulting residue was recrystallized from ethyl acetate-diethyl ether to obtain 300 mg of 4'-[(2-dimethylaminoethylamino-5,6-dihydro-4H-thiazolo[5,4-d][1]benzazepin-6-yl)carbonyl]-2-phenylbenzanilide.2HCl.

Physicochemical properties
Melting point: 187°–190° C.

Elemental analysis data ($C_{35}H_{33}N_5O_2S \cdot 2HCl \cdot 3H_2O$)

|  | C(%) | H(%) | N(%) | S(%) | Cl(%) |
|---|---|---|---|---|---|
| Calc.: | 58.82 | 5.78 | 9.80 | 4.49 | 9.92 |
| Found: | 58.60 | 5.40 | 9.73 | 4.53 | 9.51 |

$^1$H-NMR (δ ppm in DMSO-$d_6$, TMS internal standard): 2.85 (6H, s), 3.02 (2H, m), 3.19 (1H, m), 3.37 (2H, t), 3.76 (2H, m), 4.97 (1H, m), 6.74 (1H, d), 6.93 (2H, d), 7.04 (1H, t), 7.24–7.58 (total 12H), 8.24 (1H, d), 10.35 (1H, s), 10.59 (1H, S).
MS (FAB): 514 ($M^+$+1).

EXAMPLE 11

Using 400 mg of 2-phenyl-4'-[(5-oxo-2,3,4,5-tetrahydro-1H-1-benzazepin-1-yl)carbonyl]benzanilide and 204 mg of dimethylaminothioacetamide hydrochloride, the procedure of Example 5 was repeated to obtain 167 mg of 4'-[(2-dimethylamino-5,6-dihydro-4H-thiazolo(5,4-d][1]benzazepin-6-yl)carbonyl]-2-phenylbenzanilide hydrochloride as an amorphous solid.

Physicochemical properties
$^1$H-NMR (δ ppm in DMSO-$d_6$, TMS internal standard): 3.04 (1H, m), 3.12 (6H, s), 3.29 (2H, d), 4.96 (1H, m), 6.73 (1H, d), 6.92 (2H, d), 7.04 (1H, t), 7.24–7.58 (total 12H), 8.24 (1H, d), 10.33 (1H, s).
MS (FAB): 545 ($M^+$+1).

EXAMPLE 12

Using 400 mg of 2-phenyl-4'-[(5-oxo-2,3,4,5-tetrahydro-1H-1-benzazepin-1-yl)carbonyl]benzanilide and 285 mg of dimethylaminobutylthioamide hydrochloride, the procedure of Example 5 was repeated to obtain 212 mg of 4'-[[2-(3-dimethylaminopropyl)-5,6-dihydro-4H-thiazolo[5,4-d][1]benzazepin-6-yl)carbonyl]-2-phenylbenzanilide hydrochloride as an amorphous solid.

Physicochemical properties
$^1$H-NMR (δ ppm in DMSO-$d_6$, TMS internal standard): 2.19 (2H, m), 2.79 (6H, s), 3.10 (3H, m), 3.18 (2H, t), 3.27 (2H, m), 5.04 (1H, m), 6.77 (1H, d), 6.90 (2H, d), 7.08 (1H, t), 7.25 –7.58 (total 12H), 8.35 (1H, d), 10.33 (1H, s).
MS (FAB): 587 ($M^+$+1).

EXAMPLE 13

Using 400 mg of 2-phenyl-4'-[(5-oxo-2,3,4,5-tetrahydro-1H-1-benzazepin-1-yl)carbonyl]benzanilide and 185 mg of 2-carboxypropanethioamide, the procedure of Example 5 was repeated and the resulting free base was recrystallized from methyl alcohol-diethyl ether to obtain 186 mg of 4'-[(2-methyl-5,6-dihydro-4H-thiazolo[5,4-d][1]benzazepin-6-yl)carbonyl]-2-phenylbenzanilide.

Physicochemical properties
Melting point: 165°–168° C.

Elemental analysis data ($C_{32}H_{25}N_3O_2S \cdot 0.4H_2O$)

|  | C(%) | H(%) | N(%) | S(%) |
|---|---|---|---|---|
| Calc.: | 73.52 | 4.97 | 8.04 | 6.13 |
| Found: | 73.35 | 5.08 | 7.56 | 5.88 |

$^1$H-NMR (δ ppm in DMSO-$d_6$, TMS internal standard): 2.75 (3H, s), 3.07–3.19 (2H, m), 3.55 (1H, m), 5.20 (1H, m), 6.65 (1H, d), 6.85 (2H, d), 6.96–6.99 (3H, m), 7.01–7.85 (total 9H), 8.38 (1H, d), 8.39 (1H, d).
MS (FAB): 516 ($M^+$+1).

EXAMPLE 14

(1) After dissolving 461 mg of 2-phenyl-4'-[(5-oxo-2,3,4,5-tetrahydro-1H-1-benzazepin-1-yl)carbonyl]benzanilide in a mixed solvent consisting of 14 ml of chloroform and 1.4 ml of ethyl acetate, the resulting solution was mixed with 560 mg of copper(II) bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 12 ml of 2-propyl alcohol, and the resulting solution was mixed with 220 mg of phthalimidothioacetamide and subjected to 6 hours of heating under reflux. During the reflux, colorless crystals were precipitated. After cooling the reaction solution on an ice bath, crystals were collected by filtration and washed with a small volume of cold 2-propyl alcohol to obtain 410 mg of 4'-[(2-phthalimidomethyl-5,6-dihydro-4H-thiazolo[5,4-d][1]benzazepin-6-yl)carbonyl]-2-phenylbenzanilide.

Physicochemical properties
$^1$H-NMR (δ ppm in CDCl$_3$, TMS internal standard): 2.8–3.8 (total 3H), 5.21 (2H, s), 6.64 (1H, dd), 6.75–8.1 (total 19H), 8.40 (1H, dd).
MS (FAB): 661 ($M^+$+1).

(2) After suspending 390 mg of 4'-[(2-phthalimidomethyl-5,6-dihydro-4H-thiazolo[5,4-d][1]benzazepin-6-yl)carbonyl]-2-phenylbenzanilide in 20 ml of methyl alcohol, the resulting suspension was mixed with 1.2 ml of a mixed solvent consisting of 40 weight parts of methylamine and 60 weight parts of methyl alcohol and stirred overnight at room temperature. The reaction solution was concentrated and the thus obtained residue was purified by silica gel column chromatography (chloroform-methyl alcohol=20:1). The thus obtained solid substance was dissolved in 3.5 ml of methyl alcohol, and the resulting solution was mixed with a 4N hydrochloric acid-ethyl acetate solution and then with acetonitrile to effect formation of precipitate. The thus formed precipitate was collected by filtration and washed with a small volume of acetonitrile to obtain 200 mg of 4'-[(2-aminomethyl-5,6-dihydro-4H-thiazolo[5,4-d][1]benzazepin-6-yl)carbonyl]-2-phenylbenzanilide hydrochloride.

Physicochemical properties
HPLC purity: >96%; ODS-80TM (Tosoh)
$^1$H-NMR (δ ppm in DMSO-$d_6$, TMS internal standard): 2.51 (1H, m), 3.09 (1H, m), 3.36 (total 2E), 4.47 (2H, s), 5.02 (1H), 6.85 (2H), 7.11 (1H, t), 7.2–7.7 (total 13H), 7.9 (1H), 8.45 (1H, d), 8.81 (2H), 10.35 (1H, s).
MS (FAB): 531 ($M^+$+1).

EXAMPLE 15

Using 400 mg of 2-phenyl-4'-[(5-oxo-2,3,4,5-tetrahydro-1H-1-benzazepin-1-yl)carbonyl]benzanilide and 300 mg of 2-phthalimidopropanethioamide, the procedure of Example 14 was repeated to obtain 135 mg of 4'-[(2-aminoethyl-5,6-dihydro-4H-thiazolo[5,4-d][1]benzazepin-6-yl)carbonyl]-2-phenylbenzanilide hydrochloride.
Physicochemical properties
HPLC purity: >91%; ODS-80TM (Tosoh)
$^1$H-NMR (δ ppm in DMSO-$d_6$, TMS internal standard): 3.05 (1H, m), 3.40–3.37 (total 6H), 5.01 (1H, m), 6.77 (1H, d), 6.91 (2H, d), 7.09 (1H, t), 7.25–7.58 (total 12H), 8.14 (1H, br), 8.38 (1H, d), 10.33 (1H, s).
MS (FAB): 545 (M$^+$+1).

EXAMPLE 16

Using 400 mg of 2-phenyl-4'-[(5-oxo-2,3,4,5-tetrahydro-1H-1-benzazepin-1-yl)carbonyl]benzanilide and 376 mg of 3-phthalimidobutylthioamide, the procedure of Example 14 was repeated to obtain, using ethyl alcoholethyl acetate as a recrystallization solvent, 193 mg of 4'-[(2-aminopropyl-5,6-dihydro-4H-thiazolo[5,4-d][1]benzazepin-6-yl)carbonyl]-2-phenylbenzanilide hydrochloride.
Physicochemical properties
Melting point: 185°–188° C.

Elemental analysis data ($C_{34}H_{30}N_4O_2S \cdot HCl \cdot H_2O$)

|  | C(%) | H(%) | N(%) | S(%) | Cl(%) |
|---|---|---|---|---|---|
| Calc.: | 62.50 | 5.29 | 8.41 | 6.39 | 7.90 |
| Found: | 62.27 | 5.09 | 8.51 | 5.17 | 8.15 |

$^1$H-NMR (δ ppm in DMSO-$d_6$, TMS internal standard): 2.09 (2H, m), 2.97 (2H, m), 3.05 (1H, m), 3.10 (1H, t), 3.34 (2H, m), 5.01 (1H, m), 6.77 (1H, d), 6.89 (2H, d), 7.08 (1H, t), 7.26–7.58 (total 12H), 7.99 (2H, br), 8.33 (1H, d), 10.33 (1H, s).
MS (FAB): 5 59 (M$^+$+1).

EXAMPLE 17

After dissolving 176 mg of t-butoxycarbonylglycine, 205 mg of 1-hydroxybenztriazole and 0.15 ml of N-methylmorpholine in 3.5 ml of dichloromethane, 192 mg of 1-ethyl-3-(3-dimethylaminopropyl)carbodiimide hydrochloride was added to the resulting solution with stirring on an ice bath, and the mixture was warmed up to room temperature and stirred for 60 minutes. To this reaction solution, again cooled on an ice bath, was added dropwise 4 ml of dichloromethane in which 400 mg of the 4'-[(2-amino-5,6-dihydro-4H-thiazolo(5,4-d][1]benzazepin-6-yl) carbonyl]-2-phenylbenzanilide hydrobromide described in Example 1 and 0.103 ml of triethylamine had been dissolved, followed by overnight stirring at room temperature. The reaction solution was mixed with water, stirred for 60 minutes and then subjected to phase separation. The dichloromethane layer was separated, washed with a saturated sodium bicarbonate aqueous solution and a saturated sodium chloride aqueous solution once for each and then dried over anhydrous magnesium sulfate. After removing the solvent by distillation, the thus obtained residue was suspended in 3 ml of methyl alcohol. With cooling on an ice bath, the suspension was mixed with 4.4 ml of 4N hydrochloric acid-dioxane and stirred for 3 hours. Thereafter, the reaction solution was concentrated and the thus obtained residue was recrystallized from 2-propyl alcohol to obtain 250 mg of 4'-[(2-glycylamino-5,6-dihydro-4H-thiazolo[5,4-d][1]benzazepin-6-yl)carbonyl]-2-phenylbenzanilide 2-propylalcohol hydrochloride.
Physicochemical properties
Melting point: >230° C.

Elemental analysis data ($C_{33}H_{27}N_6O_3S \cdot HCl \cdot C_3H_8O$)

|  | C(%) | H(%) | N(%) | S(%) | Cl(%) |
|---|---|---|---|---|---|
| Calc.: | 64.51 | 5.41 | 10.45 | 4.78 | 5.29 |
| Found: | 64.35 | 5.19 | 10.20 | 4.80 | 5.10 |

$^1$H-NMR (δ ppm in DMSO-$d_6$, TMS internal standard): 1.04 -(6H, d), 3.80 (1H, m), 5.05 (1H), 6.7–7.8 (total 16H), 8.24 (1H, dd), 10.30 (1H, s).
MS (FAB): 574 (M$^+$+1).

EXAMPLE 18

After dissolving 500 mg of 2-phenyl-4'-[(5-oxo-2,3,4,5-tetrahydro-1H-1-benzazepin-1-yl)carbonyl]benzanilide in a mixed solvent consisting of 15 ml of chloroform and 1.5 ml of ethyl acetate, the resulting solution was mixed with 560 mg of copper(II) bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 10 ml of acetonitrile, and the resulting solution was mixed with 750 mg of potassium carbonate and 510 mg of acetoamidine hydrochloride and subjected to 90 minutes of heating under reflux with vigorous stirring. After cooling down the reaction solution to room temperature, insoluble materials were removed by filtration and then the solvent was distilled off under a reduced pressure. The resulting residue was dissolved in chloroform, and the resulting solution was washed with water and dried over anhydrous magnesium sulfate. After distilling off the solvent, the thus obtained residue was purified by silica gel column chromatography (chloroform-methyl alcohol=20:1) to obtain, in the order of elution, 4'-[(2-methyl-5,6-dihydro-4H-oxazolo[4,5-d][1]benzazepin-6-yl)carbonyl]-2-phenylbenzanilide and 4'-[(2-methyl-1,4,5,6-tetrahydro-imidazo[4,5-d][1]benzazepin-6-yl)carbonyl]-2-phenylbenzanilide.

4'-[(2-Methyl-5,6-dihydro-4H-oxazolo[4,5-d][1]benzazepin-6-yl)carbonyl]-2-phenylbenzanilide was recrystallized from ethyl acetate to obtain 40 mg of crystals (Example 18(1)).

4'-[(2-Methyl-1,4,5,6-tetrahydroimidazo[4,5-d][1]benzazepin-6-yl)carbonyl]-2-phenylbenzanilide was dissolved in 5 ml of ethyl alcohol, the resulting solution was mixed with 0.19 ml of 4N hydrochloric acid-ethyl acetate and cooled on an ice bath and then the thus precipitated crystals were collected by filtration and washed with a small volume of ethyl alcohol to obtain 220 mg of 4'-[(2-methyl-1,4,5,6-tetrahydroimidazo[4,5-d][1]benzazepin-6-yl)carbonyl]-2-phenylbenzanilide hydrochloride (Example 18(2)).
Physicochemical properties 4'-[(2-Methyl-5,6-dihydro-4H-oxazolo[4,5-d][1]benzazepin-6-yl)carbonyl]-2-phenybenzanilide Melting point: 234°–236° C.
$^1$H-NMR (δ ppm in CDCl$_3$, TMS internal standard): 2.57 (3H, s), 2.90 (2H, m), 3.27 (1H, m), 5.17 (1H, m), 6.66 (1H, d), 6.8–7.0 (total 6H), 7.23 (1H), 7.3–7.6 (total 8H), 7.7–7.9 (total 2H).

MS (FAB): 500 (M⁺+1) (Cl): 499 (M⁺).

High Resolution MS (FAB): Found 500. 200597 Calc. 500. 197417 Rational formula $C_{32}H_{25}N_3O_3$ 4'-[(2-Methyl-1,4,5,6-tetrahydroimidazo[4,5-d][1]benzazepin-6-yl)carbonyl]-2-phenylbenzanilide hydrochloride Melting point: >230° C.

¹H-NMR (δ ppm in DMSO-d₆, TMS internal standard): 2.70 (3H, s), 2.99 (1H, t), 3.17 (2H, m), 4.99 (1H, m), 6.8–7.0 (total 3H), 7.14 (1H, t), 7.2–7.7 (total 12H), 8.02 (1H, d), 10.31 (1H, s), 14.6 (total 2H).

MS (FAB): 499 (M⁺+1) (Cl): 498 (M⁺).

High Resolution MS (FAB): Found 499. 215808 Calc. 499. 213401 Rational formula $C_{32}H_{26}N_4O_2$

EXAMPLE 19

After dissolving 800 mg of 2-(4-methylphenyl)-4'-[(5-oxo-2,3,4,5-tetrahydro-1H-1-benzazepin-1-yl)carbonyl]benzanilide in a mixed solvent consisting of 24 ml of chloroform and 2.4 ml of ethyl acetate, the resulting solution was mixed with 560 mg of copper(II) bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 16 ml of acetonitrile, and the resulting solution was mixed with 1.17 g of potassium carbonate and 800 mg of acetoamidine hydrochloride and subjected to 120 minutes of heating under reflux with vigorous stirring. After cooling down the reaction solution to room temperature, insoluble materials were removed by filtration and then the solvent was distilled off under a reduced pressure. The resulting residue was dissolved in chloroform, and the resulting solution was washed with water and dried over anhydrous magnesium sulfate. After distilling off the solvent, the thus obtained residue was purified by silica gel column chromatography (chloroform-methyl alcohol=30:1) to obtain, in the order of elution, 2-(4-methylphenyl)-4'-[(2-methyl-5,6-dihydro-4H-oxazolo[4,5-d][1]benzazepin-6-yl)carbonyl]benzanilide (Example 19(1)) and 2-(4-methylphenyl)-4'-[(2-methyl-1,4,5,6-tetrahydro-imidazo[4,5-d][1]benzazepin-6-yl)carbonyl]benzanilide.

2-(4-Methylphenyl)-4'-[(2-methyl-1,4,5,6-tetrahydroimidazo[4,5-d][1]benzazepin-6-yl)carbonyl]benzanilide was dissolved in 10 ml of ethyl alcohol, the resulting solution was mixed with 0.37 ml of 4N hydrochloric acid-ethyl acetate and cooled on an ice bath and then the thus precipitated crystals were collected by filtration and washed with a small volume of ethyl alcohol to obtain 500 mg of 2-(4-methylphenyl)-4'-[(2-methyl-1,4,5,6-tetrahydroimidazo[4,5-d][1]benzazepin-6-yl)carbonyl]benzanilide hydrochloride (Example 19(2)).

Physicochemical properties 2-(4-Methylphenyl)-4'-[(2-methyl-1,4,5,6-tetrahydro-imidazo[4,5-d][1]benzazepin-6-yl)carbonyl]benzanilide hydrochloride Melting point: 220°–223° C.

¹H-NMR (δ ppm in DMSO-d₆, TMS internal standard): 2.25 (3H, s), 2.67 (3H, s), 3.02 (1H, m), 3.16 (2H, m), 4.99 (1H, m), 6.8–7.0 (total 3H), 7.15 (total 3H), 7.2–7.6 (total 9H), 8.04 (1H, d), 10.33 (1H, s), 14.6 (total 2H).

MS (FAB): 513 (M⁺+1)

EXAMPLE 20

After dissolving 400 mg of 2-phenyl-4'-[(5-oxo-2,3,4,5-tetrahydro-1H-1-benzazepin-1-yl)carbonyl]benzanilide in a mixed solvent consisting of 15 ml of chloroform and 2 ml of ethyl acetate, the resulting solution was mixed with 390 mg of copper(II) bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 20 ml of acetonitrile, and the resulting solution was mixed with 1.1 g of potassium carbonate and 371 mg of ethylcarbamidine carbonate and subjected to 1 hour of heating under reflux with vigorous stirring. After filtration of the reaction solution, solvent in the resulting filtrate was distilled off, and the resulting residue was mixed with a saturated sodium bicarbonate aqueous solution and chloroform to separate the organic layer which was subsequently washed with water and a saturated sodium chloride aqueous solution and dried over anhydrous magnesium sulfate. After distilling off the solvent under a reduced pressure, the thus obtained residue was subjected to silica gel column chromatography and eluted with a mixed solvent of chloroform and methyl alcohol (20:1). The resulting eluate was mixed with 5 ml of 4N hydrochloric acid-ethyl acetate and cooled on an ice bath, and the thus precipitated crystals were collected by filtration and subjected to recrystallization using ethyl alcohol as a recrystallization solvent, thereby obtaining 248 mg of 4'-[(2-ethyl-1,4,5,6-tetrahydroimidazo[4,5-d][1]benzazepin-6-yl)carbonyl]-2-phenylbenzanilide hydrochloride.

Physicochemical properties

Melting point: >230° C.

| Elemental analysis data ($C_{33}H_{28}N_4O_2 \cdot HCl \cdot 1.6H_2O$) | | | |
|---|---|---|---|
| | C(%) | H(%) | N(%) | Cl(%) |
| Calc.: | 68.59 | 5.62 | 9.69 | 6.13 |
| Found: | 68.28 | 5.54 | 9.62 | 6.48 |

¹H-NMR (δ ppm in DMSO-d₆, TMS internal standard): 1.38 (3H, t), 2.99 (1H, t), 3.08 (2H, q), 3.12 (2H, m), 4.98 (1H, m), 6.76 (1H, d), 6.93 (2H, d), 7.14 (1H, t), 7.26–7.58 (total 12H), 8.13 (1H, d), 10.31 (1H, s), 14.70 (1H, br).

MS (FAB): 513 (M⁺+1).

EXAMPLE 21

Using 400 mg of 2-phenyl-4'-[(5-oxo-2,3,4,5-tetrahydro-1H-1-benzazepin-1-yl)carbonyl]benzanilide, 597 mg of propylcarbamidine carbonate and-1.2 g of potassium carbonate, the procedure of Example 20 was repeated to obtain, using ethyl acetate-ethyl alcohol as a recrystallization solvent, 243 mg of 4'-[(2-propyl-1,4,5,6-tetrahydroimidazo[4,5-d][1]benzazepin-6-yl)carbonyl]-2-phenylbenzanilide hydrochloride.

Physicochemical properties
Melting point: >230° C.

| Elemental analysis data (C₃₄H₃₀N₄O₂ · HCl · 2H₂O) | | | | |
|---|---|---|---|---|
| | C(%) | H(%) | N(%) | Cl(%) |
| Calc.: | 68.16 | 5.89 | 9.35 | 5.92 |
| Found: | 68.86 | 5.61 | 9.62 | 6.00 |

¹H-NMR (δ ppm in DMSO-d₆, TMS internal standard): 1.00 (3H, t), 1.80 (2H, q), 2.99 (3H, m), 3.56 (2H, m), 4.99 (1H, m), 6.86 (1H, d), 6.93 (2H, d), 7.13 (1H, t), 7.23–7.58 (total 12H), 8.08 (1H, d), 10.32 (1H, s), 14.60 (1H, br).
MS (FAB): 527 (M⁺+1).

EXAMPLE 22

Using 400 mg of 2-phenyl-4'-[(5-oxo-2,3,4,5-tetrahydro-1H-1-benzazepin-1-yl)carbonyl]benzanilide, 576 mg of benzylcarbamidine carbonate and 740 mg of potassium carbonate, the procedure of Example 20 was repeated to obtain, using ethyl acetate-ethyl alcohol as a recrystallization solvent, 225 mg of 4'-[(2-benzyl-1,4,5,6-tetrahydroimidazo[4,5-d][1]benzazepin-6-yl)carbonyl]-2-phenylbenzanilide hydrochloride.
Physicochemical properties
Melting point: >230° C.

| Elemental analysis data (C₃₈H₃₀N₄O₂ · HCl · 1.5H₂O) | | | | |
|---|---|---|---|---|
| | C(%) | H(%) | N(%) | Cl(%) |
| Calc.: | 71.52 | 5.37 | 8.78 | 5.56 |
| Found: | 71.55 | 5.22 | 8.82 | 5.59 |

¹H-NMR (δ ppm in DMSO-d₆, TMS internal standard): 2.97 (1H, m), 3.09 (2H, m), 3.41 (2H, s), 4.96 (1H, m), 6.86–7.58 (total 22H), 8.14 (1H, d), 10.32 (1H, s), 15.00 (1H, br).
MS (FAB): 575 (M⁺+1).

EXAMPLE 23

Using 400 mg of 2-phenyl-41-[(5-oxo-2,3,4,5-tetrahydro-1H-1-benzazepin-1-yl) carbonyl]benzanilide, 585 mg of cyclopropylcarbamidine carbonate and 750 mg of potassium carbonate, the procedure of Example 20 was repeated to obtain, using ethyl acetate-ethyl alcohol as a recrystallization solvent, 276 mg of 4'-[(2-cyclopropyl-1,4,5,6-tetrahydroimidazo[4,5-d][1]benzazepin-6-yl)carbonyl]-2-phenylbenzanilide hydrochloride.
Physicochemical properties
Melting point; >230° C.

| Elemental analysis data (C₃₄H₂₈N₄O₂ · HCl · 1.5H₂O) | | | | |
|---|---|---|---|---|
| | C(%) | H(%) | N(%) | Cl(%) |
| Calc.: | 69.44 | 5.48 | 9.53 | 6.03 |
| Found: | 69.10 | 5.39 | 9.42 | 6.15 |

¹H-NMR (δ ppm in DMSO-d₆, TMS internal standard): 1.28–1.37 (total 4H), 1.99 (1H, m), 2.96 (1H, m), 3.09 (1H, m), 4.96 (1H, m), 6.83 (1H, d), 6.94 (2H, d), 7.12 (1H, t), 7.21–7.58 (total 12H), 8.17 (1H, d), 10.33 (1H, s), 14.60 (1H, br).
MS (FAB): 525 (M⁺+1).

REFERENCE EXAMPLE 5

Using o-methylbenzoic acid and 1-(4-aminobenzoyl)-2,3,4,5-tetrahydro-1H-1-benzazepin-5-one as starting materials, the procedure of Reference Example 3 was repeated to obtain 2-methyl-4'-[(5-oxo-2,3,4,5-tetrahydro-1H-1-benzazepin-1-yl)carbonyl]benzanilide.
Physicochemical properties
¹H-NMR (δ ppm in CDCl₃, TMS internal standard): 2.47 (3H, s), 2.90 (2H, m), 4.1 (2H), 6.8 (1H, m), 7.1–7.7 (total 10H), 7.82 (2H).
MS (EI): 398 (M⁺).

REFERENCE EXAMPLES 6 to 11

The following compounds were synthesized in the same manner as described in Reference Example 5.

REFERENCE EXAMPLE 6

2-Isopropyl-4'-[(5-oxo-2,3,4,5-tetrahydro-1H-1-benzazepin-1-yl)carbonyl]benzanilide

REFERENCE EXAMPLE 7

2-Methoxy-4'-[(5-oxo-2,3,4,5-tetrahydro-1H-1-benzazepin-1-yl)carbonyl]benzanilide

REFERENCE EXAMPLE 8

2-Ethoxy-4'-[(5-oxo-2,3,4,5-tetrahydro-1H-1-benzazepin-1-yl)carbonyl]benzanilide

REFERENCE EXAMPLE 9

2-Isopropyloxy-4'-[(5-oxo-2,3,4,5-tetrahydro-1H-1-benzazepin-1-yl)carbonyl]benzanilide

REFERENCE EXAMPLE 10

2-Methyl-4'-[(5-oxo-2,3,4,5-tetrahydro-1H-1-benzazepin-1-yl) carbonyl phenylacetoanilide

REFERENCE EXAMPLE 11

2-Methoxy-4'-[(5-oxo-2,3,4,5-tetrahydro-1H-1-benzazepin-1-yl)carbonyl]phenylacetoanilide

REFERENCE EXAMPLE 12

A 1.67 g portion of 2'-methoxybiphen-4-ylcarboxylic acid was dissolved in 17 ml of dichloromethane, 0.95 ml of oxalyl chloride and a catalytically effective amount of dimethylformamide were added to the resulting solution with cooling on an ice bath and then the resulting mixture was warmed up to room temperature. When completion of foaming was confirmed, the reaction solution was concentrated under a reduced pressure and subjected to azeotropic treatment with toluene twice. The thus obtained residue was dissolved in 8.4 ml of dichloromethane and, with cooling on an ice bath, the resulting solution was dropwise added to a solution obtained by dissolving 1.0 g of 5-oxo-2,3,4,5-tetrahydro-1H-1-benzazepine and 1.53 ml of triethylamine in 10 ml of dichloromethane. The reaction solution was warmed up to room temperature and the stirring was continued for 1 hour. The resulting reaction solution was mixed with water and subjected to phase separation to separate dichloromethane layer which was subsequently washed with 0.5N hydrochloric acid and a saturated sodium bicarbonate aqueous solution and dried over anhydrous magnesium sulfate. After removing the solvent by distillation, the thus obtained residue was crystallized from toluene to obtain 1.65 g of 1-(2'-methoxybiphen-4-ylcarbonyl)-5-oxo-2,3,4,5-tetrahydro-1H-1-benzazepine as crude crystals.
Physicochemical properties
$^1$H-NMR (δ ppm in CDCl$_3$, TMS internal standard): 2.17 (2H, m), 2.93 (2H, m), 3.75 (3H, s), 6.7–7.7 (total 8H), 7.79 (1H, d), 7.89 (2H), 8.2 (1H, d).
MS (EI): 371 (M$^+$).

EXAMPLE 24

After dissolving 2.0 g of 2-methyl-4'-[(5-oxo-2,3,4,5-tetrahydro-1H-benzazepin-1-yl)carbonyl]benzanilide in a mixed solvent consisting of 30 ml of chloroform and 3 ml of ethyl acetate, the resulting solution was mixed with 2.47 g of copper(II) bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 80 ml of chloroform, and the resulting solution was mixed with 2.37 g of acetamidine hydrochloride and 4.86 g of potassium carbonate and subjected to 20 hours of heating under reflux in a stream of argon. The resulting reaction solution was mixed with water and subjected to phase separation to separate the organic layer which was subsequently dried over anhydrous magnesium sulfate. After removing the solvent by distillation under a reduced pressure, the thus obtained residue was crystallized from toluene to obtain 1.41 g of 2-methyl-4'-[(2-methyl-1,4,5,6-tetrahydroimidazo[4,5-d][1]benzazepin-6-yl)carbonyl]benzanilide. A 1.0 g portion of this compound was dissolved in 10 ml of ethyl alcohol, mixed with 0.86 ml of 4N hydrochloric acid-ethyl acetate and recrystallized to obtain 860 mg of 2-methyl-4'-[(2-methyl-1,4,5,6-tetrahydroimidazo[4,5-d][1]benzazepin-6-yl)carbonyl]benzanilide hydrochloride.
Physicochemical properties
Melting point: >230° C.
$^1$H-NMR (δ ppm in DMSO-d$_6$, TMS internal standard): 2.33 (3H, s), 2.70 (3H, s), 3.00 (2H, t), 5.0 (1H, m), 6.99 (2H, d), 7.14 (1H, t), 7.27 (1H, t), 8.17 (1H, d), 10.40 (1H, s), 14.9 (1H, br).
MS (FAB): 437 (M$^+$+1).

EXAMPLE 25

Using 2.0 g of 2-methoxy-4'-[(5-oxo-2,3,4,5-tetrahydro-1H-1-benzazepin-1-yl)carbonyl]benzanilide, 890 mg of crude crystals were obtained by repeating the procedure of Example 24, and 360 mg of 2-methoxy-4'-[(2-methyl-1,4,5,6-tetrahydroimidazo[4,5-d][1]benzazepin-6-yl)carbonyl]benzanilide hydrochloride was obtained from 400 mg of the thus obtained crystals.
Physicochemical properties
Melting point: >210° C.
$^1$H-NMR (δ ppm in DMSO-d$_6$, TMS internal standard): 2.69 (3H, s), 3.00 (1H, t), 3.85 (3H, s), 5.01 (1H, m), 6.88 (1H, d), 7.36 (1H, t), 7.48 (1H, t), 8.14 (1H, d), 10.20 (1H, s), 14.83 (1H, br).
MS (FAB): 453 (M$^+$+1).

EXAMPLE 26

Using 2.0 g of 2-ethoxy-4'-1(5-oxo-2,3,4,5-tetrahydro-1H-1-benzazepin-1-yl)carbonyl]benzanilide, 927 mg of crude crystals were obtained by repeating the procedure of Example 24, and 465 mg of 2-ethoxy-4'-[(2-methyl-1,4,5,6-tetrahydroimidazo[4,5-d][1]benzazepin-6-yl)carbonyl]benzanilide hydrochloride was obtained from 500 mg of the thus obtained crystals.
Physicochemical properties
Melting point: >220° C.
$^1$H-NMR (δ ppm in DMSO-d$_6$, TMS internal standard): 1.344 (3H, t), 2.70 (3H, s), 3.00 (1H, t), 4.16 (3H, q), 5.02 (1H, m), 6.88 (1H, d), 7.03 (3H, m), 7.13 (1H, t), 7.35 (1H, t), 7.46 (1H, t), 7.54 (1H, d), 8.18 (1H, d), 10.19 (1H, s), 14.86 (1H, br).
MS (FAB): 467 (M$^+$+1).

EXAMPLE 27

A 410 mg portion of bromine dissolved in 2 ml of chloroform was dropwise added gradually (spending about 60 minutes) to 20 ml of chloroform solution containing 1.0 g of 2-isopropoxy-4'-[(5-oxo-2,3,4,5-tetrahydro-1H-1-benzazepin-1-yl)carbonyl]benzanilide at room temperature. When disappearance of the color of bromine was confirmed, the reaction solution was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 40 ml of chloroform, and the resulting solution was mixed with 1.10 g of acetamidine hydrochloride and 2.25 g of potassium carbonate and subjected to 20 hours of heating under reflux in a stream of argon. The resulting reaction solution was mixed with water and stirred to collect precipitated solid substance by filtration, and the thus collected compound was suspended in 20 ml of ethyl alcohol, mixed with 0.58 ml of 4N hydrochloric acid-ethyl acetate and recrystallized to obtain 600 mg of 2-isopropoxy-4'-[(2-methyl-1,4,5,6 -tetrahydroimidazo[4,5-d][1]benzazepin-6-yl)carbonyl benzanilide hydrochloride.
Physicochemical properties
Melting point: >300° C.
$^1$H-NMR (δ ppm in DMSO-d$_6$, TMS internal standard): 1.30 (6H, d), 2.68 (3H, s), 3.02 (1H, t), 4.72 (1H, q), 5.0 (1H, m), 6.89 (1H, d), 7.37 (1H, t), 7.65 (1H, d), 8.10 (1H, d), 10.18 (1H, s), 14.7 (1H, br).
MS (FAB): 481 (M$^+$+1).

EXAMPLE 28

A 1.32 g portion of bromine dissolved in 6.6 ml of chloroform was dropwise added gradually (spending about 60 minutes) to 36 ml of chloroform solution containing 3.55 g of 4'-[(5-oxo-2,3,4,5-tetrahydro-1H-1-benzazepin-1-yl)carbonyl]-2-isopropoxybenzanilide at room temperature. When disappearance of the color of bromine was confirmed, the reaction solution was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 40 ml of chloroform, and the resulting solution was mixed with 5.0 g of cyclopropylcarbamidine hydrochloride and 8.02 g of potassium carbonate and subjected to 20 hours of heating under reflux in a stream of argon. The resulting reaction solution was mixed with water to effect phase separation, and the separated organic layer was dried over anhydrous magnesium sulfate. After removing the solvent by distillation under a reduced pressure, the thus obtained residue was crystallized from toluene to obtain 2.96 g of 4'-[(2-cyclopropyl-1,4,5,6-tetrahydroimidazol4,5-d][1]benzazepin-6-yl)carbonyl]-2-isopropoxybenzanilide. A 1.08 g portion of this compound was dissolved in 20 ml of ethyl alcohol, mixed with 0.8 ml of 4N hydrochloric acid-ethyl acetate and recrystallized to obtain 916 mg of 4'-[(2-cyclopropyl-1,4,5,6-tetrahydroimidazo[4,5-d][1]benzazepin-6-yl)carbonyl]-2-isopropoxybenzanilide hydrochloride.
Physicochemical properties
Melting point: >210° C.
$^1$H-NMR (δ ppm in DMSO-$d_6$, TMS internal standard): around 1.36 (total 10H), 2.98 (1H, t), 3.46 (1H, br), 4.72 (1H, q), 5.0 (1H, m), 6.87 (1H, d), 7.37 (1H, t), 7.66 (1H, d), 8.17 (1H, d), 10.18 (1H, s), 14.4 (1H, br).
MS (FAB): 507 ($M^+$+1).

EXAMPLE 29

Using 5.0 g of 2-fluoro-4'-[(5-oxo-2,3,4,5-tetrahydro-1H-1-benzazepin-1-yl)carbonyl]benzanilide, 4.76 g of crude crystals were obtained by repeating the procedure of Example 24, and 1.02 g of 2-fluoro-4'-[(2 -methyl-1,4,5,6-tetrahydroimidazo[4,5-d][1]benzazepin-6-yl)carbonyl] benzanilide hydrochloride was obtained from 1.0 g of the thus obtained crystals.
Physicochemical properties
Melting point: >270° C.
$^1$H-NMR (δ ppm in DMSO-$d_6$, TMS internal standard): 2.70 (3H, s), 3.01 (1H, t), 5.02 (1H, m), 6.87 (1H, d), 7.02 (2H, m), 7.14 (1H, t), 8.18 (1H, d), 10.55 (1H, s), 14.8 (1H, br).
MS (FAB): 440 ($M^+$+1).

EXAMPLE 30

With cooling on an ice bath, a 793 mg portion of phenyltrimethylammonium tribromide was added to 20 ml of tetrahydrofuran solution containing 1.0 g of 4'-[(5-oxo-2,3,4,5-tetrahydro-1H-1-benzazepin-1-yl)carbonyl)-2-isopropylbenzanilide, and the mixture was warmed up to room temperature. Filtration was carried out when disappearance of the color of bromine was confirmed after about 60 minutes. The filtered material was washed with tetrahydrofuran, and the filtrates were combined and concentrated. The thus obtained residue was dissolved in chloroform, washed with a sodium bicarbonate aqueous solution and then dried over anhydrous magnesium sulfate. After distilling off the solvent, the residue was further evaporated to dryness using a vacuum pump. The thus obtained solid substance was dissolved in 40 ml of chloroform, and the resulting solution was mixed with 1.11 g of acetamidine hydrochloride and 2.26 g of potassium carbonate and subjected to 20 hours of heating under reflux in a stream of argon. The resulting reaction solution was mixed with water to effect phase separation, and the organic layer was separated and dried over anhydrous magnesium sulfate. After removing the solvent by distillation under a reduced pressure, the thus obtained residue was crystallized from toluene to obtain 640 mg of 2-isopropoxy-4'-[(2-methyl-1,4,5,6-tetrahydroimidazo[4,5-d][1]benzazepin-6-yl)carbonyl]benzanilide. A 563 mg portion of this compound was dissolved in 5.5 ml of ethyl alcohol, mixed with 0.45 ml of 4N hydrochloric acid-ethyl acetate and recrystallized to obtain 400 mg of 2-isopropyl-4'-[(2-methyl-1,4,5,6-tetrahydroimidazo[4,5-d][1]benzazepin-6-yl)carbonyl) benzanilide hydrochloride.
Physicochemical properties
Melting point: 251° to 253° C.
$^1$H-NMR (δ ppm in DMSO-$d_6$, TMS internal standard): 1.18 (6H, t), 3.00 (1H, t), 3.38 (2H, br), q), 5.0 (1H, m) 6.89 (1H, d), 7.16 (1H, t), 7.55 (2H, d), 8.11 (1H, d), 10.47 (1H, s), 14.7 (1H, br).
MS (FAB): 465 ($M^+$+1).

EXAMPLE 31

Using 2.0 g of 2-methoxy-4'-[(5-oxo-2,3,4,5-tetrahydro-1H-1-benzazepin-1-yl)carbonyl]phenylacetanilide, 1.19 g of crude crystals were obtained by repeating the procedure of Example 30, and 1.25 g of 2-methoxy-4'-[(2-methyl-1,4,5,6-tetrahydroimidazo[4,5-d][1]benzazepin-6-yl)carbonyl] phenylacetanilide hydrochloride was obtained from 1.19 g of the thus obtained crystals.
Physicochemical properties
Melting point: >200° C.
$^1$H-NMR (δ ppm in DMSO-$d_6$, TMS internal standard): 2.68 (3H, s), 2.98 (1H, t), 3.60 (2H, s), 3.73 (3H, s), 5.0 (1H, m), 7.12 (1H, t), 8.10 (1H, d), 10.26 (1H, s), 14.7 (2H, br).
MS (FAB): 467 ($M^+$+1).

EXAMPLE 32

Using 2.0 g of 2-methyl-4'-[(5-oxo-2,3,4,5-tetrahydro-1H-1-benzazepin-1-yl)carbonyl]phenylacetanilide, 1.26 g of crude crystals were obtained by repeating the procedure of Example 30, and 898 mg of 2-methyl-4'-[(2-methyl-1,4,5,6-tetrahydroimidazo[4,5-d][1]benzazepin-6-yl)carbonyl] phenylacetanilide hydrochloride was obtained from 1.2 g of the thus obtained crystals.
Physicochemical properties
Melting point: 201° to 203° C.
$^1$H-NMR (δ ppm in DMSO-$d_6$, TMS internal standard): 2.25 (3H, s), 2.68 (3H, s), 2.98 (1H, t), 3.66 (2H, s), 5.0 (1H, m), 6.90 (1H, d), 7.34 (1H, t), 8.09 (1H, d), 10.44 (1H, s), 14.7 (2H, br).
MS (FAB): 451 ($M^+$+1).

EXAMPLE 33

A 3 ml portion of a chloroform solution containing 300 mg of bromine was dropwise added gradually (spending about 60 minutes) at room temperature to 700 mg of 1-(2'-methoxybiphenyl-4-ylcarbonyl)-5-oxo-2,3,4,5-tetrahydro-1H-1-benzazepine dissolved in 0.7 ml of chloroform. When disappearance of the color of bromine was confirmed, the reaction solution was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 28 ml of chloroform, and the resulting solution was mixed with 714 mg of acetamidine hydrochloride and 1.46 g of potassium carbonate and subjected to 20 hours of heating under reflux in a stream of argon. The resulting reaction solution was mixed with water to effect phase separation, and the organic layer was separated and dried over anhydrous magnesium sulfate. After distilling off the solvent, the thus obtained residue was purified by silica gel column chromatography (chloroform-methyl alcohol=20:1) to obtain, in the order of elution, 210 mg (glassy solid) of 6-[(2'-methoxy-4-biphenylyl)carbonyl] -2-methyl-5,6-dihydro-4H-oxazolo[4,5-d][1]benzazepine (Example 33(1)) and 390 mg (glassy solid) of 6-[(2'-methoxy-4-biphenylyl)carbonyl]-2-methyl-1,4,5,6-tetrahydroimidazo[4,5-d][1]benzazepine.

6-[(2'-Methoxy-4-biphenylyl)carbonyl]-2-methyl-1,4,5,6-tetrahydroimidazo[4,5-d][1]benzazepine was dissolved in 4.8 ml of ethyl alcohol, the solution was mixed with 0.44 ml of 4N hydrochloric acid-ethyl acetate and cooled on an ice bath to effect crystal formation, and then the thus formed crystals were collected by filtration and washed with a small volume of ethyl alcohol to obtain 260 mg of 6-[(2'-methoxy-4-biphenylyl)carbonyl]-2-methyl-1,4,5,6-tetrahydroimidazo[4,5-d][1]benzazepine hydrochloride (Example 33(2)).
Physicochemical properties 6-[(2'-methoxy-4-biphenylyl)carbonyl-2-methyl-5,6-dihydro-4H-oxazolo[4,5-d][1]benzazepine $^1$H-NMR ($\delta$ ppm in CDCl$_3$, TMS internal standard): 2.57 (3H, s), 3.73 (3H, s), 5.22 (1H, m), 6.78 (1H, dd), 7.82 (1H, dd).

MS (EI): 410 (M$^+$).

6-[(2'-methoxy-4-biphenylyl)carbony]-2-methyl-1,4,5,6-tetrahydroimidazo[4,5-d][1]benzazepine hydrochloride Melting point: >240° C.

$^1$H-NMR ($\delta$ ppm in DMSO-d$_6$, TMS internal standard): 2.69 (3H, s), 3.03 (1H, t), 3.70 (3H, s), 5.02 (1H, m), 6.9–7.4 (total 11H), 8.12 (1H, d), 14.7 (total 2H).

MS EI: 409 (M$^+$)

EXAMPLE 34

A 1.0 g portion of the crude crystals of 2-fluoro-4'-[(2-methyl-1,4,5,6-tetrahydroimidazo[5,4-d][1]benzazepin-6-yl)carbonyl]benzanilide obtained in Example 29 and 1.1 g of 2-ethylimidazole were dissolved in 5 ml of dimethyl sulfoxide and stirred for 24 hours at 120° C. The reaction solution was added to water and extracted twice with chloroform. The chloroform layers were combined, washed with a saturated sodium chloride aqueous solution and then dried over anhydrous magnesium sulfate. After removing the solvent by distillation, the thus obtained residue was purified by silica gel column chromatography using a solvent system of chloroform-methyl alcohol-28% aqueous ammonia (10:1:0.1) to obtain 1.02 g of a glassy solid. This compound was dissolved in 20 ml of ethyl alcohol, mixed with 1.42 ml of 4N hydrochloric acid-ethyl acetate and then concentrated. The thus obtained residue was made into an amorphous powder using isopropyl alcohol and then collected by filtration to obtain 460 mg of 2-(2-ethyl-1H-imidazol-1-yl)-4'-(2-methyl-1,4,5,6-tetrahydroimidazo[4,5-d][1]benzazepin-6-yl)carbonyl]benzanilide.2HCl.
Physicochemical properties $^1$H-NMR ($\delta$ ppm in DMSO-d$_6$, TMS internal standard): 2.70 (3H, s), 3.01 (1H, t), 5.02 (1H, m), 7.12 (1H, t), 8.24 (1H, d), 10.93 (1H, s).

MS (FAB): 517 (M$^+$+1)

REFERENCE EXAMPLE 13

A 5.46 g portion of 3-phthalimidopropionitrile was dissolved in 35 ml of dry chloroform, 1.76 ml of dry ethanol was added to the solution and then hydrochloric acid gas was bubbled for 30 minutes into the resulting mixture with cooling on an ice bath, followed by 12 hours of stirring. The reaction solution was mixed with ether, the thus formed precipitate was collected by filtration and dissolved in 150 ml of ethanol and then the resulting solution was mixed with 3 g of ammonium carbonate and stirred at room temperature for 24 hours. By distilling off the solvent from the reaction solution, 5.5 g of 3-phthalimidopropanecarboxyamidine ½ carbonate was obtained.
Physicochemical properties
MASS (FAB): 218 (M$^+$+1)

REFERENCE EXAMPLE 14

Using 2.963 g of 3-phthalimidobutylonitrile as a starting material, the procedure of Reference Example 13 was repeated to obtain 3.162 g of 4-phthalimidobutanecarboxyamidine ½ carbonate.
Physicochemical properties
MS (FAB): 232 (M$^+$+1)

REFERENCE EXAMPLE 15

Using 4.472 g of 5-phthalimidovaleronitrile as a starting material, the procedure of Reference Example 13 was repeated to obtain 4.364 g of 5-phthalimidopentanecarboxyamidine ½ carbonate.
Physicochemical properties
MS (FAB): 245 (M$^+$+1)

REFERENCE EXAMPLE 16

After dissolving 3.03 g of 2-phenyl-4'-[(5-oxo-2,3,4,5-tetrahydro-1H-1-benzazepin-1-yl)carbonyl]benzanilide in a mixed solvent consisting of 120 ml of chloroform and 15 ml of ethyl acetate, the resulting solution was mixed with 2.95 g of copper(II) bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. A 500 mg portion of the thus obtained foam-like substance was dissolved in 150 ml of chloroform, and the resulting solution was mixed with 900 mg of potassium carbonate and 1.3 g of 3-phthalimidopropanecarboxyamidine ½ carbonate and obtained in Reference Example 13, and subjected to 16 hours of heating under reflux. After cooling down the reaction solution to room temperature, insoluble materials were removed by filtration. The resulting filtrate was mixed with a saturated sodium bicarbonate aqueous solution and the organic layer was separated. The resulting organic layer was washed with water and a saturated sodium chloride solution, and dried over anhydrous magnesium sulfate. After distilling off the solvent under a reduced pressure, the thus obtained residue was subjected to silica gel column chromatography to obtain 221 mg of 4'-[[2-(2-phthalimidoethyl)-1,4,5,6-tetrahydroimidazo[4,5-d][1]benzazepin-6-yl]carbonyl]-2-phenylbenzanilide from chloroform-methyl alcohol (50:1) eluate.
Physicochemical properties
MS (FAB): 658 (M$^+$+1)

REFERENCE EXAMPLE 17

After dissolving 3.03 g of 2-phenyl-4'-[(5-oxo-2,3,4,5-tetrahydro-1H-1-benzazepin-1-yl)carbonyl]benzanilide in a mixed solvent consisting of 120 ml of chloroform and 15 ml of ethyl acetate, the resulting solution was mixed with 2.95 g of copper bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. Using a 500 mg portion of the thus obtained foam-like substance and 1.758 g of 4-phthalimidobutanecarboxyamidine ½ carbonate obtained in Reference Example 14 as starting materials, the similar procedure as in Reference Example 16 was repeated to obtain 389 mg of 4'-[[2-(3-phthalimidopropyl)-1,4,5,6-tetrahydroimidazo[4,5-d][1]benzazepin-6-yl]carbonyl]-2-phenylbenzanilide.
Physicochemical properties
MS (FAB): 672 (M$^+$+1)

REFERENCE EXAMPLE 18

After dissolving 3.03 g of 2-phenyl-4'-[(5-oxo-2,3,4,5-tetrahydro-1H-1-benzazepin-1-yl)carbonyl]benzanilide in a mixed solvent consisting of 120 ml of chloroform and 15 ml of ethyl acetate, the resulting solution was mixed with 2.95 g of copper bromide and subjected to 3 hours of heating under reflux with vigorous stirring. After cooling down the reaction solution to room temperature, insoluble materials were removed by filtration. The resulting filtrate was washed with a saturated sodium bicarbonate aqueous solution. The resulting organic layer was dried over anhydrous magnesium sulfate, concentrated under a reduced pressure and then evaporated to dryness using a vacuum pump. Using a 500 mg portion of the thus obtained foam-like substance and 1.424 g of 5-phthalimidopentanecarboxyamidine ½ carbonate obtained in Reference Example 15 as starting materials, the similar procedure as in Reference Example 16 was repeated to obtain 316 mg of 4'-[[2-(4-phthalimidobutyl)-1,4,5,6-tetrahydroimidazo[4,5-d][1]benzazepin-6-yl]carbonyl]-2-phenylbenzanilide.
Physicochemical properties
MS (FAB): 686 (M$^+$+1)

REFERENCE EXAMPLE 19

In a stream of argon, 60% sodium hydride was dissolved in 10 ml of tetrahydrofuran, and the solution was mixed with 2.0 g of benzyl cyanide, stirred for 1 hour at room temperature, further mixed with 3.69 g of 1,4-dibromobutane and again stirred for 16 hours at room temperature. The reaction mixture was mixed with water and ethyl acetate, and the resulting organic layer was separated, washed with a saturated sodium chloride aqueous solution and then dried over anhydrous magnesium sulfate. After removing the solvent by distillation under a reduced pressure, the thus obtained residue was subjected to silica gel column chromatography, and the resulting hexane eluate was mixed with 45 ml of sulfuric acid and subjected to 24 hours of heating under reflux. After cooling down to room temperature, the reaction solution was mixed with ice water and ethyl acetate to separate water layer which was subsequently mixed with concentrated hydrochloric acid and ethyl acetate, and the resulting organic layer was separated, washed with water and a saturated sodium chloride aqueous solution and then dried over anhydrous magnesium sulfate. By removing the solvent by distillation under a reduced pressure, 978 mg of 2-cyclopentyl-2-phenylacetic acid was obtained.
Physicochemical properties
$^1$H-NMR (δ ppm in CDCl$_3$, TMS internal standard): 1.84–2.08 (m, 8H), 7.21–7.45 (m, 4H)
MS (EI): 190 (M$^+$)

REFERENCE EXAMPLE 20

Using 2.0 g of benzyl cyanide and 3.9 g of 1,5-dibromopentane, the procedure of Reference Example 19 was repeated to obtain 980 mg of 2-cyclohexyl-2-phenylacetic acid.
Physicochemical properties
$^1$H-NMR (δ ppm in CDCl$_3$, TMS internal standard): 1.26–1.87 (m, 10H), 7.22–7.52 (m, 4H) MS (EI): 204 (M$^+$)

REFERENCE EXAMPLE 21

In 20 ml of dichloromethane, a 978 mg portion of 2-cyclopentyl-2-phenylacetic acid obtained in Reference Example 19 was mixed with 0.7 ml of oxazyl chloride and stirred for 1 hour on an ice bath. After distilling off the reaction solvent, the thus obtained residue was dissolved in 10 ml of dichloromethane and added to a 20 ml dichloromethane solution containing 1.24 g of 1-(4-aminobenzoyl)-2,3,4,5-tetrahydro-1H-1-benzazepin-5-one and 0.72 ml of triethylamine, and the mixture was stirred for 3 hours at room temperature. The resulting reaction solution was mixed with a saturated sodium carbonate aqueous solution to separate the organic layer which was subsequently washed with water and a saturated sodium chloride aqueous solution and dried over anhydrous magnesium sulfate. After removing the solvent by distillation under a reduced pressure, the thus obtained residue was subjected to silica gel column chromatography to obtain 759 mg of 1-[4-(1-phenylcyclopentan-1-yl)aminobenzoyl]-5-oxo-2,3,4,5-1H-1-benzazepine from the chloroform-methyl alcohol (50:1) eluate.
Physicochemical properties
MS (FAB): 453 (M$^+$+1)

REFERENCE EXAMPLE 22

Using 980 mg of 2-cyclohexyl-2-phenylacetic acid and 1.2 g of 1-(4-aminobenzoyl)-2,3,4,5-tetrahydro-1H-1-benzazepin-5-one as starting materials, the procedure of Reference Example 21 was repeated to obtain 1.453 g of 1-[4-(1-phenylcyclopentan-1-yl)aminobenzoyl]-5-oxo-2,3,4,5-1H-1-benzazepine.
Physicochemical properties
MS (FAB): 467 (M$^+$+1)

REFERENCE EXAMPLE 23

After dissolving 2.966 g of 1-(4-nitrobenzoyl)-2,3,4,5-tetrahydro-1H-1-benzazepin-5-one in a mixed solvent consisting of 925 ml of chloroform and 9.2 ml of ethyl acetate, the resulting solution was mixed with 5.34 g of copper bromide and subjected to 2 hours of heating under reflux with vigorous stirring. After cooling down the reaction solution to room temperature, insoluble materials were removed by filtration and the resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 250 ml of chloroform, and the resulting solution was mixed with 10.5 g of potassium carbonate and 5.12 g of acetamidine hydrochloride and subjected to 20 hours of heating under reflux. After cooling down the reaction solution to room temperature, insoluble materials were removed by filtration and the resulting filtrate was washed with a saturated sodium bicarbonate aqueous solution, water and a saturated sodium chloride aqueous solution and then dried over anhydrous magnesium sulfate. After removing the solvent by distillation under a reduced pressure, the thus obtained residue was subjected to silica gel column chromatography to obtain 2.077 g of 6-(4-nitrobenzoyl)-2-methyl-1,4,5,6- tetrahydroimidazo[4,5-d][1]benzazepine from the chloroform-methyl alcohol (30:1) eluate.
Physicochemical properties
MS (FAB): 349 (M$^+$+1)

REFERENCE EXAMPLE 24

In a stream of argon, 144 mg of 60% sodium hydride was suspended in a small volume of N,N-dimethylformamide to which, with cooling on an ice bath, was then added dropwise a solution prepared by dissolving 500 mg of 6-(4-nitrobenzoyl)-2-methyl-1,4,5,6-tetrahydroimidazo[4,5-d][1]benzazepine in 20 ml of N,N-dimethylformamide. After 1 hour of stirring at room temperature, the reaction solution was mixed with 0.11 ml of methyl iodide and stirred for 24 hours at room temperature. The reaction solution was mixed with water and chloroform, and the resulting organic layer was separated, washed with a saturated sodium chloride aqueous solution and then dried over anhydrous magnesium sulfate. After removing the solvent by distillation under a reduced pressure, the thus obtained residue was subjected to silica gel column chromatography to obtain 351 mg of 6-(4-nitrobenzoyl)-2,3-dimethyl-3,4,5,6-tetrahydroimidazo[4,5-d][1]benzazepine from the chloroform-methyl alcohol (30:1) eluate.
Physicochemical properties
$^1$H-NMR (δ ppm in CDCl$_3$, TMS internal standard): 2.37 (3H, s), 2.85–2.90 (1H, m), 3.12 (1H, m), 3.36–3.51 (1H, m), 3.59 (3H, s), 5.14–5.17 (1H, dd), 6.57 (1H, d), 6.83 (1H, t), 7.22–7.26 (3H, m), 7.92 (2H, d), 7.26 (1H, d)
MS (FAB): 303 (M$^+$+1)

REFERENCE EXAMPLE 25

A 1.421 g portion of 6-(4-nitrobenzoyl)-2,3-dimethyl-3,4,5,6-tetrahydroimidazo[4,5-d][1]benzazepine was dissolved in 50 ml of methyl alcohol, and the solution was mixed with 300 mg of palladium-carbon and subjected to hydrogenation under normal pressure. After completion of the hydrogen absorption, the reaction mixture was subjected to filtration and the resulting filtrate was concentrated to obtain 571 mg of 6-(4-aminobenzoyl)-2,3-dimethyl-3,4,5,6-tetrahydroimidazo[4,5-d][1]benzazepine.
Physicochemical properties
MS (FAB): 333 (M$^+$+1)

EXAMPLE 35

A 392 mg portion of 4'-[[2-(2-phthalimidoethyl)-1,4,5,6-tetrahydroimidazo[4,5-d][1]benzazepin-6-yl]carbonyl]-2-phenylbenzanilide obtained in Reference Example 16 was dissolved in 10 ml of methyl alcohol, and the resulting solution was mixed with 10 ml of a methylamine-methyl alcohol solution and stirred at room temperature for 4 hours. The reaction solution was mixed with chloroform and 1N hydrochloric acid to separate water layer which was then mixed with chloroform and neutralized with 1N sodium hydroxide to separate organic layer. The organic layer was washed with water and a saturated sodium chloride aqueous solution, dried over anhydrous magnesium sulfate and then subjected to solvent removal by distillation under a reduced pressure. The thus obtained residue was dissolved in a small volume of ethyl acetate and mixed with 4N hydrochloric acid-ethyl acetate, and the thus formed precipitate was washed with ethyl alcohol to obtain 70 mg of 4'-[[2-(2-aminoethyl)-1,4,5,6-tetrahydroimidazo[4,5-d][1]benzazepin-6-yl]carbonyl]-2-phenylbenzanilide.2HCl as an amorphous solid.
Physicochemical properties $^1$H-NMR (δ ppm in DMSO-d$_6$, TMS internal standard): 1.44–1.64 (m, 3H), 2.06–2.11 (m, 2H), 2.26–2.30 (m, 2H), 4.96 (m, 1H), 6.86–7.58 (total 17H), 8.14 (d, 1H), 15.0 (br, 1H)
MS (FAB): 528 (M$^+$+1)

EXAMPLE 36

Using 389 mg of 4'-[[2-(3-phthalimidopropyl)-1,4,5,6-tetrahydroimidazo[4,5-d][1]benzazepin-6-yl]carbonyl]-2-phenylbenzanilide obtained in Reference Example 17 as a starting material, the procedure of Example 35 was repeated and the product was recrystallized from ethyl acetate-ethyl alcohol to obtain 90 mg of 4'-[[2-(3-aminopropyl)-1,4,5,6-tetrahydroimidazo[4,5-d][1]benzazepin-6-yl]carbonyl]-2-phenylbenzanilide.2HCl.
Physicochemical properties.
Melting point: 220° to 223° C.

| Elemental analysis data (C$_{34}$H$_{33}$N$_5$O$_2$ · 2HCl · 3H$_2$O) | | | |
|---|---|---|---|
| | C(%) | H(%) | N(%) | Cl(%) |
| Calc.: | 60.79 | 5.88 | 10.37 | 10.60 |
| Found: | 60.51 | 5.76 | 9.94 | 10.30 |

$^1$H-NMR (δ ppm in DMSO-d$_6$, TMS internal standard): 1.44–1.64 (3H, m), 2.14–2.17 (2H, m), 3.40–3.45 (4H, m), 4.96 (1H, m), 6.82–7.54 (total 17H), 8.14 (1H, d), 15.0 (1H, br)
MS (FAB): 542 (M$^+$+1).

EXAMPLE 37

Using 316 mg of 4'-[[2-(4-phthalimidobutyl)-1,4,5,6-tetrahydroimidazo[4,5-d][1]benzazepin-6-yl]carbonyl]-2-phenylbenzanilide obtained in Reference Example 18 as a starting material, the procedure of Example 35 was repeated to obtain 136 mg of 4'-[[2-(4-aminobutyl)-1,4,5,6-tetrahydroimidazo[4,5-d][1]benzazepin-6-yl]carbonyl]-2-phenylbenzanilide.2HCl as an amorphous powder.
Physicochemical properties
HPLC purity: >90% (TOSOH ODS-80 T)
$^1$H-NMR (δ ppm in DMSO-d$_6$, TMS internal standard): 1.20–1.26 (2H, m), 1.44–1.64 (3H, m), 2.14–2.17 (2H, m), 3.40–3.43 (4H, br), 4.99 (1H, m), 6.86–7.58 (total 17H), 8.14 (1H, d), 15.0 (1H, br)
MS (FAB): 556 (M$^+$+1).

EXAMPLE 38

After dissolving 726 mg of 1-[4-(1-phenylcyclopentan-1-yl)carboxamidobenzoyl]-5-oxo-2,3,4,5-1H-1-benzazepine obtained in Reference Example 21 in a mixed solvent consisting of 35 ml of chloroform and 4 ml of ethyl acetate, the resulting solution was mixed with 717 mg of copper bromide and subjected to 1 hour of heating under reflux with vigorous stirring. After cooling down the reaction solution to room temperature, insoluble materials were removed by filtration and the resulting filtrate was washed with a saturated sodium bicarbonate aqueous solution. The resulting organic layer was dried over anhydrous magnesium sulfate, concentrated under a reduced pressure and then evaporated to dryness using a vacuum pump. The thus obtained solid substance was dissolved in 50 ml of chloroform, and the resulting solution was mixed with 1.6 g of potassium carbonate and 780 mg of acetamidine hydrochloride and subjected to 20 hours of heating under reflux. After cooling down the reaction solution to room temperature, insoluble materials were removed by filtration and the resulting filtrate was washed with a saturated sodium bicarbonate aqueous solution, water and a saturated sodium chloride aqueous solution, and then dried over anhydrous magnesium sulfate. After removing the solvent by distillation under a reduced pressure, the thus obtained residue was subjected to silica gel column chromatography, the chloroform-methyl alcohol (30:1) eluate was mixed, in ethyl acetate, with 4N hydrochloric acid-ethyl acetate and then the residue obtained after removal of the solvent by distillation was recrystallized from ethyl alcohol to obtain 181 mg of N-[4-[(2-methyl-1,4,5,6-tetrahydroimidazo[4,5-d][1]benzazepin-6-yl)carbonyl] phenylcyclopentanecarboxamido hydrochloride.

Physicochemical properties

Melting point: 213° to 216° C.

Elemental analysis data ($C_{34}H_{30}N_4O_2 \cdot HCl \cdot 2.5H_2O$)

|  | C(%) | H(%) | N(%) | Cl(%) |
|---|---|---|---|---|
| Calc.: | 65.08 | 6.34 | 9.79 | 6.20 |
| Found: | 65.09 | 5.98 | 9.73 | 6.28 |

$^1$H-NMR ($\delta$ ppm in DMSO-$d_6$, TMS internal standard): 1.54–1.64 (8H, m), 1.90–2.00 (1H, m), 3.68 (3H, s), 2.97–3.12, (2H, m), 4.99 (1H, m), 6.82–7.41 (total 13H), 8.08 (1H, d), 14.6 (1H, br)

MS (FAB): 491 ($M^+$+1).

EXAMPLE 39

Using 1.38 g of 1-[4-(1-phenylcyclopentan-1-yl) carboxamidobenzoyl]-5-oxo-2,3,4,5-1H-1-benzazepine, 1.32 g of copper bromide and 1.4 g of acetamidine hydrochloride as starting materials, the procedure of Example 38 was repeated to obtain 877 mg of N-[4-[(2-methyl-1,4,5,6-tetrahydroimidazo[4,5-d][1]benzazepin-6-yl)carbonyl] phenyl]-1-phenylcyclohexanecarboxamido hydrochloride.

Physicochemical properties

Melting point: 222° to 225° C.

Elemental analysis data ($C_{32}H_{32}N_4O_2 \cdot HCl \cdot 1.4H_2O$)

|  | C(%) | H(%) | N(%) | Cl(%) |
|---|---|---|---|---|
| Calc.: | 67.87 | 6.37 | 9.89 | 6.26 |
| Found: | 67.53 | 6.76 | 9.64 | 6.21 |

$^1$H-NMR ($\delta$ ppm in DMSO-$d_6$, TMS internal standard): 1.27–1.73 (10H, m), 1.90–2.00 (1H, m), 3.68 (3H, s), 2.97–3.12 (2H, m), 4.99 (1H, m), 6.82–7.41 (total 13H), 8.08 (1H, d), 14.6 (1H, br)

MS (FAB): 505 ($M^+$+1).

EXAMPLE 40

A 512 mg portion of o-phenylbenzoic acid was dissolved in 30 ml of dichloromethane and, with cooling on an ice bath, the resulting solution was mixed with 0.45 ml of oxazyl chloride and stirred for 1 hour. After distilling off the reaction solvent under a reduced pressure, the thus obtained residue was dissolved in 10 ml of dichloromethane and, with stirring on an ice bath, added dropwise to a 30 ml dichloromethane solution containing 571 mg of 6-(4-aminobenzoyl)-2,3-dimethyl-3,4,5,6-tetrahydroimidazo[4,5-d][1]benzazepine and 0.72 ml of triethylamine. After warming up to room temperature, the reaction solution was stirred for 6 hours. The resulting reaction solution was mixed with a saturated sodium bicarbonate aqueous solution to separate the organic layer which was subsequently washed with water and a saturated sodium chloride aqueous solution and dried over anhydrous magnesium sulfate. After removing the solvent by distillation under a reduced pressure, the thus obtained residue was subjected to silica gel column chromatography, the resulting chloroform-methyl alcohol (30:1) eluate was mixed with 4N hydrochloric acid-ethyl acetate and then the residue obtained after removal of the solvent by distillation was recrystallized from ethyl alcohol-diethyl ether to obtain 230 mg of 4'-[(2,3-dimethyl-3,4,5,6-tetrahydroimidazo[4,5-d][1]benzazepin-6-yl)carbonyl]-2-phenylbenzanilide hydrochloride.

Physicochemical properties

Melting point: 195° to 198° C.

Elemental analysis data ($C_{33}H_{28}N_4O_2 \cdot 1.1HCl \cdot 2.8H_2O$)

|  | C(%) | H(%) | N(%) | Cl(%) |
|---|---|---|---|---|
| Calc.: | 65.71 | 5.80 | 9.29 | 6.47 |
| Found: | 65.73 | 5.61 | 9.82 | 6.96 |

$^1$H-NMR ($\delta$ ppm in DMSO-$d_6$, TMS internal standard): 2.37 (3H, s), 2.85–2.90 (1H, m), 3.12 (1H, m), 3.36–3.51 (1H, m), 3.59 (3H, s), 5.14–5.17 (1H, br), 6.72–7.57 (total 17H), 8.02 (1H, d),

MS (FAB): 513 ($M^+$+1).

REFERENCE EXAMPLE 26

A 3.0 g portion of o-phenylbenzoic acid was dissolved in 15 ml of methylene chloride and, with cooling on an ice bath, a catalytically effective amount of dimethylformamide and 1.98 g of thionyl chloride were added to the solution. After gradually warming up to room temperature, the reaction mixture was stirred for 1 hour at the same temperature and then the solvent was distilled off under a reduced pressure. The resulting residue was mixed with 15 ml of benzene and again concentrated under a reduced pressure. The thus obtained oily material was dissolved in 20 ml of acetone and, with cooling on an ice bath, mixed with 2.08 g of p-aminobenzoic acid and 2.02 g of N,N-dimethylaniline, followed by gradual warming up to room temperature. After 1.5 hours of stirring at the same temperature, the reaction solution was mixed with 20 ml of water to collect the precipitate by filtration. By drying under a reduced pressure, 4.52 g of 4-(biphen-2-ylcarboxyamide)benzoic acid was obtained in the form of white crystalline powder.

Physicochemical properties

NMR ($\delta$ ppm, DMSO-$d_6$, TMS internal standard): 7.28–7.61 (9H), 7.66 (2H, d), 7.86 (2H, d), 10.57 (1H, s)

MS (EI): 317 ($M^+$)

REFERENCE EXAMPLE 27

A 500 mg portion of 4-(biphen-2-ylcarboxyamide) benzoic acid was dissolved in 5 ml of methylene chloride and, with cooling on an ice bath, a catalytically effective amount of dimethylformamide and 220 mg of oxalyl chloride were added to the solution. After gradually warming up to room temperature, the reaction mixture was stirred for 1.5 hours at the same temperature and then the solvent was distilled off under a reduced pressure. The resulting residue was mixed with 10 ml of benzene and again concentrated under a reduced pressure. The thus obtained oily material was dissolved in 5 ml of methylene chloride to obtain an acid chloride solution.

With cooling on an ice bath, the thus prepared acid chloride solution was added to 2.5 ml of a methylene chloride solution containing 254 mg of 5-oxo-2,3,4,5-tetrahydro-1H-1-benzazepine and 149 mg of pyridine. After gradually warming up to room temperature, the reaction mixture was stirred for about 2 hours at the same temperature. The resulting reaction solution was mixed with 5 ml of methylene chloride and 10 ml of water to separate organic layer which was subsequently washed with 10 ml of dilute hydrochloric acid and 10 ml of 5% sodium carbonate aqueous solution. After concentrating the organic layer under a reduced pressure, the thus obtained amorphous powder was subjected to silica gel column chromatography (eluent; methylene chloride-ethyl acetate=6:1) to collect fractions containing the compound of interest, and then the solvent was removed from the fractions by distillation to obtain 530 mg of 2-phenyl-4'-[(5-oxo-2,3,4,5-tetrahydro-1H-1-benzazepin-1-yl)carbonyl]benzanilide in the form of amorphous powder.

Physicochemical properties $^1$H-NMR ($\delta$ ppm in CDCl$_3$, TMS internal standard): 2.19 (2H, m), 2.86 (2H, m), 4.03 (2H), 6.69 (1H, m), 6.8–7.6 (15H), 7.85 (1H, m)

EXAMPLE 41

After dissolving 2.7 g of 2-phenyl-4'-[(5-oxo-2,3,4,5-tetrahydro-1H-1-benzazepin-1-yl)carbonyl]benzanilide in 40 ml of chloroform, the resulting solution was mixed with 1.92 g of pyridinium hydrobromide perbromide and stirred at 40° C. for 60 minutes. After cooling down to room temperature, the reaction solution was washed twice with water and then dried over anhydrous magnesium sulfate. After distilling off the solvent, the thus obtained residue was dissolved in 120 ml of chloroform, and the resulting solution was mixed with 2.7 g of acetamidine hydrochloride and 5.52 g of potassium carbonate and subjected to 20 hours of heating under reflux in a stream of argon. The resulting reaction solution was mixed with water and subjected to phase separation to separate the chloroform layer which was subsequently dried over anhydrous magnesium sulfate. After removing the solvent by distillation, the thus obtained residue was recrystallized from methyl alcohol to obtain 2.09 g of 4'-[(2-methyl-1,4,5,6-tetrahydroimidazo[4,5-d][1]benzazepin-6-yl)carbonyl]-2-phenylbenzanilide. This compound was crystallized from 31.5 ml of ethyl alcohol and 27.2 ml of 1N hydrochloric acid to obtain crude crystals ($\beta$ crystal) of 4'-[(2-methyl-1,4,5,6-tetrahydroimidazo[4,5-d][1]benzazepin-6 -yl)carbonyl]-2-phenylbenzanilide hydrochloride. These crystals were suspended in 45 ml of acetonitrile, heated for 30 minutes under reflux, cooled down, collected by filtration and then dried to obtain crude crystals ($\gamma$ crystal). Thereafter, they were suspended in 26 ml of ethyl alcohol, heated for 30 minutes under reflux, cooled down, collected by filtration and then dried to obtain 1.6 g of 4'-[(2-methyl-1,4,5,6-tetrahydroimidazo[4,5-d][1]benzazepin-6-yl)carbonyl]-2-phenylbenzanilide hydrochloride in the form of crystals ($\alpha$ crystal).

Physicochemical properties ($\alpha$ crystal)
Melting point: >300° C.
$^1$H-NMR ($\delta$ ppm in DMSO-d$_6$, TMS internal standard): 2.66 (3H, s), 3.00 (1H, t), 4.99 (1H, m), 6.89 (2H), 7.14 (1H, t), 8.02 (1H, d), 10.31 (1H, s), 14.6 (1H, br)
MS (EI): 498 (M$^+$) Formulation Examples Injections

| Composition | | |
|---|---|---|
| Formulation 1 | Inventive compound | 1.5 mg |
| | Lactic acid | 0.2 mg |
| | Lactose | 200 mg |
| | Distilled water for injection use | 2.0 ml in total |
| Formulation 2 | Inventive compound | 1.5 mg |
| | Lactic acid | 0.2 mg |
| | Glycerol | 52 mg |
| | Distilled water for injection use | 2.0 ml in total |

About 300 ml of distilled water for injection use containing 0.75 g of the inventive compound and 0.1 g of lactic acid was mixed with about 500 ml of distilled water for injection use containing 100 g of lactose (or 26 g of glycerol), and the mixture was stirred. Contents in the resulting mixture was dissolved by heating the mixture at 60° C. After cooling down to room temperature, total volume of the solution was adjusted to 1,000 ml. The thus prepared solution was filtered through a membrane filter, dispensed and sealed into ampoules in 2 ml portions and then sterilized to obtain injections each ampoule containing 1.5 mg of the inventive compound. Tablets Composition

| Composition | |
|---|---|
| [Tablet] | |
| Inventive compound | 5.0 mg |
| Lactose | 73.2 |
| Corn starch | 18.3 |
| Hydroxypropylcellulose | 3.0 |
| Magnesium stearate | 0.5 |
| Subtotal | 100 mg |
| [Coat] | |
| Hydroxypropyl methylcellulose 2910 | 2.5 mg |
| Polyethylene glycol 6000 | 0.5 |
| Talc | 0.7 |
| Titanium oxide | 0.3 |
| Subtotal | 4 mg |
| Total | 104 mg |

A 25 g portion of the inventive compound was mixed with 366 g of lactose and pulverized using Sample Mill (manufactured by Hosokawa Micron). After uniformly mixing 391 g of the thus pulverized mixture with 91.5 g of corn starch in a fluidized granulation coating machine (manufactured by Okawara Mfg.), 150 g of 10% hydroxypropylcellulose aqueous solution was sprayed on the mixture to effect granulation. After drying, the thus prepared granules were passed through a 24 mesh screen, mixed with 2.5 g of magnesium stearate and then made into tablets, each weighing 100 mg, by a rotary tabletting machine (manufactured by Hata Tekko-sho) using a pestle/mortar system of 6.5 mm$\phi$×7.8 R. Using a coating apparatus (manufactured by Freund Sangyo), 154 g of an aqueous coating solution containing 12.5 g of hydroxypropylcellulose, 2.5 g of polyethylene glycol 6000, 3.5 g of talc and 1.5 g of titanium oxide was sprayed on the thus prepared tablets to obtain film coated tablets each having 4 mg of coated film and containing 5.0 mg of the inventive compound.

The compounds prepared in Reference Examples 1 to 27 and Examples 1 to 41 have the structures shown below.

TABLE 2

| Reference Example No. | Chemical Formula |
|---|---|
| 1 | |
| 2 | |
| 3 | |
| 4 | |

TABLE 3

| Reference Example No. | Chemical Formula |
|---|---|
| 5 | |
| 6 | |
| 7 | |
| 8 | |

TABLE 4

| Reference Example No. | Chemical Formula |
|---|---|
| 9 | (structure) |
| 10 | (structure) |
| 11 | (structure) |
| 12 | (structure) |

TABLE 5

| Reference Example No. | Chemical Formula |
|---|---|
| 13 | (structure) .1/2 H$_2$CO$_3$ |
| 14 | (structure) .1/2 H$_2$CO$_3$ |
| 15 | (structure) .1/2 H$_2$CO$_3$ |
| 16 | (structure) |

TABLE 6
| Reference Example No. | Chemical Formula |
|---|---|
| 17 | 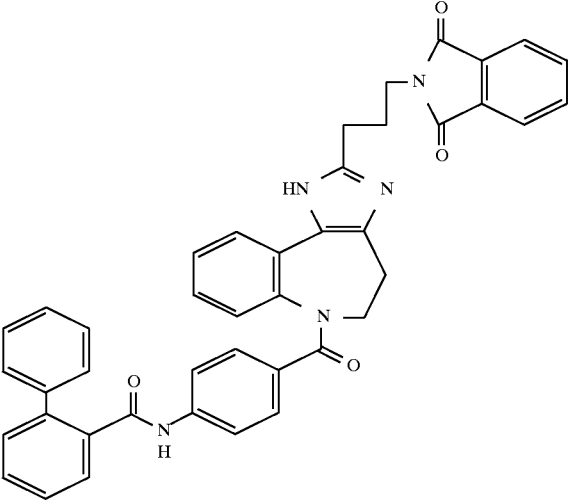 |
| 18 | 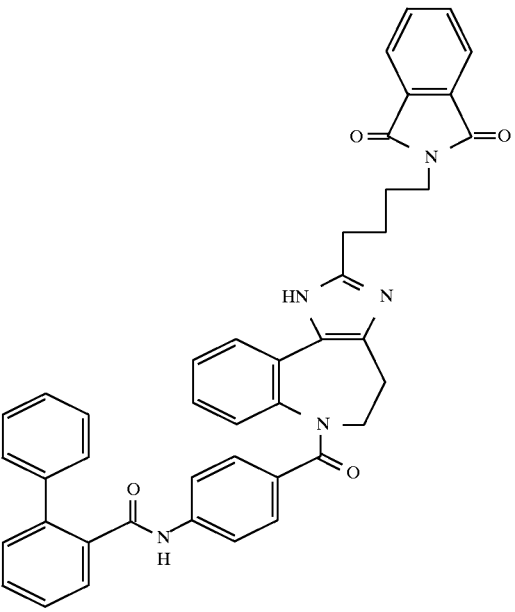 |
| 19 | 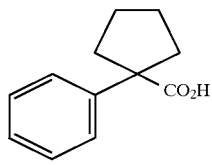 |

TABLE 7
| Reference Example No. | Chemical Formula |
|---|---|
| 20 | 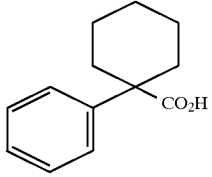 |
| 21 | 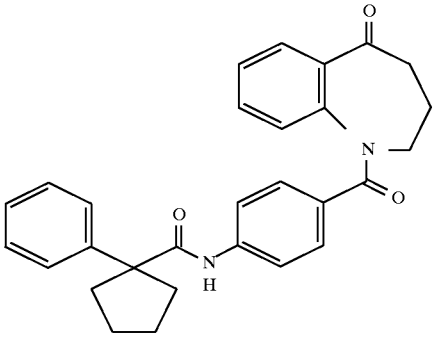 |
| 22 | 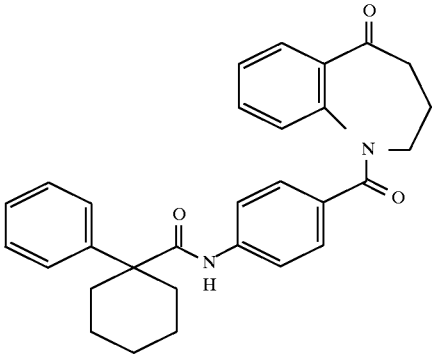 |
| 23 | 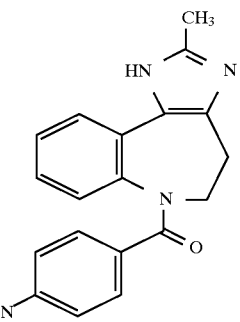 |
TABLE 8
| Reference Example No. | Chemical Formula |
|---|---|
| 24 | 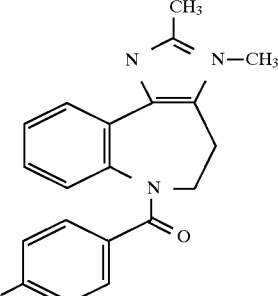 |
| 25 | 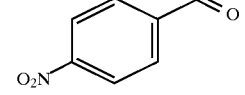 |
| 26 |  |
| 27 | 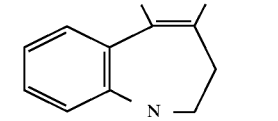 |

TABLE 9

| Example No. | Chemical Formula |
|---|---|
| 1 | (structure) · HBr |
| 2 | (structure) · HBr |

TABLE 9-continued

| Example No. | Chemical Formula |
|---|---|
| 3 | (structure) |

TABLE 10

| Example No. | Chemical Formula |
|---|---|
| 4 | (structure) · HBr |

TABLE 10-continued

| Example No. | Chemical Formula |
|---|---|
| 5 | (structure with .2HCl) |
| 6 | (structure with .2HCl) |

TABLE 11

| Example No. | Chemical Formula |
|---|---|
| 7 | (structure with .HCl) |
| 8 | (structure with .HCl) |

TABLE 11-continued
| Example No. | Chemical Formula |
|---|---|
| 9 | 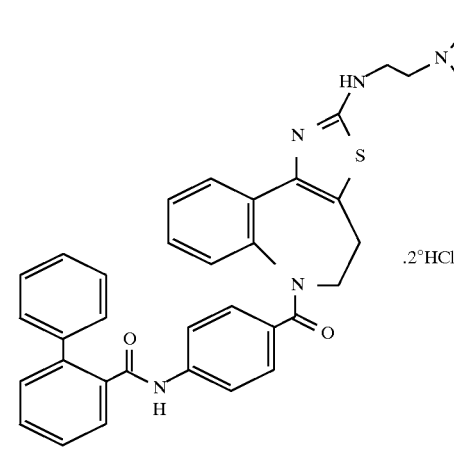 .HCl |
TABLE 12
| Example No. | Chemical Formula |
|---|---|
| 10 | 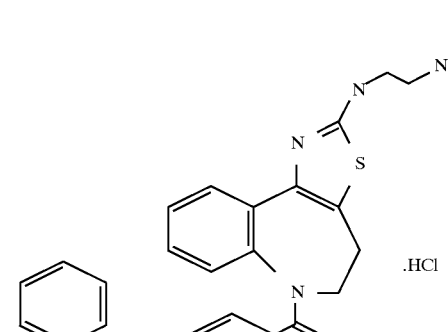 .2·HCl |
| 11 | 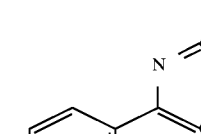 .HCl |
TABLE 12-continued
| Example No. | Chemical Formula |
|---|---|
| 12 | 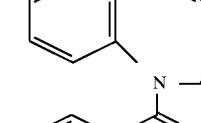 .HCl |
TABLE 13
| Example No. | Chemical Formula |
|---|---|
| 13 | 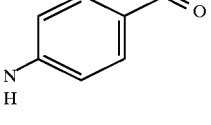 |
| 14 |  .HCl |

TABLE 13-continued
| Example No. | Chemical Formula |
|---|---|
| 15 | 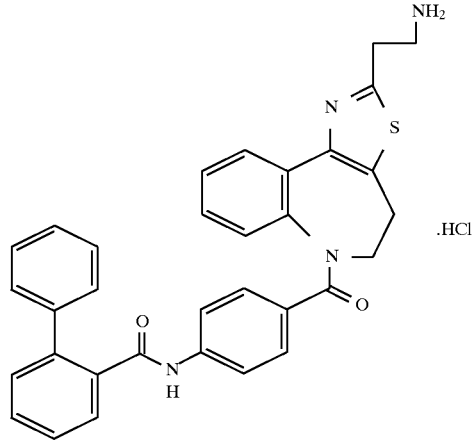 .HCl |
TABLE 14
| Example No. | Chemical Formula |
|---|---|
| 16 | .HCl |
| 17 | .HCl .(CH₃)₂CH(OH) |
TABLE 15
| Example No. | Chemical Formula |
|---|---|
| 18 | (1) |
|  | (2) .HCl |
TABLE 16
| Example No. | Chemical Formula |
|---|---|
| 19 | (1) |

TABLE 16-continued
| Example No. | Chemical Formula |
|---|---|
| (2) | 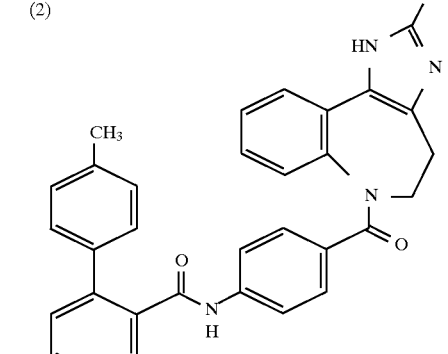 |
TABLE 17
| Example No. | Chemical Formula |
|---|---|
| 20 |  |
| 21 | 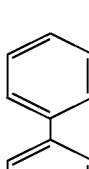 |
TABLE 17-continued
| Example No. | Chemical Formula |
|---|---|
| 22 | 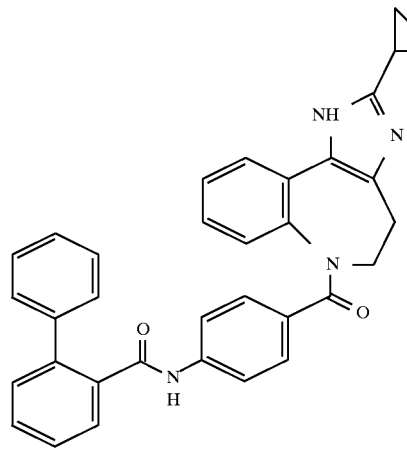 |
TABLE 18
| Example No. | Chemical Formula |
|---|---|
| 23 | 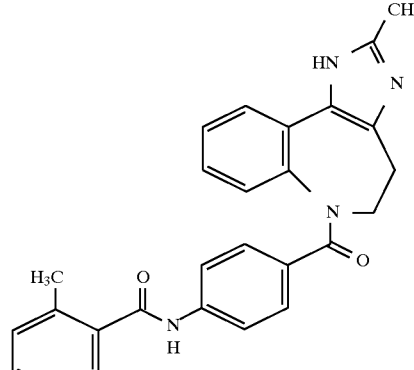 |
| 24 | |

TABLE 18-continued

| Example No. | Chemical Formula |
|---|---|
| 25 | (structure) |

TABLE 19

| Example No. | Chemical Formula |
|---|---|
| 26 | (structure) |
| 27 | (structure) |

TABLE 19-continued

| Example No. | Chemical Formula |
|---|---|
| 28 | (structure) |

TABLE 20

| Example No. | Chemical Formula |
|---|---|
| 29 | (structure) |
| 30 | (structure) |

TABLE 20-continued
| Example No. | Chemical Formula |
|---|---|
| 31 | 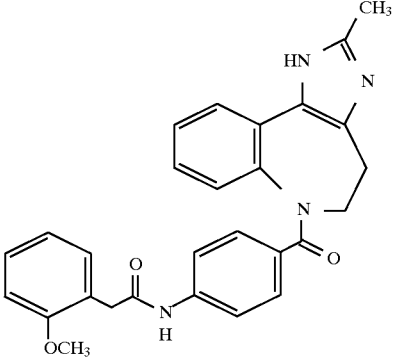 |
TABLE 21
| Example No. | Chemical Formula |
|---|---|
| 32 | |
| 33 | |
TABLE 21-continued
| Example No. | Chemical Formula |
|---|---|
| | 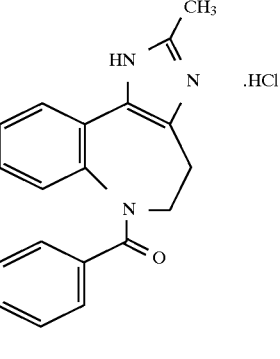 |
TABLE 22
| Example No. | Chemical Formula |
|---|---|
| 34 | |
| 35 | |

TABLE 22-continued
| Example No. | Chemical Formula |
|---|---|
| 36 | 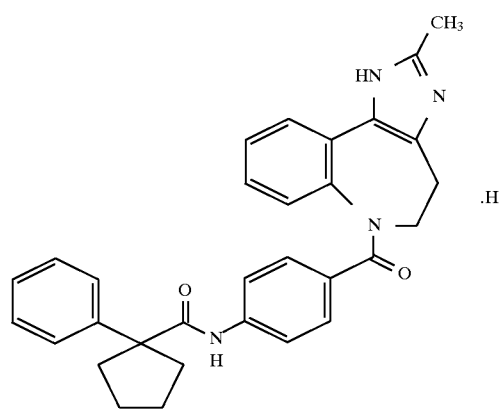 |
TABLE 23
| Example No. | Chemical Formula |
|---|---|
| 37 | |
| 38 | |
| 39 | |
TABLE 24
| Example No. | Chemical Formula |
|---|---|
| 40 | |
| 41 | |

EXAMPLES 42 to 95
According to the processes described in the specification, compounds having the structures shown below are prepared.
EXAMPLES 42 to 49
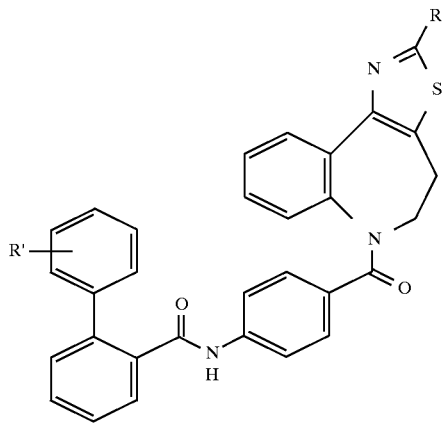
EXAMPLES 50 to 63
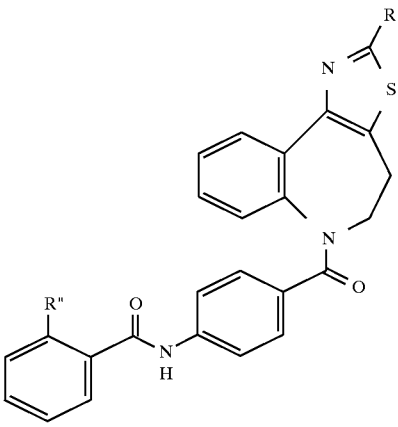
TABLE 25
| No | R | R' | No | R | R' |
|----|---|----|----|---|----|
| 42 | —(CH$_2$)$_2$NH$_2$ | 4-CH$_3$ | 46 | ethyl-piperazine-N—CH$_3$ | 4-CH$_3$ |
| 43 | —(CH$_2$)$_3$NH$_2$ | 4-CH$_3$ | 47 | —NH-C(O)-CH$_2$-NH$_2$ | 4-CH$_3$ |
| 44 | ethyl-imidazole-CH$_3$ | 4-CH$_3$ | 48 | —NH-C(O)-CH$_2$CH$_2$-NH$_2$ | H |
| 45 | ethyl-piperazine-N—CH$_3$ | H | 49 | —NH-C(O)-CH$_2$CH$_2$-NH$_2$ | 4-CH$_3$ |

TABLE 26
| No | R | R" | No | R | R" |
|---|---|---|---|---|---|
| 50 | NH₂ | —OiPr | 57 | 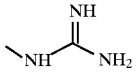 | 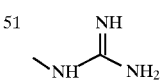 |
| 51 | 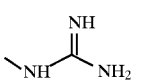 | —OiPr | 58 | 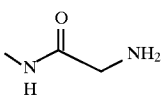 | 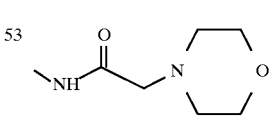 |
| 52 | 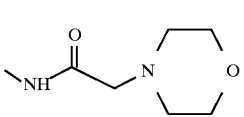 | —OiPr | 59 | 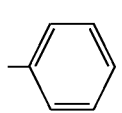 | 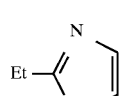 |
| 53 | 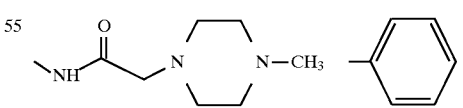 | —OiPr | 60 | 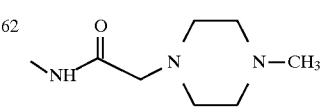 | Et-imidazole |
| 54 | morpholine amide | phenyl | 61 | piperidine amide | Et-imidazole |
| 55 | N-methylpiperazine amide | phenyl | 62 | N-methylpiperazine amide | Et-imidazole |
| 56 | N-methylpiperazine amide | p-tolyl | 63 | Me | Et-imidazole |

EXAMPLES 64 to 75
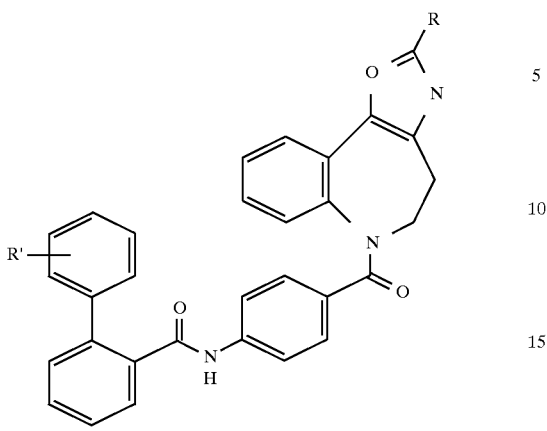
EXAMPLES 76 to 93
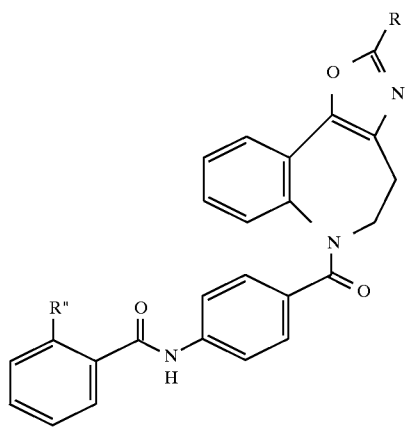
TABLE 27
| No | R | R' | No | R | R' |
|----|---|----|----|---|----|
| 64 | —CH₂NH₂ | H | 70 | ethyl-N-piperazine-N—CH₃ | H |
| 65 | —(CH₂)₂NH₂ | H | 71 | MeNH-C(=NH)-NH₂ | H |
| 66 | —(CH₂)₃NH₂ | H | 72 | MeNH-C(=NH)-NH₂ | 4-CH₃ |
| 67 | —(CH₂)₃NH₂ | 4-CH₃ | 73 | —NH-C(=O)-CH₂-NH₂ | H |
| 68 | 4-ethyl-2-methyl-1H-imidazole | H | 74 | —NH-C(=O)-CH₂-NH₂ | 4-CH₃ |
| 69 | 3-ethylpyridine | H | 75 | —NH-C(=O)-CH₂CH₂-NH₂ | H |

TABLE 28

| No | R | R'' | No | R | R'' |
|---|---|---|---|---|---|
| 76 | —(CH₂)₂NH₂ | —OiPr | 86 | Me | 2-Me, 1-Me-imidazol-yl |
| 77 | 2-ethylpyridine | —OiPr | 87 | Me | 2-Et, 1-Me-imidazol-yl |
| 78 | —(CH₂)₂-morpholine | —OiPr | 88 | cyclopropyl | 2-Et, 1-Me-imidazol-yl |
| 79 | —(CH₂)₂-morpholine | phenyl | 89 | Me | 2-Et, 1-Me-imidazol-yl |
| 80 | NH₂ | —OiPr | 90 | —NHC(O)CH₂-morpholine | 2-Et, 1-Me-imidazol-yl |
| 81 | —NHC(O)CH₂NH₂ | —OiPr | 91 | —NHC(O)CH₂-piperidine | 2-Et, 1-Me-imidazol-yl |
| 82 | —NHC(=NH)NH₂ | —OiPr | 92 | —NHC(O)CH₂-(4-NMe-piperazine) | 2-Et, 1-Me-imidazol-yl |

TABLE 28-continued
| No | R | R'' | No | R | R'' |
|----|---|-----|----|---|-----|
| 83 | 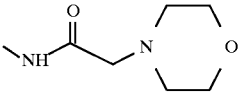 | —OiPr | 93 | 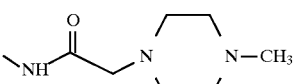 | 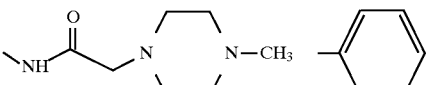 |
| 84 | 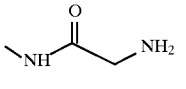 | —OiPr | | | |
| 85 | 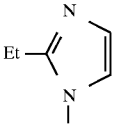 | | | | |
EXAMPLES 94 to 103
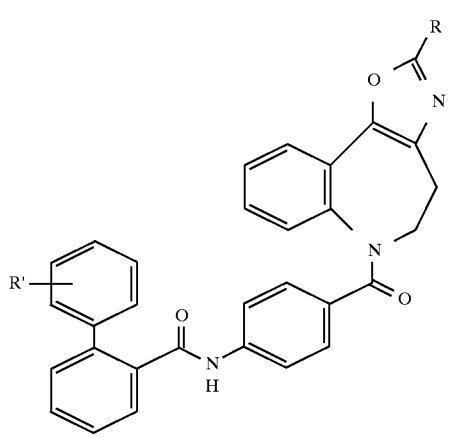
EXAMPLES 104 to 113
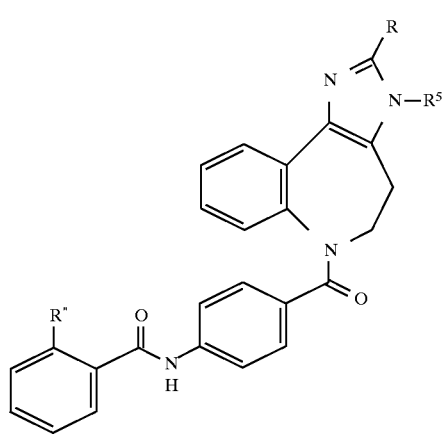
TABLE 29
| No | R | R' | No | R | R' |
|----|---|----|----|---|----|
| 94 | H | H | 99 | —NH$_2$ | H |
| 95 | 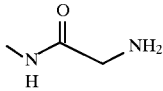 | 4-CH$_3$ | 100 | —NH$_2$ | 4-CH$_3$ |
| 96 | 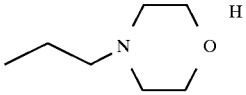 | H | 101 | —N(CH$_3$)$_2$ | H |
| 97 | —CH$_2$NH$_2$ | H | 102 | 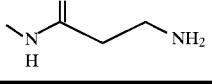 | H |
| 98 |  | H | 103 |  | H |

TABLE 30
| No | R | R⁵ | R" | No | R | R⁵ | R" |
|---|---|---|---|---|---|---|---|
| 104 | —(CH₂)₂NH₂ | —H | —OiPr | 109 | —NHCO(CH₂)₂NH₂ | —H | —OiPr |
| 105 | —(CH₂)₂—N(morpholino) | —H | —OiPr | 110 | —OH | —H | —OiPr |
| 106 | —CH₃ | —CH₃ | 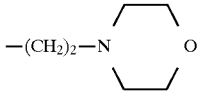 | 111 | —OH | —H |  |
| 107 | 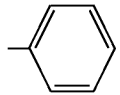 (cyclopropyl) | —CH₃ | —OiPr | 112 | —OCH₃ | —H | 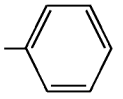 |
| 108 | —NH₂ | —H | —OiPr | 113 | —SC₂H₅ | —H | 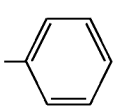 |
We claim:
1. 4-(Biphenyl-2-ylcarboxamide)benzoic acid.
* * * * *